US007928071B2

(12) United States Patent
Ish-Horowicz et al.

(10) Patent No.: US 7,928,071 B2
(45) Date of Patent: Apr. 19, 2011

(54) NUCLEOTIDE AND PROTEIN SEQUENCES OF VERTEBRATE DELTA GENES AND METHODS BASED THEREON

(75) Inventors: David Ish-Horowicz, Oxford (GB); Domingos Manuel Pinto Henrique, Queijas (PT); Julian Hart Lewis, Oxford (GB); Spyridon Artavanis-Tsakonas, Hamden, CT (US); Grace E. Gray, New Haven, CT (US)

(73) Assignees: Yale Universtiy, New Haven, CT (US); Imperial Cancer Research Foundation, Ltd., London (GB)

( * ) Notice: Subject to any disclaimer, the term of this patent is extended or adjusted under 35 U.S.C. 154(b) by 449 days.

(21) Appl. No.: 11/492,497

(22) Filed: Jul. 24, 2006

(65) Prior Publication Data

US 2007/0082846 A1    Apr. 12, 2007

Related U.S. Application Data

(60) Continuation of application No. 09/783,931, filed on Feb. 15, 2001, now Pat. No. 7,118,890, which is a division of application No. 08/981,392, filed as application No. PCT/US96/11178 on Jun. 28, 1996, now Pat. No. 6,262,025.

(60) Provisional application No. 60/000,589, filed on Jun. 28, 1995.

(51) Int. Cl.
*A61K 38/17* (2006.01)
*C07K 14/705* (2006.01)
*C07K 16/28* (2006.01)

(52) U.S. Cl. ............ 514/19.2; 514/19.3; 530/387.1; 530/387.7; 530/388.1; 530/388.15; 530/388.22

(58) Field of Classification Search .................. None
See application file for complete search history.

(56) References Cited

U.S. PATENT DOCUMENTS

| | | | |
|---|---|---|---|
| 5,637,471 A * | 6/1997 | Artavanis-Tsakonas et al. |
| 5,648,464 A * | 7/1997 | Artavanis-Tsakonas et al. |
| 5,750,652 A * | 5/1998 | Artavanis-Tsakonas et al. |
| 5,780,300 A * | 7/1998 | Artavanis-Tsakonas et al. |
| 5,786,158 A * | 7/1998 | Artavanis-Tsakonas et al. |
| 5,789,195 A * | 8/1998 | Artavanis-Tsakonas et al. |
| 5,849,869 A * | 12/1998 | Artavanis-Tsakonas et al. |
| 5,856,441 A * | 1/1999 | Artavanis-Tsakonas et al. |
| 5,869,282 A * | 2/1999 | Ish-Horowicz et al. |
| 6,004,924 A * | 12/1999 | Ish-Horowicz et al. |
| 6,083,904 A * | 7/2000 | Artavanis-Tsakonas et al. |
| 6,090,922 A * | 7/2000 | Artavanis-Tsakonas et al. |
| 6,121,045 A * | 9/2000 | McCarthy et al. |
| 6,149,902 A * | 11/2000 | Artavanis-Tsakonas et al. |
| 6,337,387 B1 * | 1/2002 | Sakano et al. |
| 6,436,650 B1 * | 8/2002 | Artavanis-Tsakonas et al. |
| 6,692,919 B1 * | 2/2004 | Artavanis-Tsakonas et al. |
| 6,703,489 B1 * | 3/2004 | Artavanis-Tsakonas et al. |
| 6,783,956 B2 * | 8/2004 | Ish-Horowicz et al. |
| 7,118,890 B2 * | 10/2006 | Ish-Horowicz et al. |
| 2004/0058443 A1 * | 3/2004 | Artavanis-Tsakonas et al. |
| 2004/0242482 A1 * | 12/2004 | Artavanis-Tsakonas et al. |
| 2005/0112121 A1 * | 5/2005 | Artavanis-Tsakonas et al. |
| 2005/0158859 A1 * | 7/2005 | Artavanis-Tsakonas et al. |
| 2007/0003983 A1 * | 1/2007 | Artavanis-Tsakonas et al. |

FOREIGN PATENT DOCUMENTS

| | | |
|---|---|---|
| EP | 0 861 894 A1 | 9/1998 |
| WO | WO 92/19734 | 11/1992 |
| WO | WO 93/12141 | 6/1993 |
| WO | WO 94/07474 | 4/1994 |
| WO | WO 96/27610 | 9/1996 |
| WO | WO 97/01571 | 1/1997 |
| WO | WO 97/11716 | 4/1997 |
| WO | WO 97/18822 | 5/1997 |
| WO | WO 97/19172 | 5/1997 |
| WO | WO 97/45143 | 12/1997 |
| WO | WO 98/17793 | 4/1998 |
| WO | WO 98/20142 | 5/1998 |
| WO | WO 98/45434 | 10/1998 |
| WO | WO 98/51799 | 11/1998 |
| WO | WO 00/02897 | 1/2000 |

OTHER PUBLICATIONS

Noguer-Troise et al., Blockade of Dll4 inhibits tumor growth by promoting non-productive angiogenesis, Dec. 2006, Nature, vol. 444, pp. 1032-1037.*
Ridgway et al., Inhibition of Dll4 signaling inhibits tumor growth by deregulating angiogenesis, Dec. 2006, Nature, vol. 444, pp. 1083-1087.*
Patel et al., 2005, "Up-regulation of Delta-like 4 Ligand in Human Tumor Vasculature and the Role of Basal Expression in Endothelial Cell Function," Cancer Res. 65(19):8690-8697.
Wu et al., Stabilizing Receptor Quiescence with Synthetic Antibodies Enables Precise Control of Notch Signaling In Vivo, manuscript submitted.
Büchler et al., 2005, "The Notch Signaling Pathway Is Related to Neurovascular Progression of Pancreatic Cancer," Ann. Surg. 242:791-801.
Purow et al., 2005, "Expression of Notch-1 and Its Ligands, Delta-Like-1 and Jagged-1, Is Critical for Glioma Cell Survival and Proliferation," Cancer Res. 65(6):2353-2363.

(Continued)

*Primary Examiner* — Robert Landsman
*Assistant Examiner* — Ian Dang
(74) *Attorney, Agent, or Firm* — Jones Day

(57) ABSTRACT

The present invention relates to nucleotide sequences of vertebrate Delta genes, and amino acid sequences of their encoded proteins, as well as derivatives (e.g., fragments) and analogs thereof. In a specific embodiment, the vertebrate Delta protein is a human protein. The invention further relates to fragments (and derivatives and analogs thereof) of Delta which comprise one or more domains of the Delta protein, including but not limited to the intracellular domain, extracellular domain, DSL domain, domain amino-terminal to the DSL domain, transmembrane region, or one or more EGF-like repeats of a Delta protein, or any combination of the foregoing. Antibodies to Delta, its derivatives and analogs, are additionally provided. Methods of production of the Delta proteins, derivatives and analogs, e.g., by recombinant means, are also provided. Therapeutic and diagnostic methods and pharmaceutical compositions are provided. In specific examples, isolated Delta genes, from *Xenopus*, chick, mouse, and human, are provided.

15 Claims, 40 Drawing Sheets

OTHER PUBLICATIONS

Figure 5A:

Li et al., 2008, "Modulation of Notch Signaling by Antibodies Specific for the Extracellular Negative Regulatory Region of NOTCH3," J. Biol. Chem.
Kogoshi et al., 2007, "γ-Secretase Inhibitors Suppress the Growth of Leukemia and Lymphoma Cells," Oncology Reports 18:77-80.
Park et al., 2006, "Notch3 Gene Amplification in Ovarian Cancer," Cancer Res. 66:6312-6318.
Konishi et al., 2007, "γ-Secretase Inhibitor Prevents Notch3 Activation and Reduces Proliferation in Human Lung Cancers," Cancer Res. 67:8051-8057.
Krop et al., 2006, Abstract 6097, Breast Cancer Research and Treatment 100: Supplement 1.
Farnie et al., 2007, "Mammary Stem Cells and Breast Cancer-Role of Notch Signalling," Stem Cell Rev. 3:169-175.
Farnie et al., 2007, "Novel Cell Culture Technique for Primary Ductal Carcinoma In Situ: Role of Notch and Epidermal Growth Factor Receptor Signaling Pathways," J. Natl. Cancer Inst. 99:616-627.
Dontu et al., 2004, "Role of Notch Signaling in Cell-Fate Determination of Human Mammary Stem/Progenitor cells," Cancer Res. 6:R605-R615.
Politi et al., 2004, "Notch in Mammary Gland Development and Breast Cancer," Sem. Cancer Biol. 14:341-347.
Reedijk et al., 2005, "High-level Coexpression of JAG1 and NOTCH1 Is Observed in Human Breast Cancer and Is Associated with Poor Overall Survival," Cancer Res. 65(18):8530-8537.
Nam et al., 2002, "Notch Signaling As a Therapeutic Target," Curr. Opin. Chem. Biol. 6:501-509.
Jundt et al., 2002, "Activated Notch 1 Signaling Promotes Tumor Cell Proliferation and Survival in Hodgkin and Anaplastic Large Cell Lymphoma," Blood 99(9):3398-3404.
Miele et al., 2006, "NOTCH Signaling as a Novel Cancer Therapeutic Target," Curr. Cancer Drug Targets 6:313-323.
Jang et al., 2000, "Notch Signaling As a Target in Multimodallty Cancer Therapy," Curr. Opin. Mol. Therapeutics 2(1):55-65.
Veeraraghavalu et al., 2004, "Papillomavirus-M Ediated Neoplastic Progression Is Associated With Reciprocal Changes in Jagged1 and Manic Fringe Expression Linked to Notch Activation," J. Virology 78:8687-8700.
Kiaris et al., 2004, "Modulation of Notch Signaling Elicits Signature Tumors and Inhibits Hras1-Induced Oncogenesis in the Mouse Mammary Epithelium," Am. J. Pathology 165:695-705.
Hoek et al., 2004, "Expression Profiling Reveals Novel Pathways in the Transformation of Melanocytes to Melanomas," Cancer Research 64:5270-5282.
Hayashi et al., 2004, "Expression Failure of the Notch Signaling System Is Associated with the Pathogenesis of Testicular Germ Cell Tumor," Tumor Biology 25:99-105.
Dang et al., 2003, "Constitutive Activation of Notch3 Inhibits Terminal Epithelial Differentiation in Lungs of Transgenic Mice," Oncogene 22:1988-1997.
Santagata et al., 2004, "JAGGED1 Expression Is Associated with Prostate Cancer Metastasis," Cancer Res. 64:6854-6857.
Harper et al., 2002, "Developmental Biology: Frontiers for Clinical Genetics," Clin. Genet. 64:461-472.
Office Action dated Mar. 15, 1999 for U.S. Appl. No. 08/937,132.
Office Action dated Dec. 7, 1999 for U.S. Appl. No. 08/937,132.
Advisory Action dated Mar. 7, 2001 for U.S. Appl. No. 08/937,132.
Office Action dated Sep. 18, 2001 for U.S. Appl. No. 08/937,132.
Office Action dated Aug. 8, 2002 for U.S. Appl. No. 08/937,132.
Office Action dated Apr. 23, 2002 for U.S. Appl. No. 09/564,504.
Office Action dated Jan. 14, 2003 for U.S. Appl. No. 09/564,504.
Office Action dated Mar. 23, 2001 for U.S. Appl. No. 09/565,115.
Office Action dated Dec. 19, 2001 for U.S. Appl. No. 09/565,115.
Office Action dated Aug. 9, 2007 for U.S. Appl. No. 10/781,060.
Office Action dated May 14, 2008 for U.S. Appl. No. 10/781,060.
Office Action dated Sep. 23, 2009 for U.S. Appl. No. 11/546,583.
Braydich-Stolle et al., 2005, Role of Glial Cell Line-Derived Neurotrophic Factor in Germ-Line Stem Cell Fate, Ann. N.Y. Acad. Sci. 1061:94-99.
Lasky et al., 2005, Notch Signaling, Brain Development, and Human Disease, Pediatric Research 57(5):104R-109R.
Wolfe, 2009, γ-Secretase in biology and medicine, Seminars in Cell & Developmental Biology 20:219-224.
Rolak, 2003, Multiple Sclerosis: It's Not the Disease You Thought It Was, Clinical Medicine & Research 1(1):57-60.
Sun et al., 1997, Secreted Forms of DELTA and SERRATE define antagonists of Notch signaling in *Drosophila*, Development 124:3439-3448.
Le Roux et al., 2003, Notch activity is required to maintain floorplate identity and to control neurogenesis in the chick hindbrain and spinal cord, Int. J. Dev. Biol. 47:263-272.
U.S. Appl. No. 11/546,583, filed Oct. 10, 2006, Ish-Horowicz et al.*
U.S. Appl. No. 11/605,536, filed Nov. 28, 2006, Artavanis-Tsakonas et al.*
U.S. Appl. No. 09/352,585, filed Jul. 13, 1999, Ish-Horowicz et al.*
U.S. Appl. No. 10/623,469, filed Jul. 18, 2003, Artavanis-Tsakonas et al.*
Apella et al., 1987, "The receptor-binding sequence of urokinase", J. Biol. Chem. 262:4437-4440.
Artavanis-Tsakonas, 1995, "Notch signaling", Science 268:225-232.
Artavanis-Tsakonas, 1988, "The molecular biology of the Notch locus and the fine tuning of differentiation in *Drosophia*", Trends Genet. 4:95-100.
Artavanis-Tsakonas et al., 1991, "Choosing a cell fate: a view from the Notch locus", Trends Genet. 7:403-408.
U.S. Appl. No. 10/661,002, filed Sep. 10, 2003, Artavanis-Tsakonas et al.
Bierkamp et al., 1993, "A zebrafish homologue of the *Drosophila* neurogenic gene Notch and its pattern of transcription during early embryogenesis", Mech. Dev. 43:87-100.
Campos-Ortegan, 1993, "Mechanisms of early neurogenesis in *Drosophia melanogaster*", J. Neurobiol. 24:1305-1327.
Chou et al., 1974, "Prediction of protein conformation", Biochemistry 13:222.
Coffman et al., 1990, "Xotch, the *Xenopus* homolog of *Drosphila* notch", Science 249:1438-1441.
Coffman et al., 1993, Expression of an extracellular deletion of Xotch diverts fate in *Xenopus* embryos, Cell 73:659-671.
Conlon et al., 1995, "Notch 1 is required for the coordinate segmentation of somites", Development 121:1533-1545.
De La Concha et al., 1988, "Functional interactions of neurogenic genes of *Drosophila melanogaster*", Genetics 118:499-508.
Doe, 1992, "Molecular markers for identified neuroblasts and gangolin mother cells in the *Drosophila* central nervous system", Development 116:855-863.
Doe et al., 1985, "Early events in insect neurogenesis", Dev. Biol. 111:206-219.
Fehon et al., 1990, "Molecular interactions between the protein products of the neurogenic loci notch and delta, two EGF-homologous genes in *Drosophila*", Cell 61:523-534.
Fleming et al., 1990, "The gene Serrate encodes a putative EGF-like transmembrane protein essential for proper ectodermal development in *Drosophila melanogaster*", Genes Dev. 4:2188-2201.
Fortini et al., 1993, "Notch: neurogenesis is only part of the picture", Cell 75:1245-1247.
Furie et al., 1988, "The molecular basis of blood coagulation", Cell 53:505-518.
Greenwald, 1994, "Structure/function studies of lin-12/notch proteins", Curr. Opin. Genet. Dev. 4:556-562.
Haenlin et al., 1990, "The pattern of transcription of the neurogenic gene Delta of *Drosophila melanogaster*", Development 110:905-914.
Heitzler et al., 1991, "The choice of cell fate in the epidermis of *Drosophila*", Cell 64:1083-1092.
Henderson et al., 1994, "lag-2 may encode a signaling ligand for the GLP-1 and LIN-12 receptors of *C. elegans*", Development 120:2913-2924.
Hopp et al., 1981, "Prediction of protein antigenic determinants from amino acid sequences", PNAS USA 78:3824.
Kidd et al., 1986, "Sequence of the notch locus of *Drosophila melanogaster*: relationship of the encoded protein to mammalian clotting and growth factors", Mol. Cell. Biol. 6:3094-3108.
Knust et al., 1987, "EGF homologous sequences encoded in the genome of *Drosophila melanogaster*", EMBO J. 6(3): 761-766.

Kooh et al., 1993, "Implications of dynamic patterns of Delta and Notch expression for cellular interactions during *Drosophila* development", Development 117:493-507.

Kopan et al., 1993, "Mouse Notch: expression in hair follicles correlates with cell fate determination", J. Cell. Biol. 121:631-641.

Kopan et al., 1994, "The intracellular domain of mouse Notch: a constitutively activated repressor of myogenesis directed at the basic helix-loop-helix region of MyoD", Development 120:2385-2396.

Kopczynski et al., 1988, "Delta, a *Drosophila* neurogenic gene, is transcriptionally complex and encodes a protein related to blood coagulation factors and epidermal growth factor of vertebrates", Genes Dev. 2:1723-1735.

Kurosawa et al., 1988, "A 10-kDa cyanogen bromide fragment from the epidermal growth factor homology domain of rabbit thrombomodulin contains the primary thrombin binding site", J. Biol. Chem. 263:5993-5996.

Lardelli et al., 1993, "Motch A and motch B- two mouse Notch homologues coexpressed in a wide variety of tissues", Exp. Cell. Res. 204:364-372.

Lardelli et al., 1994, "The novel Notch homologue mouse Notch 3 lacks specific epidermal growth factor-repeats and is expressed in proliferating neuroepithelium", Mech. Dev. 46:123-136.

Mello et al., 1994, "The maternal genes apx-1 and glp-1 and establishment of Dorsal-ventral polarity in the early *C. elegans* embryo", Cell 77:95-106.

Muskavitch, 1994, "Delta-notch signaling and *Drosophila* cell fate choice", Dev. Biol. 166:415-430.

Nüsslein-Volhard et al., 1984, "Mutations affecting the pattern of the larval cuticle in *Drosophila melanogaster*", Dev. Biol. 193:267-282.

Nye et al., 1994, "An activated Notch suppresses neurogenesis and myogenesis but not gliogenesis in mammalian cells", Development 120:2421-2430.

Rebay et al., 1991, "Specific EGF repeats of Notch mediate interactions with delta and serrate: implications for notch as a multi-functional receptor", Cell 67:687-699.

Rebay et al., 1993, "Specific truncations of *Drosophila* Notch define dominant activated and dominant negative forms of the receptor", Cell 74:319-329.

Rees et al., 1988, "The role of -hydroxyaspartate and adjacent carboxylate residues in the first EGF domain of human factor IX", EMBO J. 7:2053-2061.

Rothberg et al., 1988, "slit: An EGF-homologous locus of *D. melanogaster* involved in the development of the embryonic central nervous system", Cell 55:1047-1059.

Sternberg, 1993, "Falling off the knife edge", Current Biol. 3:763-765.

Sudhof et al., 1985, "The LDL receptor gene: a mosaic of exons shared with different proteins", Science 228:815-822.

Suzuki et al., 1987, "Structure and expression of human thrombomodulin, a thrombin receptor on endothelium acting as a cofactor for protein C activation", EMBO J. 6:1891-1897.

Swiatek et al., 1994, "Notch1 is essential for postimplantation development in mice", Genes Dev. 8:707-719.

Tax et al., 1994, "Sequence of *C. elegans* lag-2 reveals a cell-signalling domain shared with Delta and Serrate of *Drosophila*", Nature 368:150-154.

Technau et al., 1986, "Lineage analysis of transplanted individual cells in embryos of *Drosophila melanogaster*", Dev. Biol. 195:445-454.

Thomas et al., 1991, "The *Drosophila* gene Serrate encodes an EGF-like transmembrane protein with a complex expression pattern in embryos and wing discs", Development 111:749-761.

Vässain et al., 1987, The neurogenic gene Delta of *Drosophila melanogaster* is expressed in neurogenic territories and encodes a putative transmembrane protein with EGF-like repeats, EMBO J. 6:3431-3440.

Vässain et al., 1985, "Genetic interactions in early neurogenesis of *Drosophila melanogaster*", J. Neurogenet. 2:291-308.

Weinmaster et al., 1991, "A homolog of *Drosophila* Notch expressed during mammalian development", Development 113:199-205.

Weinmaster et al., 1992, "Notch2: a second mammalian Notch gene", Development 116:931-941.

Wharton et al., 1985, "Nucleotide sequence from the neurogenic locus Notch implies a gene product that shares homology with proteins containing EGF-like repeats", Cell 43:567-581.

Wieschaus et al., 1984, "Mutations affecting the pattern of the larval cuticle in *Drosophila melanogaster*", Dev. Biol. 193:296-307.

Xu et al., 1990, "The notch locus and the genetic circuitry involved in early *Drosophila* neurogenesis", Genes Dev. 4:464-475.

Yochem et al., 1988, "The *Caenorhabditis elegans* lin-12 gene encodes a transmembrane protein with overall similarity to *Drosophila* Notch", Nature 335:547-550.

Henrique et al., 1995, "Expression of a Delta homologue in prospective neurons in the chick", Nature 375(6534):787 90.

Bettenhausen et al., 1995, "Transient and restricted expression during mouse embryogenesis of DLL1, a murine gene closely related to *Drosophila* Delta", Development.121(8):2407 2418.

Chitnis et al., 1995, "Primary neurogenesis in *Xenopus* embryos regulated by a homologue of the *Drosophila* neurogenic gene Delta", Nature. 375(6534):761 766.

Lindsell et al., 1995, "Jagged: A Mammalian Ligand that Activates Notch 1", Cell 80:909-917.

Nye et al., 1995, "Vertebrate Ligands for Notch", Current Biology 5(9):966-969.

Ellisen et al., 1991, "TAN-1, the Human Homolog of the *Drosophilia* Notch Gene, is Broken by Chromosomal Tranlocations in T Lymphoblastic Neoplasms", Cell 66:649-661.

Betenhausen et al., 1995, "Efficient isolation of novel mouse genes differentially expressed in early postimplantation embryos", Genomics 28:436-441.

Artavanis-Tsakonas et al., 1991, "The Notch locus and the cell biology of neuroblast segregation", Annu. Rev. Cell. Biol. 7:427-452.

Austin et al., 1995, "Vertebrate retinal ganglion cells are selected from competent progenitors by the action of Notch", Development 121:3637-3650.

Myat et al., 1996, "A chick homologue of Serrate and Its Relationship with Notch and Delta Homologues during Central Neurogenesis", Developmental Biology 174:233-247.

* cited by examiner

```
     GAATTCGGCACGAGGTTTTTTTTTTTTTTTTCCCCTCTTTTCTTTCTTTTCCTTTTGCC
  1  ------------+---------+---------+---------+---------+---------+ 60

ATCCGAAAGAGCTGTCAGCCGCCGCCGGGCTGCACCTAAAGGCGTCGGTAGGGGGATAAC
 61  ------------+---------+---------+---------+---------+---------+ 120

AGTCAGAGACCCTCCTGAAAGCAGGAGACGGGACGGTACCCCTCCGGCTCTGCGGGGCGG
121  ------------+---------+---------+---------+---------+---------+ 180

CTGCGGCCCCTCCGTTCTTTCCCCCTCCCCGAGAGACACTCTTCCTTTCCCCCCACGAAG
181  ------------+---------+---------+---------+---------+---------+ 240

ACACAGGGGCAGGAACGCGAGCGCTGCCCCTCCGCCATGGGAGGCCGCTTCCTGCTGACG
241  ------------+---------+---------+---------+---------+---------+ 300

CTCGCCCTCCTCTCGGCGCTGCTGTGCCGCTGCCAGGTTGACGGCTCCGGGGTGTTCGAG
301  ------------+---------+---------+---------+---------+---------+ 360

CTGAAGCTGCAGGAGTTTGTCAACAAGAAGGGGCTGCTCAGCAACCGCAACTGCTGCCGG
361  ------------+---------+---------+---------+---------+---------+ 420

GGGGGCGGCCCCGGAGGCGCCGGGCAGCAGCAGTGCGACTGCAAGACCTTCTTCCGCGTC
421  ------------+---------+---------+---------+---------+---------+ 480

TGCCTGAAGCACTACCAGGCCAGCGTCTCCCCCGAGCCGCCCTGCACCTACGGCAGCGCC
481  ------------+---------+---------+---------+---------+---------+ 540

ATCACCCCCGTCCTCGGCGCCAACTCCTTCAGCGTCCCCGACGGCGCGGGCGGCGCCGAC
541  ------------+---------+---------+---------+---------+---------+ 600

CCCGCCTTCAGCAACCCCATCCGCTTCCCCTTCGGCTTCACCTGGCCCGGCACCTTCTCG
601  ------------+---------+---------+---------+---------+---------+ 660

CTCATCATCGAGGCTCTGCACACCGACTCCCCCGACGACCTCACCACAGAAAACCCCGAG
661  ------------+---------+---------+---------+---------+---------+ 720

CGCCTCATCAGCCGCCTGGCCACCCAGAGGCACCTGGCGGTGGGCGAGGAGTGGTCCCAG
721  ------------+---------+---------+---------+---------+---------+ 780

GACCTGCACAGCAGCGGCCGCACCGACCTCAAGTACTCCTATCGCTTTGTGTGTGATGAG
781  ------------+---------+---------+---------+---------+---------+ 840
```

FIG. 1A1

```
     CACTACTACGGGGAAGGCTGCTCTGTCTTCTGCCGGCCCCGTGACGACCGCTTCGGTCAC
841  ---------+---------+---------+---------+---------+---------+ 900

TTCACCTGTGGAGAGCGTGGCGAGAAGGTCTGCAACCCAGGCTGGAAGGGCCAGTACTGC
901  ---------+---------+---------+---------+---------+---------+ 960

ACTGAGCCGATTTGCTTGCCTGGGTGTGACGAGCAGCACGGCTTCTGCGACAAACCTGGG
961  ---------+---------+---------+---------+---------+---------+ 1020

GAATGCAAGTGCAGAGTGGGTTGGCAGGGGCGGTACTGTGACGAGTGCATCCGATACCCA
1021 ---------+---------+---------+---------+---------+---------+ 1080

GGCTGCCTGCACGGTACCTGTCAGCAGCCATGGCAGTGCAACTGCCAGGAAGGCTGGGGC
1081 ---------+---------+---------+---------+---------+---------+ 1140

GGCCTTTTCTGCAACCAGGACCTGAACTACTGCACTCACCACAAGCCATGCAAGAATGGT
1141 ---------+---------+---------+---------+---------+---------+ 1200

CGGTGTACGTGGTTGTGGCCAGTCCCCTCGATGTGAACAAGAACGGCTGGACCCATGTGT
1201 ---------+---------+---------+---------+---------+---------+ 1260

GGCTCCAGCTGCGAGATTGAAATCAACGAATGTGATGCCAACCCTTGCAAGAATGGTGGA
1261 ---------+---------+---------+---------+---------+---------+ 1320

AGCTGCACGGATCTCGAGAACAGCTATTCCTGTACCTGCCCCCCAGGCTTCTATGGTAAA
1321 ---------+---------+---------+---------+---------+---------+ 1380

AACTGTGAGCTGAGTGCAATGACTTGTGCTGATGGACCGTGCTTCAATGGAGGGCGATGC
1381 ---------+---------+---------+---------+---------+---------+ 1440

ACTGACAACCCTGATGGTGGATACAGCTGCCGCTGCCCACTGGGTTATTCTGGGTTCAAC
1441 ---------+---------+---------+---------+---------+---------+ 1500

TGTGAAAAGAAAATCGATTACTGCAGTTCCAGCCCTTGTGCTAATGGAGCCCAGTGCGTT
1501 ---------+---------+---------+---------+---------+---------+ 1560

GACCTGGGGAACTCCTACATATGCCAGTGCCAGGCTGGCTTCACTGGCAGGCACTGTGAC
1561 ---------+---------+---------+---------+---------+---------+ 1620

GACAACGTGGACGATTGCGCCTCCTTCCCCTGCGTCAATGGAGGGACCTGTCAGGATGGG
1621 ---------+---------+---------+---------+---------+---------+ 1680
```

FIG. 1A2

```
     GTCAACGACTACTCCTGCACCTGCCCCCCGGGATACAACGGGAAGAACTGCAGCACGCCG
1681 ---------+---------+---------+---------+---------+---------+ 1740

GTGAGCAGATGCGAGCACAACCCCTGCCACAATGGGGCCACCTGCCACGAGAGAAGCAAC
1741 ---------+---------+---------+---------+---------+---------+ 1800

CGCTACGTGTGCGAGTGCGCTCGGGGCTACGGCGGCCTCAACTGCCAGTTCCTGCTCCCC
1801 ---------+---------+---------+---------+---------+---------+ 1860

GAGCCACCTCAGGGGCCGGTCATCGTTGACTTCACCGAGAAGTACACAGAGGGCCAGAAC
1861 ---------+---------+---------+---------+---------+---------+ 1920

AGCCAGTTTCCCTGGATCGCAGTGTGCGCCGGGATTATTCTGGTCCTCATGCTGCTGCTG
1921 ---------+---------+---------+---------+---------+---------+ 1980

TACCAGTCGGTGTACGTCATATCAGAAGAGAAAGATGAGTGCATCATAGCAACTGAGGTG
2401 ---------+---------+---------+---------+---------+---------+ 2460

TAAAACAGACGTGACGTGGCAAAGCTTATCGATACCGTCATCAAGCTT
2461 ---------+---------+---------+-------- 2508
```

FIG. 1A3

```
   1 GAATTCGGCACGAGGTTTTTTTTTTTCCCTCCTTTCTTTCCTTTGCCATCCGAAAG      69
  70 AGCTGTCAGCGCGCCGGGCTGCACTTAAAGGCGTCGGTAGGGGATAACAGTCAGAGACCCTCCTGA    138
 139 AAGCAGGAGACGGGACACTCTTCCTTCCCCACGAAGACACAGGGCAGGGGCTGCGGCCCCTCCGGTTCTTTCCCCTC    207
 208 CCCGAGAGACACTCTTCCTTCCCCACGAAGACACAGGGCAGGGGCTGCGGCCCCTCCGGTTCTTTCCCCTC    276
 277 ATGGGAGGCCGCTTCGAGCTGAAGCTGCAGGAGTTTGTCAACAAGAAGGGGCTGCTCAGCAACCGCAACTGC    345
 346 TCCGGGGTGTTGAGCTGAAGCTGCAGGAGTTTGTCAACAAGAAGGGGCTGCTCAGCAACCGCAACTGC    414
 415 TGCCGGGGGCGGCCCCGGAGGCGCGGGCAGCAGCAGTGCGGACTGCAAGACCTTCTTCCGCGTCTGC    483
 484 CTGAAGCACTACCAGGCCAGCGTCTCCCCGACGGGCGGCCACCTAGGGCAGCGCCATCACCCCGTC    552
 553 CTCGGCGCCAACTCCTTCAGCGTCACTGGCTTCACTGGCTTCAGGCGCCACCTTCAGCAACCCATC    621
 622 CGCTTCCCCTTCCGGCTTCACTGGCTTCACGGCGCCACCTTCAGCAACCCATC    690
 691 CCCGACGACCTCACCACAGAAAACCCGGAGACCTGCACAGAGGCTCGCACCGACTCC    759
 760 GTGGGGAGGAGTGGTCCCAGGACTGGTCCCAGAGACCTGCACAGAGGCACTGGCG    828
 829 GTGTGTGATGAGCACTACTACGGGAGAGCGTGGCGAGAAGGTCTGCAACCAGGCTGGAAGGGCCAGTACTGCACTGAG    897
 898 CACTTCACCCTGTGCATTTGCTCTGGGTGTGACAGCAGCAGACGGGCTGGGACAAACCTGGGGAATGCAAGTGCAGA    966
 967 CCGATTTGCTGCTTGGGTGTGACAGCAGCAGACGGGCTGGGACAAACCTGGGGAATGCAAGTGCAGA   1035
1036 GTGGGTTGGCAGGGGCGGTACTGTGACAGTGCATCCGATACCCAGGCTGCCTGCACGGTACCTGTCAG   1104
1105 CAGCCATGGCAGTGCAACTGCCAGGAAGGCTGGGGCGGCCCTTTTCTGCAACCAGGAGCTGAACTACTGC   1173
1174 ACTCACCACCAAGGCCATGCAAGAATGGTGCCACATGCCACATGCCAGAGAATCAACGAATGTGATGCCAACCCTTGTTCT   1242
1243 TGCCAGGCTGGGTACACAGGCTCCAGCTGCTGCGAGATGAACAGCTATTCCTGTACCTGCCCCCAGGCTTCTATGGTAAA   1311
1312 AATGTGAGCTGAGTGACAGGATCTCGAGAACAGCTATTCCTGTACCTGCCCCCAGGCTTCTATGGTAAA   1380
1381 AACTGTGAGCTGAGTGACAGCTCCAGAGATCTCTGATGACTTGTCTGATGGACGTGCTTCAATGGAGGCGATGCACTGACAAC   1449
1450 CCTGATGGTGGATACAGCTGCCGCTGCCCACTGGGTTATTCTGGGTTCAACTGTGAAAAGAAAATCGAT   1518
1519 TACTGCAGTTCCAGCCCCTTGTGCTAAGGCACTGTGACGACAACGTGGACGATTGCGCCTCCTTCCCCTGCGTC   1587
1588 TGCCAGGCTGGCTTCACTGGCAGCAGGCACTGTGACGACAACGTGGACGATTGCGCCTCCTTCCCCTGCGTC   1656
1657 AATGGAGGGACCTGTCAGGATGGGGTCAACGACTACTCCTGCACCTGCCCCCCGGGATACAAGGGGAAG   1725
1726 AACTGCAGCAGCGCCGGTGAGCAGCAGATGCGAGCACAACACCCCTGCCACAATGGGGCCACCTGCCAGCGAGAGA   1794
```

FIG. 1B1

1795 AGCAACCGCTACGTGTGCGAGTGCGCTCGGGGCTACGGGCCTCAACTGCCAGTTCCTGCTCCCCGAG 1863
1864 CCACCTCAGGGGCCGGTCATCGTTGACTTCACCGAGAAGTACACAGAGGGCCAGAACAGCCAGTTCCC 1932
1933 TGGATCGCAGTGTGCGCCGGGATTATTCTGGTCCTCATGCTGCTCCTCTGTGCGCCATCGTCGTC 2001
2002 TGCGTCAGGTCTGAAGGTGCAGAAGAGGCACCACCAGCCCTGCAGGAGTGAAACGGAGACCATG 2070
2071 AACAACCTGGCGAACTGCAGGAGGACATCTCCATCGGTGCCACTCAGATTAGATACCCA 2139
2140 AACACAAATAAGAAAGTAGACTTTCACAGCGATAAACGGCTACAAAGTTAGATACCCA 2208
2209 TCAGTGGATTACAATTTGGTGCATGAACTCAAGAATGAGGACTCTGTGAAAGAGGAGCATGGCAAATGC 2277
2278 GAAGCCAAGTGTGAAACGTATGATTCAGAGGCAGAAGAAAAGGCCAGTACAGCTAAAAGTAGTGAC 2346
2347 ACTTCTGAAAGAAAACGGCCAGATTCAGTATCAGTTCAAAGGACACAAAGTACCAGTCGGTGTAC 2415
2416 GTCATATATCAGAACGTGAGTGCATCATAGCAACTGAGGTTAGTATCCCACCTGGCAGTCGGACA 2484
2485 AGTCTTGGTGTGATTCCCATCCAGGCGCAGGTCAGTCTCAGTCTGTGGCACTGCTGCCACAGTC 2553
2554 ATCTGTACCCAATGAAAACTGGCCACCTTCAGTCTGCAGACGTTGAAAAAACTTGTTGTGG 2622
2623 ATTAACATAAGCTCCAGTGGGGTTACAGGGACAGCAATTTTTGCAGGCAAGGGTATAACTGTAGTGCA 2691
2692 GTTGTAGCTTACTAACCCTACTGACTCATTCTTTCGTGCTTCTGCAGAGCCTGTTTTTGCTTGGCA 2760
2761 TTGAGGTGAAGTCCTGACCCTCTGCATCCTCGACATAGTCCTGCTTCTTTTATTAACCTCTTCTGGTC 2829
2830 TCTGCTTGTGTTTCTCTCAACAGGTGACGTGAAAACAGAGACGTGACGTGGCAAGCTT 2883

FIG. 1B2

```
  1 MGGRFLLTLA LLSALLCRCQ VDGSGVFELK LQEFVNKKGL LSNRNCCRGG GPGGAGQQQC
 61 DCKTFFRVCL KHYQASVSPE PPCTYGSAIT PVLGANSFSV PDGAGGADPA FSNPIRFPFG
121 FTWPGTFSLI IEALHTDSPD DLTTENPERL ISRLATQRHL AVGEEWSQDL HSSGRTDLKY
181 SYRFVCDEHY YGEGCSVFCR PRDDRFGHFT CGERGEKVCN PGWKGQYCTE PICLPGCDEQ
241 HGFCDKPGEC KCRVGWQGRY CDECIRYPGC LHGTCQQPWQ CNCQEGWGGL FCNQDLNYCT
301 HHKPCKNGAT CTNTGQGSYT CSCRPGYTGS SCEIEINECD ANPCKNGGSC TDLENSYSCT
361 CPPGFYGKNC ELSAMTCADG PCFNGGRCTD NPDGGYSCRC PLGYSGFNCE KKIDYCSSSP
421 CANGAQCVDL GNSYICQCQA GFTGRHCDDN VDDCASFPCV NGGTCQDGVN DYSCTCPPGY
481 NGKNCSTPVS RCEHNPCHNG ATCHERSNRY VCECARGYGG LNCQFLLPEP PQGPVIVDFT
541 EKYTEGQNSQ FPWIAVCAGI ILVLMLLLGC AAIVVCVRLK VQKRHHQPEA CRSETETMNN
601 LANCQREKDI SISVIGATQI KNTNKKVDFH SDNSDKNGYK VRYPSVDYNL VHELKNEDSV
661 KEEHGKCEAK CETYDSEAEE KSAVQLKSSD TSERKRPDSV YSTSKDTKYQ SVYVISEEKD
721 ECIIATEV
```

|            |     |                |           |               |             |         |     |
|------------|-----|----------------|-----------|---------------|-------------|---------|-----|
| C-Delta-1  | 184 | V- C EHYYGE    | GC SVF CRPRD | DRF GHF TC GE | RGEKV C NPGW | KGQY C  | 228 |
| Delta      | 182 | VT C DLNYYGS   | GC ARF CRPRD | DSF GHS TC SE | TGEII C LTGW | QGDY C  | 226 |
| Serrate    | 235 | VQ C AVTYYNT   | TC TTF CRPRD | DQF GHY AC GS | EGQKL C LNGW | QGVN C  | 279 |
| C-Serrate-1|     | VT C AEHYYGF   | GC NKF CRPRD | DFF THH TC DQ | NGNKT C LEGW | TGPE C  |     |
|            |     |                |           |               |             |         |     |
| Apx-1      | 130 | NL C SSNYHGK   | R C NRY C IAN- | AKLHWE- C ST | HGVRR C SAGW | SGED C  | 172 |
| Lag-2      | 120 | VT C ARNYFGN   | R C ENF C DAHL | AKAARKR C DA | MGRLR C DIGW | MGPH C  | 166 |

FIG. 4

| | | | | |
|---|---|---|---|---|
| CTGCAGGAAT | TCSMYCGCAT | GCCATGGGCC | GTCGGAGCGC | GCTAGCCCTT | 60 |
| GCCGTGGTCT | CTGCCCTGCT | GTGCCAGGTC | TGGAGCTCCG | GCGTATTTGA | 120 |
| CAGGAGTTCG | TCAACAAGAA | GGGGCTGCTG | GGGAACCGCA | ACTGCTGCCG | 180 |
| GGCCCGCCTT | GCGCCTGCAG | GACCTTCTTT | CGCGTATGCC | CCAGGCCAGC | 240 |
| GTGTCACCGG | AGCCACCCTG | CACCTACGGC | AGTGCCGTCA | CGCCAGTGCT | 300 |
| TCCTTCAGCC | TGCCTGATGG | CGCAGGCATC | GACCCCGCCT | TCAGCAACCC | 360 |
| CCCTTCGGCT | TCACCTGGCC | AGGTACCTTC | TCTCTGATCA | TTGAAGCCCT | 420 |
| TCTCCCGATG | ACCTGCAAC | AGAAAACCCA | GAAAGACTCA | GACCACAGAC | 480 |
| AGGCACCTCA | CTGTGGGAGA | AGAATGGTCT | CAGGACCTTC | TCAGCCGCCT | 540 |
| CTCCGGTACT | CTTACCGGTT | TGTGTGTGAC | GAGCACTACT | ACAGTAGCGG | 600 |
| TTCTGCCGAC | CGCCTTTGGC | CACTTCACCT | GCGCCAGAAG | TTGCTCTGTG | 660 |
| ATGTGCGACC | CTGGGATGA | AGGCCAGTAC | TGCACTGACC | CAATCTGTCT | 720 |
| GATGACCAAC | ATGGATACTG | TGACAAACCA | GGGGAGTGCA | AGTGCAGAGT | 780 |
| GGCCGCTACT | GCGATGAGTG | CATCCGATAC | CCAGGTTGTC | TCCATGGCAC | 840 |
| CCCTGGCAGT | GTAACTGCCA | GGAAGGCTGG | GGGGGCCCTT | TCTGCAACCA | 900 |
| TACTGTACTC | ACCATAAGCC | GTGCAGGAAT | GGAGCCACCT | GCACCAACAC | 960 |
| AGCTACACAT | GTTCCTGCCG | ACCTGGGTAT | ACAGGTGCCA | ACTGTGAGCT | 1020 |
| GAGTGTGCTC | CTAGCCCCTG | CAAGAACGGA | GCGAGCTGCA | CGGACCTTGA | 1080 |
| TCTTGCACCT | GCCCCTCCCGG | CTTCTATGGC | AAGGTCTGTG | AGCTGAGCGC | 1140 |
| GCAGATGGCC | CTTGCTTCAA | TGGAGGACGA | TGTTCAGATA | ACCCTGACGG | 1200 |
| TGCCATTGCC | CCTGGGCTT | CTCTGCTTC | AACTGTGAGA | AGAAGATGGA | 1260 |
| TCTTCCCCTT | GTTCTAACGG | TGCCAAGTGT | AACTGTGGCT | GCAACTCTTA | 1320 |
| TGCCAGGCTG | GCTTCTCCGG | GCTTCTCC | GAGGACAATG | TGGATGACTG | 1380 |

FIG. 7A

| | | | | | |
|---|---|---|---|---|---|
| CCGTGTGCAA | ATGGGGGCAC | CTGCCGGGAC | AGTGTGAACG | ACTTCTCCTG | TACCTGCCCA | 1440
| CCTGGCTACA | CGGGCAAGAA | CTGCAGCGCC | CCTGTCAGCA | GGTGTGAGCA | TGCACCCTGC | 1500
| CATAATGGGG | CCACCTGCCA | CCAGAGGGGC | CAGCGCTACA | TGTGTGAGTG | CGCCCAGGGC | 1560
| TATGGCGGCC | CCAACTGCCA | GTTTCTGCTC | CCTGAGCCAC | CACCAGGGCC | CATGGTGGTG | 1620
| GACCTCAGTG | AGAGGCATAT | GGAGAGCCAG | GGCGGGCCCT | TCCCCTGGGT | GGCCGTGTGT | 1680
| GCCGGGGTGG | TGCTTGTCCT | CCTGCTGCTG | CTGGGCGTGT | CTGTGTTTGT | GGTCTGCGTC | 1740
| CGGCTGAAGC | TACAGAAACA | CCAGCCTCCA | CCTGAACCCT | GTGGGGAGA | GACAGAAACC | 1800
| ATGAACAACC | TAGCCAATTG | CCAGCGCGAG | AAGGACGTTT | CTGTTAGCAT | CATTGGGGCT | 1860
| ACCCAGATCA | AGAACACCAA | CAAGAAGGCG | GACTTTCACG | GGGACCATGG | AGCCGAGAAG | 1920
| AGCAGCTTTA | AGTCCGATA | CCCCACTGTG | GACTATAACC | TCGTTCGAGA | CCTCAAGGGA | 1980
| GATGAAGCCA | CGGTCAGGGA | TACACACAGC | AAACGTGACA | CCAAGTGCCA | GTCACAGAGC | 2040
| TCTGCAGGAG | AAGAGAAGAT | CGCCCCAACA | CTTAGGGGTG | GGGAGATTCC | TGACAGAAAA | 2100
| AGGCCAGAGT | CTGTCTACTC | TACTTCAAAG | GACACCAAGT | ACCAGTCCGT | GTATGTTCTG | 2160
| TCTGCAGAGT | AGGATGAGTG | TGTTATAGCG | ACTGAGGTGT | AAGATGGAAG | CGATGTGGCA | 2220
| AAATCCCCAT | TTCTCTTAAA | TAAAATTCCA | AGGATATAGC | CCCGATGAAT | GCTGCTGAGA | 2280
| GAGGAAGGA | GAGGAAACCC | AGGGACTGCT | GCTGAGAACC | AGGTTCAGGC | GAACGTGGTT | 2340
| CTCTCAGAGT | TAGCAGAGGC | GCCGACACT | GCCAGCCTAG | AGTTGCTTT | CCGCTGGACT | 2400
| GCCTGCTGGT | TGTTCCCATT | GCACTATGGA | CAGTTGCTTT | GAAGAGTATA | TATTAAATG | 2460
| GACGAGTGAC | TTGATTCATA | TAGGAAGCAC | CAGTCCCA | CACGTCTATC | TTGGATTACT | 2520
| ATGAGCCAGT | CTTTCCTTGA | ACTAGAAACA | GCACTGCCTT | TATTGTCCTT | TTTGATACTG | 2580
| AGATGTGTTT | TTTTTTTTC | CTAGACGGGA | AAAAGAAAAC | GTGTGTTATT | TTTTTGGGA | 2640
| TTTGTAAAAA | TATTTTTCAT | GATTATGGGA | GAGCTCCCAA | CGCGTTGGAG | GT | 2692

FIG. 7B

| | | | | |
|---|---|---|---|---|
| MGRRSALALA | VVSALLCQVW | SSGVFELKLQ | EFVNKKGLLG | NRNCCRGGSG | 50 |
| PPCACRTFFR | VCLKHYQASV | SPEPPCTYGS | AVTPVLGVDS | FSLPDGAGID | 100 |
| PAFSNPIRFP | FGFTWPGTFS | LIIEALHTDS | PDDLATENPE | RLISRLTTQR | 150 |
| HLTVGEEWSQ | DLHSSGRTDL | RYSYRFVCDE | HYYGEGCSVF | CRPRDDAFGH | 200 |
| FTCGDRGEKM | CDPGWKGQYC | TDPICLPGCD | DQHGYCDKPG | ECKCRVGWQG | 250 |
| RYCDECIRYP | GCLHGTCQQP | WQCNCQEGWG | GLFCNQDLNY | CTHHKPCRNG | 300 |
| ATCTNTGQGS | YTCSCRPGYT | GANCELEVDE | CAPSPCKNGA | SCTDLEDSFS | 350 |
| CTCPPGFYGK | VCELSAMTCA | DGPCFNGGRC | SDNPDGGYTC | HCPLGFSGFN | 400 |
| CEKKMDLCGS | SPCSNGAKCV | DLGNSYLCRC | QAGFSGRYCE | DNVDDCASSP | 450 |
| CANGGTCRDS | VNDFSCTCPP | GYTGKNCSAP | VSRCEHAPCH | NGATCHQRGQ | 500 |
| RYMCECAQGY | GGPNCQFLLP | EPPPGPMVVD | LSERHMESQG | GPFPWVAVCA | 550 |
| GVVLVLLLLL | GCAAVVVCVR | LKLQKHQPPP | EPCGGETETM | NNLANCQREK | 600 |
| DVSVSIIGAT | QIKNTNKKAD | FHGDHGAEKS | SFKVRYPTVD | YNLVRDLKGD | 650 |
| EATVRDTHSK | RDTKCQSQSS | AGEEKIAPTL | RGGEIPDRKR | PESVYSTSKD | 700 |
| TKYQSVYVLS | AEKDECVIAT | EV | | | 722 |

FIG. 8

```
CHICK DELTA      MGGRFLLTLA LLSALLCRCQ VDGSGVFELK LQEFVNKKGL LSNRNCCRGG  50
MOUSE DELTA.PEP  MGRRSALALA VVSALLCQ—  VVSSGVFELK LQEFVNKKGL LGNRNCCRGG  48

CONSENSUS        MG.R..L.LA ..SALLC... V..SGVFELD LQEFVNKKGL L.NRNCCRGG  50

CHICK DELTA      GPGGAGCQQC DCKTFFRVCL KHYQASVSPE PPCTYGSAIT PVLGANSFSV 100
MOUSE DELTA.PEP  —SCP——PC ACRTFFRVCL KHYQASVSPE PPCTYGSAVT PVLGVDSFSL  93

CONSENSUS        ...G.....C .C.TFFRVCL KHYQASVSPE PPCTYGSA.T PVLG..SFS. 100

CHICK DELTA      PDGAGCADPA FSNPIRFPFG FTWPGTFSLI IEALHTDSPD DLTTENPERL 150
MOUSE DELTA.PEP  PDGAG-IDPA FSNPIRFPFG FTWPGTFSLI IEALHTDSPD DLATENPERL 142

CONSENSUS        PDGAG..DPA FSNPIRFPFG FTWPGTFSLI IEALHTDSPD DL.TENPERL 150

CHICK DELTA      ISRLATQRHL AVGEEWSQDL HSSGRTDLKY SYRFVCDEHY YGEGCSVFCR 200
MOUSE DELTA.PEP  ISRLTTQRHL TVGEEWSQDL HSSGRTDLRY SYRFVCDEHY YGEGCSVFCR 192

CONSENSUS        ISRL.TQRHL .VGEEWSQDL HSSGRTDL.Y SYRFVCDEHY YGEGCSVFCR 200

CHICK DELTA      PRDDRFGHFT CGERGEKVCN PGWKGQYCTE PICLPGCDEQ HGFCDKPGEC 250
MOUSE DELTA.PEP  PRDDAFGHFT CGDRGEKVCD PGWKGQYCTD PICLPGCDDQ HGYCDKPGEC 242

CONSENSUS        PRDD.FGHFT CG.RGEK.C. PGWKGQYCT. PICLPGCD.Q HG.CDKPGEC 250

CHICK DELTA      KCRVGWQGRY CDECIRYPGC LHGTCQQPWQ CNCQEGWGGL FCNQDLNYCT 300
MOUSE DELTA      KCRVGWQGRY CDECIRYPGC LHFTCQQPWQ CNCQEGWGGL FCNQDLNYCT 292

CONSENSUS        KCRVGWQGRY CDECIRYPGC LHGTCQQPWQ CNCQEGWGGL FCNQDLNYCT 300

CHICK DELTA      HHKPCKNGAT CTNTGQGSTY CSCRPGYTGS SCEIEINECD ANPCKNGGSC 350
MOUSE DELTA.PEP  HHKPCRNGAT CTNTGQGSYT CSCRPGYTGA NCELEVDECA PSPCKNGASC 342

CONSENSUS        HHKPC.NGAT CTNTGQGSYT CSCRPGYTG. .CE.E..EC. ..PCKNG.SC 350

CHICK DELTA      TDLENSYSCT CPPGFYGKNC ELSAMTCADG PCFNGGRCTD NPDGGYSCRC 400
MOUSE DELTA.PEP  TDLEDSFSCT CPPGFYGKVC ELSAMTCADG PCFNGGRCSD NPDGGYTCHC 392

CONSENSUS        TDLE.S.SCT CPPGFYGK.C ELSAMTCADG PCFNGGRC.D NPDGGY.C.C 400

CHICK DELTA      PLGYSGFNCE KKIDYCSSSP CANGAQCVDL GNSYICQCQA GFTGRHCDDN 450
MOUSE DELTA.PEP  PLGFSGFNCE KKMDLCGSSP CSNGAKCVDL GNSYLCRCQA GFSGRYCEDN 442

CONSENSUS        PLG.SGFNCE KK.D.C.SSP C.NGA.CVDL GNSY.C.CQA GF.GR.C.DN 450
```

FIG.9A

| | | | | | | | |
|---|---|---|---|---|---|---|---|
| CHICK DELTA | VDDCASFPQV | NGGTCQDGVN | DYSCTCPPGY | NGKNCSTPVS | RCEHNPCHNG | 500 |
| MOUSE DELTA.PEP | VDDCASSPQA | NGGTCRDSVN | DFSCTCPPGY | TGKNCSAPVS | RCEHAPCHNG | 492 |
| CONSENSUS | VDDCAS.PQ. | NGGTC.D.VN | D.SCTCPPGY | .GKNCS.PVS | RCEH.PCHNG | 500 |
| CHICK DELTA | ATCHERSNRY | VCECARGYGG | LNCQFLLPEP | PQGPVIVDFT | EKYTECQNSQ | 550 |
| MOUSE DELTA | ATCHRGQRY | MCECAQGYGG | PNCQFLLPEP | PPGPMVVDLS | ERHMESQGGP | 542 |
| CONSENSUS | ATCH.R..RY | .CECA.GYGG | .NCQFLLPEP | P.GP..VD.. | E...E.Q... | 550 |
| CHICK DELTA | FPWIAVCAGI | ILVLMLLLGC | AAIVVCVRLK | VQKRHHQPEA | CRSETETMNN | 600 |
| MOUSE DELTA.PEP | FPWMAVCAGV | VLVLLLLLGC | AAVVVCVRLK | LQKHQPPPEP | CGGETETMNN | 592 |
| CONSENSUS | FPW.AVCAG. | .LVL.LLLGC | AA.VVCVRLK | .QK....PE. | C..ETETMNN | 600 |
| CHICK DELTA | LANCQREKDI | SISVIGATQI | KNTNKKVDFH | SDN-SDKNGY | KVRYPSVDYN | 649 |
| MOUSE DELTA | LANCQREKDV | SMSIIGATQI | KNTNKKADFH | GDHGAEKSSF | KVRYPTVDYN | 642 |
| CONSENSUS | LANCQREKD. | S.S.IGATQI | KNTNKK.DFH | .D....K... | KVRYP.VDYN | 650 |
| CHICK DELTA | LVHELKNED- | SVKEEFGKCE | AKCETYDSEA | EEKSAVQLKS | SDTSERKRPD | 698 |
| MOUSE DELTA.PEP | LVRDLKGDEA | TVRDTHSKRD | TKCQSQSSAG | EEKIAPTLRG | GEIPDRKRPE | 692 |
| CONSENSUS | LV..LK.... | M...H.K... | KC....S. | EEK.A..... | .....RKRP. | 700 |
| CHICK DELTA | SVYSTSKDTK | YQSVYVISEE | KDECIIATEV | 728 |
| MOUSE DELTA.PEP | SVYSTSKDTK | YQSVYVLSAE | KDEQVIATEV | 722 |
| CONSENSUS | SVYSTSKDTK | YQSVYV.S.E | KDEQ.IATEV | 730 |

FIG.9B

```
            10         20         30         40         50         60
                       *                     *                     *
     TACGATGAAY AACCTGGCGA ACTGCCAGCG TCAGAAGGAC ATCTCAGTCA GCATCATCGG
      Y D E     X P G E    L P A     * E G     H L S Q    H H R>
       T M N    N L A      N C Q R    E K D    I S V      S I I G>
        R * X    T W R     T A S     V R R T   S Q S      A S S>

70         80         90        100        110        120
                       *                     *                     *
     GGCYACGTCA GATCARGAAC ACCAACAAGA AGGCGGACTT YMCASCGGGG GACCASAGCG
      G X V     R S X T    P T R     R R T     X X R G    T X A>
       A T S    D Q E      H Q Q E    G G L    X X G      P X R>
        G X R Q  I X N     T N K      K A D F  X X G      D X S>

130        140        150        160        170        180
                       *                     *                     *
     TCCGACAAGA ATGGMTTTCA AGGCCYGCTA CCCCAGCGTG GACTATAACT CGTGCAGGAC
      S D K     N G F Q    G P L     P Q R     G L * L    V Q D>
       P T R    M X F      K A R Y    P S V    D Y N      S C R T>
        V R Q E  W X S     R P A     T P A W   T I T      R A G>

190        200        210        220        230        240
                       *                     *                     *
     CTCAAGGGTG ACGACACCGC CGTCAGGACG TCGCACAGCA AGCGTGACAC CAAGTGCCAG
      L K G     D D T A    V R T     S H S     K R D T    K C Q>
       S R V    T T P      P S G R    R T A    S V T      P S A S>
        P Q G *  R H R     R Q D     V A Q Q   A * H      Q V P>

250        260        270        280        290        300
                       *                     *                     *
     TCCCCAGGCT CCTCAGGGAG GAGAAGGGGA CCCCGACCAC ACTCAGGGGK TGCGTGCTGC
      S P G     S S G R    R R G     P R P     H S G X    A C C>
       P Q A    P Q G      G E G D    P D H    T Q G      X R A>
        V P R L  L R E     E K G     T P T T   L R G      C V L>

310        320        330        340        350        360
                       *                     *                     *
     GGGCCGGGCT CAGGAGGGGG TACCTGGGGG GTGTCTTCCT GGAACCACTG CTCCGTTTCT
      G P G     S G G G    T W G     V S S     W N H C    S V S>
       G R A    Q E G      V P G G    C L P    G T T      A P F L>
        R A G L  R R G     Y L G     G V F L   E P L      L R F>
```

FIG. 10A

```
           370          380           390          400          410          420
                         *                          *                        *
     CTTCCCAAAT  GTTCTCATGC   ATTCATTGTG  GATTTTCTCT  ATTTTCCTTT  TAGTGGAGAA
       L P K      C S H A      F I V      D F L       Y F P F     S G  E>
        F P N      V L M      H S L W     I F S        I F L       L V E K>
       S S Q M    F S C        I H C     G F S L      F S F        *  W  R>

430          440           450          460          470          480
                         *                          *                        *
     GCATCTGAAA  GAAAAAGGCC   GGACTCGGGC  TGTTCAACTT  CAAAAGACAC  CAAGTACCAG
      A S E      R K R P      D S G      C S T       S K D T      K Y  Q>
       H L K      E K G       R T R A    V Q L       Q K T        P S T S>
      S I * K    K K A       G L G L     F N F       K R H        Q V  P>

490          500           510          520
                         *                          *
     TCGGTGTACG  TCATATCCGA   GGAGAAGGAC  GAGTGCGTCA  TCGCA
      S V Y     V I S E       E K D      E C V       I  A>
       R C T     S Y P         R R R T   S A S       S>
      V G V R   H I R         G E G      R V R H      R>
```

FIG. 10B

```
  1 TMNNLANCQREKDISVSIIGATQIXNTNKKADFXXGDXSSDKNGFQKARY  50
    ||||||||||||||:|:||||||||||| ||  ::     |||||: |.||
597 TMNNLANCQREKDISISVIGATQIKNTNKKVDFHSDN...SDKNGY.KVRY 643

51 PSVDYNLVQDLKGDDTAVRTSHSKRDTKCQSPGSSGRRRGPRPHSGXACC 100
    ||||||||::||.:|  .|:..|:|   :.||:   .:|.:    :::
644 PSVDYNLVHELKNED.SVKEEHGKCEAKCETYDSEAEEKSA........ 683

101 GPGSGGGTWGVSSWNHCSVSLPKCSHAFIVDFLYFPFSGEASERKRPDSG 150
                                  |::     |::.|||||||.
684 .............................VQLK....SSDTSERKRPDSV 700

151 CSTSKDTKYQSVYVISEEKDECVIA 175
    :|||||||||||||||||||||:||
701 YSTSKDTKYQSVYVISEEKDECIIA 725
```

FIG.11

```
         10         20         30         40         50         60
    *    *     *    *     *    *     *    *     *    *     *    *
CATTGGGTAC GGGCCCCCCT CGAGGTCGAC GGTATCGATA AGCTTGATAT CGAATTCCGG
         70         80         90        100        110        120
    *    *     *    *     *    *     *    *     *    *     *    *
CTTCACCTGG CCGGGCACCT TCTCTCTGAT TATTGAAGCT CTCCACACAG ATTCTCCTGA
        130        140        150        160        170        180
    *    *     *    *     *    *     *    *     *    *     *    *
TGACCTCGCA ACAGAAAACC CAGAAAGACT CATCAGCCGC CTGGCCACCC AGAGGCACCT
        190        200        210        220        230        240
    *    *     *    *     *    *     *    *     *    *     *    *
GACGGTGGGC GAGGAGTGGT CCCAGGACCT GCACAGCAGC GGCCGCACGG ACCTCAAGTA
        250        260        270        280        290        300
    *    *     *    *     *    *     *    *     *    *     *    *
CTCCTACCGC TTCGTGTGTC ACCAACACTA CTACGGAGAG GGCTGCTCCG TTTTCTGCCG
        310        320        330        340        350        360
    *    *     *    *     *    *     *    *     *    *     *    *
TCCCCGGGAC GATGCCTTCG GCCACTTCAC CTGTGGGGAG CGTGGGGAGA AAGTGTGCAA
        370        380        390        400        410        420
    *    *     *    *     *    *     *    *     *    *     *    *
CCCTGGCTCG AAAGGGCCCT ACTGCACAGA GCCGATCTGC CTGCCTGGAT GTGATGAGCA
        430        440        450        460        470        480
    *    *     *    *     *    *     *    *     *    *     *    *
GCATGGATTT TGTGACAAAC CAGGGGAATG CAAGTGCAGA GTGGGCTGGC AGGGCCGGTA
        490        500        510        520        530        540
    *    *     *    *     *    *     *    *     *    *     *    *
GTGTGACGAG TGTATCCGCT ATCCAGGCTG TCTCCATGGC ACCTGCCAGC AGCCCTGGCA
        550        560        570        580        590        600
    *    *     *    *     *    *     *    *     *    *     *    *
GTGCAACTGC CAGGAAGGNT GGGGGGGCCT TTTCTGCAAC CAGGACCTGA ACTACTGCAC
        610        620        630        640        650        660
    *    *     *    *     *    *     *    *     *    *     *    *
ACACCATAAG CCCTGCAAGA ATGGAGCCAC CTGCAACAAA CACGGGCCAG GGGGAGCTAC
        670        680        690        700        710        720
    *    *     *    *     *    *     *    *     *    *     *    *
ACTTGGTCTT TGGCCGGNCT GGGGTACANA GGGTGCCACC TGCGAAGCTT GGGGATTGGA
        730        740        750        760        770        780
    *    *     *    *     *    *     *    *     *    *     *    *
CGAGTTGTTG ACCCCAGCCC TTGGTAAGAA CGGAGGGAGC TTGACGGATC TTCGGAGAAC
        790        800        810        820        830        840
    *    *     *    *     *    *     *    *     *    *     *    *
AGCTACTCCT GTACCTGCCC ACCCGGCTTC TACGGCAAAA TCTGTGAATT GAGTGCCATG
        850        860        870        880        890        900
    *    *     *    *     *    *     *    *     *    *     *    *
ACCTGTGCGG ACGGCCCTTG CTTTAACGGG GGTCGGTGCT CAGACAGCCC CGATGGAGGG
```

FIG. 12A1

```
         910        920        930        940        950        960
       *   *      *   *      *   *      *   *      *   *      *   *
     TACAGCTGCC GCTGCCCCGT GGGCTACTCC GGCTTCAACT GTGAGAAGAA AATTGACTAC
         970        980        990       1000       1010       1020
       *   *      *   *      *   *      *   *      *   *      *   *
     TGCAGCTCTT CACCCTGTTC TAATGGTGCC AAGTGTGTGG ACCTCGGTGA TGCCTACCTG
        1030       1040       1050       1060       1070       1080
       *   *      *   *      *   *      *   *      *   *      *   *
     TGCCGCTGCC AGGCCGGCTT CTCGGGGAGG CACTGTGACG ACAACGTGGA CGACTGCGCC
        1090       1100       1110       1120       1130       1140
       *   *      *   *      *   *      *   *      *   *      *   *
     TCCTCCCCGT GCGCCAACGG ACCTCGGTGA CGGGATGGCG TGAACGACTT CTCCTGCACC
        1150       1160       1170       1180       1190       1200
       *   *      *   *      *   *      *   *      *   *      *   *
     TGCCCGCCTG GCTACACGGG CAGGAACTGC AGTGCCCCCG CCAGCACCTG CGAGCACGCA
        1210       1220       1230       1240       1250       1260
       *   *      *   *      *   *      *   *      *   *      *   *
     CCCTGCCACA ATGGGGCCAC CTGCCACGAG AGGGGCCACC GCTATNTGTG CGAGCACGCA
        1270       1280       1290       1300       1310       1320
       *   *      *   *      *   *      *   *      *   *      *   *
     CGAAGCTACG GGGGTCCCAA CTCCCANTTC CTGCTCCCCC AAACTGCCCC CCCGGCCCCA
        1330       1340       1350       1360       1370       1380
       *   *      *   *      *   *      *   *      *   *      *   *
     CGGTGGTGGA AACTCCCCTA AAAAAACCTA AAAGGGCCGG GGGGGGCCCA TCCCCTTGGT
        1390       1400       1410       1420       1430       1440
       *   *      *   *      *   *      *   *      *   *      *   *
     GGACGTGTGC GCCGGGGTCA TCCTTGTCCT CATGCTGCTG CTGGGCTGTG CCGCTGTGGT
        1450       1460       1470       1480       1490       1500
       *   *      *   *      *   *      *   *      *   *      *   *
     GGTCTGCGTC CGGCTGAGGC TGCAGAAGCA CCGGCCCCCA GCCGACCCCT GNCGGGGGGA
        1510       1520       1530       1540       1550       1560
       *   *      *   *      *   *      *   *      *   *      *   *
     GACGGAGACC ATGAACAACC TGGNCAACTG CCAGCGTGAG AAGGACATCT CAGTCAGCAT
        1570       1580       1590       1600       1610       1620
       *   *      *   *      *   *      *   *      *   *      *   *
     CATCGGGGNC ACGCAGATCA AGAACACCAA CAAGAAGGCG GACTTCCACG GGACCACAG
        1630       1640       1650       1660       1670       1680
       *   *      *   *      *   *      *   *      *   *      *   *
     NGCCGACAAG AATGGCTTCA AGGCCCGCTA CCCAGNGGTG GACTATAACC TCGTGCAGGA
        1690       1700       1710       1720       1730       1740
       *   *      *   *      *   *      *   *      *   *      *   *
     CCTCAAGGGT GACGACACCG CCGTCAGCCA CGCGCACAGC AAGCGTGACA CCAAGTGNCA
        1750       1760       1770       1780       1790       1800
       *   *      *   *      *   *      *   *      *   *      *   *
     GCCCCAGGGC TCCTCAGGGG AGGAGAAGGG GACCCCCGAC CCACACTCAG GGGGTGGAGG
```

FIG. 12A2

```
          1810       1820       1830       1840       1850       1860
         *    *    *    *    *    *    *    *    *    *    *    *
     AAGCATCTTG AAAGAAAAAG GCCGGACTTC GGGCTTGTTC AACTTTCAAA AGACAANCAA
          1870       1880       1890       1900       1910       1920
         *    *    *    *    *    *    *    *    *    *    *    *
     NGTACAAGTC GGTGTNCGTC ATTTCCGNAG GAGGAAGGNT GACTGCGTCA TAGGAANTTG
          1930       1940       1950       1960       1970       1980
         *    *    *    *    *    *    *    *    *    *    *    *
     AGGTNGTAAA NTGGNAGTTG ANNTTGGAAA GNNNTCCCCG GATTCCGNTT TCAAAGTTTT
     T
```

FIG. 12A3

```
              10         20         30         40         50         60
               *          *          *          *          *          * a.a.no.
         CATTGGGTAC GGGCCCCCCT CGAGGTCGAC GGTATCGATA AGCTTGATAT CGAATTCCGG
          H  W  V  R  A  P  L  E  V  D  G  I  D  K  L  D  I  E  F  R>   20
          I  G  Y  G  P  P  S  R  S  T  V  S  I  S  L  I  S  N  S  G>   20
          L  G  T  G  P  P  R  G  R  R  Y  R  *  A  *  Y  R  I  P>      19

70         80         90        100        110        120
               *          *          *          *          *          *
         CTTCACCTGG CCGGGCACCT TCTCTCTGAT TATTGAAGCT CTCCACACAG ATTCTCCTGA
          L  H  L  A  G  H  L  L  S  D  Y  *  S  S  P  H  R  F  S  *>   40
          F  T  W  P  G  T  F  S  L  I  I  E  A  L  H  T  D  S  P  D>   40
          A  S  P  G  R  A  P  S  L  *  L  L  K  L  S  T  Q  I  L  L>   39

130        140        150        160        170        180
               *          *          *          *          *          *
         TGACCTCGCA ACAGAAAACC CAGAAAGACT CATCAGCCGC CTGGCCACCC AGAGGCACCT
          *  P  R  N  K  P  R  K  T  H  Q  P  P  G  H  P  E  A  P>      60
          D  L  A  T  E  N  P  E  R  L  I  S  R  L  A  T  Q  R  H  L>   60
          M  T  S  Q  K  T  Q  K  D  S  S  A  A  W  P  P  R  G  T>      59

190        200        210        220        230        240
               *          *          *          *          *          *
         GACGGTGGGC GAGGAGTGGT CCCAGGACCT GCACAGCAGC GGCCGCACGG ACCTCAAGTA
          D  G  G  R  G  V  V  P  G  P  A  Q  Q  R  P  H  G  P  Q  V>   80
          T  V  G  E  E  W  S  Q  D  L  H  S  S  G  R  T  D  L  K  Y>   80
          *  R  W  A  R  S  G  P  R  T  C  T  A  A  A  A  R  T  S  S>   79

250        260        270        280        290        300
               *          *          *          *          *          *
         CTCCTACCGC TTCGTGTGTG ACGAACACTA CTACGGAGAG GGCTGCTCCG TTTTCTGCCG
          L  L  P  L  R  V  *  R  T  L  L  R  R  G  L  L  R  F  L  P>  100
          S  Y  R  F  V  C  D  E  H  Y  Y  G  E  G  C  S  V  F  C  R>  100
          T  P  T  A  S  C  V  T  N  T  T  T  E  R  A  A  P  F  S  A>   99

310        320        330        340        350        360
               *          *          *          *          *          *
         TCCCCGGGAC GATGCCTTCG GCCACTTCAC CTGTGGGGAG CGTGGGGAGA AAGTGTGCAA
          S  P  G  R  C  L  R  P  L  H  L  W  G  A  W  G  E  S  V  Q>  120
          P  R  D  D  A  F  G  H  F  T  C  G  E  R  G  E  K  V  C  N>  120
          V  P  G  T  M  P  S  A  T  S  P  V  C  S  V  G  R  K  C  A>  119
```

FIG.12B1

```
         370        380        390        400        410        420
          *    *    *    *    *    *    *    *    *    *    *    *
         CCCTGGCTGG AAAGGGCCCT ACTGCACAGA GCCGATCTGC CTGCCTGGAT GTGATGAGCA
           P  W  L   E  R  A  L   L  H  R   A  D  L   P  A  W  M   *  *  A>  140
          ┌─────────────────────────────────────────────────────────────┐
          │ P  G  W   K  G  P   Y  C  T  E   P  I  C   L  P  G   C  D  E  Q>│ 140
          └─────────────────────────────────────────────────────────────┘
           T  L  A  G   K  G  P   T  A  Q   S  R  S   A  C  L   D  V  M  S>  139

430        440        450        460        470        480
          *    *    *    *    *    *    *    *    *    *    *    *
         GCATGGATTT TGTGACAAAC CAGCCCAATG CAAGTGCAGA GTGGGCTGGC AGGGCCGGTA
           A  W  I  L   *  Q  T   R  G  M   Q  V  Q   S  G  L   A  G  P  V>  160
          ┌─────────────────────────────────────────────────────────────┐
          │ H  G  F   C  D  K   P  G  E  C   K  C  R   V  G  W   Q  G  R  Y>│ 160
          └─────────────────────────────────────────────────────────────┘
           S  M  D  F   V  T  N   Q  G  N   A  S  A  E   W  A  G   R  A  G>  159

490        500        510        520        530        540
          *    *    *    *    *    *    *    *    *    *    *    *
         CTGTGACGAG TGTATCCGCT ATCCAGGCTG TCTCCATGGC ACCTGCCAGC AGCCCTGGCA
           L  *  R   V  Y  P  L   S  R  L   S  P  W   H  L  P   A  A  L  A>  180
          ┌─────────────────────────────────────────────────────────────┐
          │ C  D  E   C  I  R   Y  P  G  C   L  H  G   T  C  Q   Q  P  W  Q>│ 180
          └─────────────────────────────────────────────────────────────┘
           T  V  T  S   V  S  A   I  Q  A   V  S  M  A   P  A  S   S  P  G>  179

550        560        570        580        590        600
          *    *    *    *    *    *    *    *    *    *    *    *
         GTGCAACTGC CAGGAAGGNT GGGGGGGCCT TTTCTGCAAC CAGGACCTGA ACTACTGCAC
           V  Q  L   P  G  R  X   G  G  P   F  L  Q   P  G  P  E   L  L  H>  200
          ┌─────────────────────────────────────────────────────────────┐
          │ C  N  C   Q  E  G   W  G  L  F   C  N  Q   D  L  N   Y  C  T>│ 200
          └─────────────────────────────────────────────────────────────┘
           S  A  T  A   R  K  X   G  G  A   F  S  A  T   R  T  *   T  T  A>  199

610        620        630        640        650        660
          *    *    *    *    *    *    *    *    *    *    *    *
         ACACCATAAG CCCTGCAAGA ATCGAGCCAC CTGCAACAAA CACGGGCCAG GGGGAGCTAC
           T  P  *   A  L  Q  E   W  S  H   L  Q  Q   T  R  A  R   G ┌─────┐
                                                                      │ S  Y>│ 220
          ┌─────────────────────────────────────────────────┐        └─────┘
          │ H  H  K   P  C  K  N   G  A  T  C│ N  K  H  G  P   G  G  A  T>  220
          └─────────────────────────────────────────────────┘
           H  T  I  S   P  A  R   M  E  P  P  A  ┌─────────────┐
                                                  │ T  N  T  G  Q  G │  E  L>  219
                                                  └─────────────┘

670        680        690        700        710        720
          *    *    *    *    *    *    *    *    *    *    *    *
         ACTTGGTCTT TGGCCGGNCT GGGGTACANA GGGTGCCACC TGCGAAGCTT GGGGATTGGA
          ┌──┐
          │ T│ W  S  L   A  G  L   G  Y  X   G  C  H   L  R  S   L  G  I  G>  240
          └──┘
           L  G  L  W   P  X  W   G  T  X   G  A  T   C  E  A  W   G  L  D>  240
           H  L  V  F   G  R  X   C  V  X   R  V  P   P  A  K  L   G  D  W>  239
```

FIG. 12B2

```
          730        740        750        760        770        780
           *          *          *          *          *          *
      CGAGTTGTTG ACCCCAGCCC TTGGTAAGAA CGGAGGGAGC TTGACGGATC TTCGGAGAAC
       R  V  V  D  P  S  P  W  *  E  R  R  E  L  D  G  S  S  E  N >   260
        E  L  L  T  P  A  L  G  K  N  G  G  S  L  T  D  L  R  R  T>   260
         T  S  C  *  P  Q  P  L  V  R  T  E  Q  A  *  R  I  F  G  E>  259

790        800        810        820        830        840
           *          *          *          *          *          *
      AGCTACTCCT GTACCTGCCC ACCCGGCTTC TACGGCAAAA TCTGTGAATT GAGTGCCATG
       S  Y  S  C  T  C  P  P  G  F  Y  G  K  I  C  E  L  S  A  M >   280
        A  T  P  V  P  A  H  P  A  S  T  A  K  S  V  N  *  V  P  *>   280
         Q  L  L  L  Y  L  P  T  R  L  L  R  Q  N  L  *  I  E  C  H>  279

850        860        870        880        890        900
           *          *          *          *          *          *
      ACCTGTGCGG ACGGCCCTTG CTTTAACGGG GGTCGGTGCT CAGACAGCCC CGATGGAGGG
       T  C  A  D  G  P  C  F  N  G  G  R  C  S  D  S  P  D  G  G >   300
        P  V  R  T  A  L  A  L  T  G  V  G  A  Q  T  A  P  M  E  G>   300
         D  L  C  G  R  P  L  L  *  R  G  S  V  L  R  Q  P  R  W  R> 299

910        920        930        940        950        960
           *          *          *          *          *          *
      TACAGCTGCC GCTGCCCCGT GGGCTACTCC GGCTTCAACT GTGAGAAGAA AATTGACTAC
       Y  S  C  R  C  P  V  G  Y  S  G  F  N  C  E  K  K  I  D  Y >   320
        T  A  A  A  A  P  W  A  T  P  A  S  T  V  R  R  K  L  T  T>   320
         V  Q  L  P  L  P  R  G  L  L  R  L  Q  L  *  E  E  N  *  L> 319

970        980        990       1000       1010       1020
           *          *          *          *          *          *
      TGCAGCTCTT CACCCTGTTC TAATGGTGCC AAGTGTGTGG ACCTCGGTGA TGCCTACCTG
       C  S  S  S  P  C  S  N  G  A  K  C  V  D  L  G  D  A  Y  L >   340
        A  A  L  H  P  V  L  M  V  P  S  V  W  T  S  V  M  P  T  C>   340
         L  Q  L  F  T  L  F  *  W  C  Q  V  C  G  P  R  *  C  L  P> 339

1030       1040       1050       1060       1070       1080
           *          *          *          *          *          *
      TGCCGCTGCC AGGCCGGCTT CTCGGGGAGG CACTGTGACG ACAACGTGGA CGACTGCGCC
       C  R  C  Q  A  G  F  S  G  R  H  C  D  D  N  V  D  D  C  A >   360
        A  A  A  R  P  A  S  R  G  G  T  V  T  T  T  W  T  T  A  P>   360
         V  P  L  P  G  R  L  L  G  E  A  L  *  R  Q  R  G  R  L  R> 359
```

FIG.12B3

```
           1090       1100       1110       1120       1130       1140
             *    *     *    *     *    *     *    *     *    *     *    *
           TCCTCCCCGT GCGCCAACGG GGGCACCTGC CGGGATGGCG TGAACGACTT CTCCTGCACC
            S  S  P    C  A  N  G  G  T  C   R  D  G   V  N  D  F  S  C  T>   380
            P  P  R    A  P  T   G  A  P  A  G  M  A   *  T  T   S  P  A  P>  380
            L  L  P    V  R  Q  R  G  H  L   P  G  W  R  E  R  L  L  L  H>    379

1150       1160       1170       1180       1190       1200
             *    *     *    *     *    *     *    *     *    *     *    *
           TGCCCGCCTG GCTACACGGG CAGGAACTGC AGTGCCCCCG CCAGCAGGTG CGAGCACGCA
            C  P  P    G  Y  T  G  R  N  C   S  A  P   A  S  R   C  E  H  A>  400
            A  R  L   A  T  R   A  G  T  A   V  P  P   P  A  G   A  S  T  H>  400
            L  P  A  W  L  H  G  Q  E  L   Q  C  P  R  Q  Q  V   R  A  R>     399

1210       1220       1230       1240       1250       1260
             *    *     *    *     *    *     *    *     *    *     *    *
           CCCTGCCACA ATGGGGCCAC CTGCCACGAG AGGGGCCACC GCTATNTGTG CGAGTGTGCC
            P  C  H   N  G  A  T  C  H  E   R  G  H  R  Y  X      C  E  C  A> 420
            P  A  T   M  G  P   P  A  T  R  G  A  T   A  I  C    A  S  V  P>  420
            T  L  P  Q  W  G  H  L  P  R   E  G  P  P  L  F  V   R  V  C>     419

1270       1280       1290       1300       1310       1320
             *    *     *    *     *    *     *    *     *    *     *    *
           CGAAGCTACG GGGGTCCCAA CTGCCANTTC CTGCTCCCCG AAACTGCCCC CCCGGCCCCA
            R  S  Y   G  G  P   N  C  X      F  L  L  P  E   T  A  P  P  A  P> 440
            E  A  T   G  V  P   T  A  X      S  C  S  P   K  L  P   P  R  P  H> 440
            P  K  L  R  G  S  Q  L  P  X   P  A  P  R  N  C    P  P  G  P>    439

1330       1340       1350       1360       1370       1380
             *    *     *    *     *    *     *    *     *    *     *    *
           CGGTGGTGGA AACTCCCCTA AAAAAACCTA AAAGGGCCGG GGGGGGCCCA TCCCCTTGGT
            R  W  W    K  L  P   *  K  N  L   K  G  P   G  G  A  H  P  L  G>  460
               G  G  G  N  S  P   K  K  T   *  K  G  R  G  G  P   I  P  L  V> 460
            T   V  V   E  T  P  L  K  K  P  K  R  A  G  G  G  P   S  P  W>    459

1390       1400       1410       1420       1430       1440
             *    *     *    *     *    *     *    *     *    *     *    *
           GGACGTGTGC GCCGGGGTCA TCCTTGTCCT CATGCTGCTG CTGGGCTGTC CGCTGTGGT
            G  R  V   R  R  G  H  P  C  P   H  A  A   A  G  L   C  R  C  G>   480
            D  V  C   A  G  V   I  L  V  L  M   L  L  L  G  C  A  A  V  V>    480
            W  T  C   A  P  G   S  S  L  S   S  C  C  C  W  A  V  P  L  W>    479
```

FIG.12B4

```
              1450       1460       1470       1480       1490       1500
               *          *          *          *          *          *
          GGTCTGCGTC CGGCTGAGGC TGCAGAAGCA CCGGCCCCCA GCCGACCCCT GNCGGGGGGA
           G  L  R   P  A  E  A   A  E  A   P  A  P   S  R  P  L   X  G  C>  500
           V  C  V   R  L  R   L  Q  K  H   R  P  P   A  D  P   X   R  G  E> 500
           W  S  A  S  G  *   G  C  R  S   T  G  P   Q  P  T  P   X  G  G>  499

1510       1520       1530       1540       1550       1560
               *          *          *          *          *          *
          GACGGAGACC ATGAACAACC TGGNCAACTG CCAGCGTGAG AAGGACATCT CAGTCAGCAT
           D  C  D   H  E  Q  P   G   Q  L  P  A  *   E  G  H  L   S  Q  H>  520
           T  E  T   M  N  N   L  X   N  C  Q  R  E   K  D  I  S  V  S  I>  520
           R  R  R  P  *  T  T   W  X  T   A  S  V   R  R  T  S   Q  S  A>  519

1570       1580       1590       1600       1610       1620
               *          *          *          *          *          *
          CATCGGGGNC ACGCAGATCA AGAACACCAA CAAGAAGGCG GACTTCCACG GGACCACAG
           H  R  G   H  A  D  Q   E  H  Q   Q  E  G   G  L  P  R  G  P  Q>  540
            I  G  X   T  Q  I   K  N  T  N   K  K  A   D  F  H  G  D  H  X>  540
           S  S  G  X  R  R  S   R  T  P   T  R  R   T  S  T   G  T  T>  539

1630       1640       1650       1660       1670       1680
               *          *          *          *          *          *
          NGCCGACAAG AATGGCTTCA AGGCCCGCTA CCCAGNGGTG GACTATAACC TCGTGCAGGA
           X  R  Q   E  W  L  Q   G  P  L   P  X  G   G  L  *  P   R  A  G>  560
            A  D  K  N  G  F   K  A  R  Y  P   X   V  D  Y  N  L  V  Q  D>  560
           X  P  T  R  M  A  S   R  P  A  T  Q  X  W  T  I  T   S  C  R>  559

1690       1700       1710       1720       1730       1740
               *          *          *          *          *          *
          CCTCAAGGGT GACGACACCG CCGTCAGGGA CGCGCACAGC AAGCGTGACA CCAAGTGNCA
           P  Q  G   *  R  H  R   R  Q  G   R  A  Q  Q  A  *  H   Q  V   X>  580
            L  K  G  D  D  T   A  V  R  D   A  H  S   K  R  D  T  K   X   Q> 580
           T  S  R  V   T  T  P   P  S  G   T  R  T   A  S  V  T   P  S  X>  579

1750       1760       1770       1780       1790       1800
               *          *          *          *          *          *
          GCCCCAGGGC TCCTCAGGGG AGGAGAAGGG GACCCCCGAC CCACACTCAG GGGGTGGAGG
           A  P  G   L  L  R  G   G  E  G   D  P  R   P  T  L  R   G  W  R>  600
            P  Q  G   S  S  G   E  E  K  G   T  P   D  P  H  S   G  G   G  G> 600
           S  P  R  A  P  Q  G   R  R  R   G  P  P  T   H  T  Q   G  V  E>  599
```

FIG.12B5

```
              1810       1820       1830       1840       1850       1860
               *  *       *  *       *  *       *  *       *  *       *  *
            AAGCATCTTG AAAGAAAAAG GCCGGACTTC GGGCTTGTTC AACTTTCAAA AGACAANCAA
             K  H  L   E [R  K  R] P  D  F   G  L  V   Q  L [S  K  D] X  Q>    620
             S [I] L    K  E  K   G  R  T  [S] G  L   F  N  F   Q  K [T] X  X>  620
             E  A  S *  K  K  K   A  G  L   R  A  C  [S  T] F   K  R  Q  X>    619

1870       1880       1890       1900       1910       1920
               *  *       *  *       *  *       *  *       *  *       *  *
            NGTACAAGTC GGTGTNCGTC ATTTCCGNAG GAGGAAGGNT GACTGCGTCA TAGGAANTTG
             X  T  S   R  C  X   S  F  P  X  E  E  G   *  L  R   H  R  X  L>  640
             V  Q  V   G  V  R   H  F  R  R  R  K  X   D [C  V   I] G  X  *>  640
             X  Y  K   S  V  X   V  I  S  X  G  G  R   X  T  A   S  * E  X>   639

1930       1940       1950       1960       1970       1980
               *  *       *  *       *  *       *  *       *  *       *  *
            AGGTNGTAAA NTGGNAGTTG ANNTTGGAAA GNNNTCCCCC GATTCCCNTT TCAAAGTTTT
             R  X  *   X  G  S  *  X  W  K   X  X  P   G  F  R   F  Q  S  F>  660
             G  X  K   X  X  V   X  X  G  K  X  S  P   D  S  X   F  K  V  F>  660
            [E  V] V   X  W  X   L  X  L  E  X  X  P   R  I  P   X  S  K  F>  659
```

FIG.12B6

```
MOUSE DELTA DNA   GTCCAGCGGT ACCATGGGCC GTCGGAGCGC GCTAGCCCTT GCCGTGGTCT   50
HUMAN DELTA       ---------- ---------- ---------- ---------- ----------

CONSENSUS         GTCCAGCGGT ACCATGGGCC GTCGGAGCGC GCTAGCCCTT GCCGTGGTCT   50

MOUSE DELTA DNA   CTGCCCTGCT GTGCCAGGTC TGGAGCTCCG GCGTATTTGA GCTGAAGCTG   100
HUMAN DELTA       ---------- ---------- ---------- ---------- ----------

CONSENSUS         CTGCCCTGCT GTGCCAGGTC TGGAGCTCCG GCGTATTTGA GCTGAAGCTG   100

MOUSE DELTA DNA   CAGGAGTTCG TCAACAAGAA GGGGCTGCTG GGGAACCGCA ACTGCTGCCG   150
HUMAN DELTA       ---------- ---------- ---------- ---------- ----------

CONSENSUS         CAGGAGTTCG TCAACAAGAA GGGGCTGCTG GGGAACCGCA ACTGCTGCCG   150

MOUSE DELTA DNA   CGGGGGCTCT GGCCCGCCTT GCGCCTGCAG GACCTTCTTT CGCGTATGCC   200
HUMAN DELTA       ---------- ---------- ---------- ---------- ----------

CONSENSUS         CGGGGGCTCT GGCCCGCCTT GCGCCTGCAG GACCTTCTTT CGCGTATGCC   200

MOUSE DELTA DNA   TCAAGCACTA CCAGGCCAGC GTGTCACCGG AGCCACCCTG CACCTACGGC   250
HUMAN DELTA       ---------- ---------- ---------- ---------- ----------

CONSENSUS         TCAAGCACTA CCAGGCCAGC GTGTCACCGG AGCCACCCTG CACCTACGGC   250

MOUSE DELTA DNA   AGTGCTGTCA CGCCAGTGCT GGGTGTCGAC TCCTTCAGCC TGCCTGATGG   300
HUMAN DELTA       ---------- ---------- ---------- ---------- -----CATTG   5

CONSENSUS         AGTGCTGTCA CGCCAGTGCT GGGTGTCGAC TCCTTCAGCC TGCCTSATKG   300

MOUSE DELTA DNA   CGCAGGCATC GACCCG---G CCTTCAGCAA CCCCA--TCC GATTTC-CCC   343
HUMAN DELTA       GGTACGGCC CCCCTCGAGG TCGACGGTAT CGATAAGCTT GATATCGAAT     55

CONSENSUS         SGYASGSRYC SMCCYGAGG YCKWCRGYAW CSMYAAGYYY GATATCGMMY   350

MOUSE DELTA DNA   TTCGGCTTCA CCTGGCCAGG TACCTTCTCT CTGATCATTG AAGCCCTCCA   393
HUMAN DELTA       TCCGGCTTCA CCTGGCCGGG CACCTTCTCT CTGATTATTG AAGCTCTCCA   105

CONSENSUS         TYCGGCTTCA CCTGGCCRGG YACCTTCTCT CTGATYATTG AAGCYCTCCA   400

MOUSE DELTA DNA   TACAGACTCT CCGGATGACC TCGCAACAGA AACCCAGAA AGACTCATCA   443
HUMAN DELTA       CACAGATTCT CCTGATGACC TCGCAACAGA AACCCAGAAA AGACTCATCA   155

CONSENSUS         YACAGAYTCT CCYGATGACC TCGCAACAGA AACCCAGAA AGACTCATCA   450
```

FIG. 13A

| | | |
|---|---|---|
| MOUSE DELTA DNA | GCCGCCTGAC CACACAGAGG CACCTCACTG TGGGAGAAGA ATGGTCTCAG | 493 |
| HUMAN DELTA | GCCGCCTGGC CACCAGAGG CACCTGACCG TGGCCGAGGA GTGGTCCCAG | 205 |
| CONSENSUS | GCCGCCTGRC CACMCAGAGG CACCTSACKG TGGGMGARGA RTGGTCYCAG | 500 |
| MOUSE DELTA DNA | GACCTTCACA GTAGCGGCCG CACAGACCTC CGGTACTCTT ACCGCTTTGT | 543 |
| HUMAN DELTA | GACCTGCACA GCAGCGGCCG CACGGACCTC AAGTACTCCT ACCGCTTCGT | 255 |
| CONSENSUS | GACCTKCACA GYAGCGGCCG CACRGACCTC MRGTACTCYT ACCGSTTYGT | 550 |
| MOUSE DELTA DNA | GTGTGACGAG CACTACTACG GAGAAGGTTG CTCTGTCTTC TGCCGACCTC | 593 |
| HUMAN DELTA | GTGTGACGAA CACTACTACG GAGACGGCTG CTCCGTTTTC TGCCGTCCCC | 305 |
| CONSENSUS | GTGTGACGAR CACTACTACG GAGARGGYTG CTCYGTKTTC TGCCGMCCYC | 600 |
| MOUSE DELTA DNA | GGGATGACGC CTTTGGCCAC TTCACCTGCC GGGACAGAGG GGAGAAGATG | 643 |
| HUMAN DELTA | GGGACGATGC CTTCGGCCAC TTCACCTGTG GGAGCGTGG GGAGAAAGTG | 355 |
| CONSENSUS | GGGAYGAYGC CTTYGGCCAC TTCACCTGYG GGASMGWGG GGAGAARRTG | 650 |
| MOUSE DELTA DNA | TGCGACCCTG GCTGGAAAGG CCAGTACTGC GCTGACCCAA TCTGTCTGCC | 693 |
| HUMAN DELTA | TGCAACCCTG GCTGGAAAGG GCCCTACTGC ACAGAGCCGA TCTGCCTGCC | 405 |
| CONSENSUS | TGCRACCCTG GCTGGAAAGG SCMSTACTGC ACWGASCCRA TCTGYCTGCC | 700 |
| MOUSE DELTA DNA | AGGGTGTGAT GACCAACATG GATACTGTGA CAAACCAGGG GAGTGCAAGT | 743 |
| HUMAN DELTA | TGGATGTGAT GAGCAGCATG GATTTTGTGA CAAACCAGGG GAATGCAAGT | 455 |
| CONSENSUS | WGGRTGTGAT GASCARCATG GATWYTGTGA CAAACCAGGG GARTGCAAGT | 750 |
| MOUSE DELTA DNA | GCAGAGTTGG CTGGCAGGGC CGGTACTGCG ATGAGTGCAT CCGATACCCA | 793 |
| HUMAN DELTA | GCAGAGTGGG CTGGCAGGGC CGITACTGTG ACGAGTGTAT CCGCTATCCA | 505 |
| CONSENSUS | GCAGAGTKGG CTGGCAGGGC CGSTACTGYS AYGAGTGYAT CCGMTAYCCA | 800 |
| MOUSE DELTA DNA | GGTTGTCTCC ATGGCACCTG CCAGCAACCC TGGCAGTGTA ACTGCCAGGA | 843 |
| HUMAN DELTA | GCCTGTCTCC ATGGCACCTG CCAGCAGCCC TGGCAGTGCA ACTGCCAGGA | 555 |
| CONSENSUS | GGYTGTCTCC ATGGCACCTG CCAGCARCCC TGGCAGTGMA ACTGCCAGGA | 850 |
| MOUSE DELTA DNA | AGGCTGGGGG GGCCTTTTCT GCAACCAAGA CCTGAACTAC TGTACTCACC | 893 |
| HUMAN DELTA | AGGNTGGGGG GGCCTTTTCT GCAACCAGGA CCTGAACTAC TGCACACACC | 605 |
| CONSENSUS | AGGNTGGGGG GGCCTTTTCT GCAACCARGA CCTGAACTAC TGYACWCACC | 900 |

FIG.13B

| | | | | | | |
|---|---|---|---|---|---|---|
| MOUSE DELTA DNA | ATAAGCCGTG | CAGGAATGGA | GCCACCTGCA | CCAACACGG | GCCAGGGG A | 941 |
| HUMAN DELTA | ATAAGCCCTG | CAAGAATGGA | GCCACCTGCA | ACAAACACGG | GCCAGGGGCA | 655 |
| CONSENSUS | ATAAGCCSTG | CARGAATGGA | GCCACCTGCA | ACMAACACGG | GCCAGGGGSA | 950 |
| MOUSE DELTA DNA | GCTACACATG | TTCCT GCC | GACCTGGGT | ATACA GGTG | CCAACTGTG | 986 |
| HUMAN DELTA | GCTACACTTG | GTCTTTGCCC | GGNCTGGGT | ACANAGGGTG | CCACCTGCCA | 705 |
| CONSENSUS | GCTACACWTG | KTCYTTGCCC | GGNCYKGGGT | AYANAGGGTG | CCAMCTGYGA | 1000 |
| MOUSE DELTA DNA | AGCT GGAA | GTAGATGAG | TG TGCTCCT | AGCCCCT GC | AAGAACGGAG | 1031 |
| HUMAN DELTA | AGCTTGGGGA | TTGGACGAGT | TGTTGACCCC | AGCCCTTGGT | AAGAACGGAG | 755 |
| CONSENSUS | AGCTTGGGRA | KTRGAYGAGT | TGTTGMYCCY | AGCCCYTGGY | AAGAACGGAG | 1050 |
| MOUSE DELTA DNA | CGAGCTGCAC | GGACCTT G | AGGACACTT | CTCTTGCACC | TGCCCTCCCG | 1079 |
| HUMAN DELTA | CGAGCTTGAC | GGATCTTCGG | AGAACAGCTA | CTCCTGTACC | TGCCCACCCG | 805 |
| CONSENSUS | SGAGCTKSAC | GGAYCTTCGG | AGRACAGCTW | CTCYTGYACC | TGCCCWCCCG | 1100 |
| MOUSE DELTA DNA | GCTTCTATGG | CAAGGTCTGT | GAGCTGAGCG | CCATGACCTG | TGCAGATGGC | 1129 |
| HUMAN DELTA | GCTTCAACGG | CAAAATCTGT | GAATTGAGTG | CCATGACCTG | TGCGGACGGC | 855 |
| CONSENSUS | GCTTCTAYGG | CAARRTCTGT | GARYTGAGYG | CCATGACCTG | TGCRGAYGGC | 1150 |
| MOUSE DELTA DNA | CCTTGCTTCA | ATCGAGGACG | ATGTTCAGAT | AACCCTGACG | GAGGCTACAC | 1179 |
| HUMAN DELTA | CCTTGCTTTA | ACGGGGGTCG | GTGCTCAGAC | AGCCCCGATG | GAGGGTACAG | 905 |
| CONSENSUS | CCTTGCTTYA | AYGGRGGMCG | RTGYTCAGAY | ARCCCYGAYG | GAGGSTACAS | 1200 |
| MOUSE DELTA DNA | CTGCCATTGC | CCCTTGGGCT | TCTCTGGCTT | CAACTGTGAG | AAGAAGATGG | 1229 |
| HUMAN DELTA | CTGCCGCTGC | CCCGTGGGCT | ACTCCGGCTT | CAACTGTGAG | AAGAAAATTG | 955 |
| CONSENSUS | CTGCCRYTGC | CCCKTGGGCT | WCTCYGGCTT | CAACTGTGAG | AAGAARATKG | 1250 |
| MOUSE DELTA DNA | ATCTCTGCGG | CTCTTCCCCT | TGTTCTAACG | GTGCCAAGTG | TGTGGACCTC | 1279 |
| HUMAN DELTA | ACTACTGCAG | CTCTTCACCC | TGTTCTAATG | GTGCCAAGTG | TGTGGACCTC | 1005 |
| CONSENSUS | AYYWCTGCRG | CTCTTCMCCY | TGTTCTAAYG | GTGCCAAGTG | TGTGGACCTC | 1300 |
| MOUSE DELTA DNA | GGCAACTCTT | ACCTGTGCCG | CTGCCAGGCT | GGCTTCTCCG | GGAGGTACTG | 1329 |
| HUMAN DELTA | GGTGATGCCT | ACCTGTGCCG | CTGCCAGGCC | GGCTTCTCGG | GGAGGCACTG | 1055 |
| CONSENSUS | GGYRAYKCYT | ACCTGTGCCG | CTGCCAGGCY | GGCTTCTGSG | GGAGGYACTG | 1350 |
| MOUSE DELTA DNA | CGAGGACAAT | GTGGATGACT | GTGCCTCCTC | CCCGTGTGCA | AATGGGGGCA | 1379 |
| HUMAN DELTA | TGACGACAAC | GTGGACGACT | GCGCCTCCTC | CCCGTGCGCC | AACGGGGGCA | 1105 |
| CONSENSUS | YGASGACAAY | GTGGAYGACY | GYGCCTCCTC | CCCGTGYGCM | AAYGGGGGCA | 1400 |

FIG. 13C

```
MOUSE DELTA DNA  CCTGCCGGGA CAGTGTGAAC GACTTCTCCT GTACCTGCCC ACCTGGCTAC  1429
HUMAN DELTA     CCTGCCGGGA TGGCGTGAAC GACTTCTCCT GCACCTGCCC GCCTGGCTAC  1155

CONSENSUS       CCTGCCGGGA YRGYGTGAAC GACTTGTCCT GYACCTGCCC RCCYGGCTAC  1450

MOUSE DELTA DNA ACGGGCAAGA ACTGCAGCGC CCCTGTCAGC AGGTGTGAGC ATGCACCCTG  1479
HUMAN DELTA     ACGGGCAGGA ACTGCAGTGC CCCCGCCAGC AGGTGCGAGC ACGCACCCTG  1205

CONSENSUS       ACGGGCARGA ACTGCAGYGC CCCYGYCAGC AGGTGYGAGC AYGCACCCTG  1500

MOUSE DELTA DNA CCATAATGGG GCCACCTGCC ACCAGAGGGG CCAGCGCTAC ATGTGTGAGT  1529
HUMAN DELTA     CCACAATGGG GCCACCTGCC ACGAGAGGGG CCACCGCTAT TTGTGCGAGT  1255

CONSENSUS       CCAYAATGGG GCCACCTGCC ACSAGAGGGG CCASCGCTAY WTGTGYGAGT  1550

MOUSE DELTA DNA GCGCCCAGGG CTATGGCGGC CCCAACTGCC AGTTTCTGCT CCCTGHAGCC  1578
HUMAN DELTA     GTGCCCGAAG CTACGGGGGT CCCAACTGCC ANTTCCTGCT CCCCGAAACT  1305

CONSENSUS       GYGCCCRRRG CTAYGGSGGY CCCAACTGCC ANTTYCTGCT CCCYGHARCY  1600

MOUSE DELTA DNA -ACCACCAGG GCCCATGGTG GTGG-ACCTC AGTGAGAGGC ATAT-GGAGA  1625
HUMAN DELTA     GCCCCCCCGG CCCCACGGTG GTGGAAACTC CCCTAAAAAA ACCTAAAACG  1355

CONSENSUS       GMCCMCCMGG SCCCAYGGTG GTGGAAMCTC MSYKARARRM AYMTARRAGR  1650

MOUSE DELTA DNA GCCAGGGCGG GCCCTTCCCC TGGGTGGCCG TGTGTGCCGG GGTGGTGCTT  1675
HUMAN DELTA     GCCGGGGGGG GCCCATCCCC TTGGTGGACG TGTGCGCCGG GGTCATCCTT  1405

CONSENSUS       GCCRGGGSGG GCCCWTCCCC TKGGTGGMCG TGTGYGCCGG GGTSRTSCTT  1700

MOUSE DELTA DNA GTCCTCCTGC TGCTGCTGGG CTGTGCTGCT GTGGTGGTCT GCGTCCGGCT  1725
HUMAN DELTA     GTCCTCATGC TGCTGCTGGG CTGTGCCGCT GTGGTGGTCT GCGTCCGGCT  1455

CONSENSUS       GTCCTCMTGC TGCTGCTGGG CTGTGCYGCT GTGGTGGTCT GCGTCCGGCT  1750

MOUSE DELTA DNA GAAGCTACAG AAACACCAGC CTCCATCTGA ACCCTGTGGG GGAGAGACAG  1775
HUMAN DELTA     GAGGCTGCAG AAGCACCCGC CCCCATCCGA CCCCTGNCGG GGGAGACGG   1505

CONSENSUS       GARGCTRCAG AARCACCRGC CYCCASCYGA MCCCTGNSGG GGRGAGACRG  1800

MOUSE DELTA DNA AAACCATGAA CAACCTAGCC AATTGCCAGC GCGAGAAGGA CGTTTCTGTT  1825
HUMAN DELTA     AGACCATGAA CAACCTGGNC AACTGCCAGC GTGAGAAGGA CATCTCAGTC  1555

CONSENSUS       ARACCATGAA CAACCTRGNC AAYTGCCAGC GYGAGAAGGA CRTYTCWGTY  1850
```

FIG.13D

| | | |
|---|---|---|
| MOUSE DELTA DNA | AGCATCATTG GGGCTACCCA GATCAAGAAC ACCAACAAGA AGGCGGACTT | 1875 |
| HUMAN DELTA | AGCATCATCG GGGNCACGCA GATCAAGAAC ACCAACAAGA AGGCGGACTT | 1605 |
| CONSENSUS | AGCATCATYG GGGNYACSCA GATCAAGAAC ACCAACAAGA AGGCGGACTT | 1900 |
| MOUSE DELTA DNA | TCACGGGGAC CATGGAGCCA AGAAGAGCAG CTTTAAGGTC CGATACCCCA | 1925 |
| HUMAN DELTA | CCACGGGGAC CACAGNGCCG ACAAGAATGG CTTCAAGGCC CGCTACCCAG | 1655 |
| CONSENSUS | YCACGGGGAC CAYRGNGCCR ASAAGARYRG CTTYAAGGYC CGMTACCCMR | 1950 |
| MOUSE DELTA DNA | CTGTGGACTA TAACCTCGTT CGAGACCTCA AGGGAGATGA AGCCACGGTC | 1975 |
| HUMAN DELTA | NGGTGGACTA TAACCTCGTG CAGGACCTCA AGGGTGACGA CACCGCCGTC | 1705 |
| CONSENSUS | NKGTGGACTA TAACCTCGTK CRRGACCTCA AGGGWGAYGA MRCCRCSGTC | 2000 |
| MOUSE DELTA DNA | AGGGATACAC ACAGCAAACG TGACACCAAG TGCCAGTCAC AGAGCTCTGC | 2025 |
| HUMAN DELTA | AGGGACGCGC ACAGCAAGCG TGACACCAAG TGNCAGCCCC AGGGCTCCTC | 1755 |
| CONSENSUS | AGGGAYRCRC ACAGCAARCG TGACACCAAG TGNCAGYCMC AGRGCTCYKC | 2050 |
| MOUSE DELTA DNA | AGGAGAAGAG AA--GATCG CC--CCAACA CTTTA-GGGGT GG--GG-AGAT | 2067 |
| HUMAN DELTA | AGGGGAGGAG AAGGGGACCC CCGACCCACA CTCAGGGGGT GGAGGAAGCA | 1805 |
| CONSENSUS | AGGRGARGAG AAGGGGAYCS CCGACCMACA CTYAGGGGGT GGAGGAAGMW | 2100 |
| MOUSE DELTA DNA | TCCTGACAGA AAAAGGCCAG AGTCT-GTC TACTCTAC-T TCAAAGGAC- | 2113 |
| HUMAN DELTA | TCTTGAAAGA AAAAGGCCGC ACTTCGGCCT TGTTCAACTT TCAAAAGACA | 1855 |
| CONSENSUS | TCYTGAMAGA AAAAGGCCRG ASTTYGGCYY TRYTCWACTT TCAAARGACA | 2150 |
| MOUSE DELTA DNA | -ACCAAGTAC CAGTCGGTGT ATGTTCTGTC TGCAGAA--A AGGATGAGTG | 2160 |
| HUMAN DELTA | ANCAAGTAC AAGTCGGTGT NCGTCATTTC CCNAGGAGGA AGGNTGACTG | 1905 |
| CONSENSUS | ANCMAGTAC MAGTCGGTGT NYGTYMTKTC YGNAGRAGGA AGGNTGASTG | 2200 |
| MOUSE DELTA DNA | TGTTATA-GC GACTGAGGT- GTAAGATGGA AGCCATGTGG CAAAATTCCC | 2208 |
| HUMAN DELTA | CGTCATAGGA ANTTGAGGTN GTAAANTGGN AG--TTG- --ANNTT- | 1945 |
| CONSENSUS | YGTYATAGGM RNYTGAGCTN GTAARNTGGN AGCCATGTGG CAANNTTCCC | 2250 |
| MOUSE DELTA DNA | ATTTCTCTCA AATAAAATTC CAAGGATATA GCCCCGATGA ATGCTGCTGA | 2258 |
| HUMAN DELTA | ------GGA AAGNNN- TC CCCGGAT- -TCCGNT- --TTC- | 1972 |
| CONSENSUS | ATTTCTCKSA AAKNNNATTC CMMGGATATA GCYCCGNTGA ATGCTKCTGA | 2300 |

FIG.13E

```
MOUSE DELTA DNA  GAGAGGAAGG GAGAGGAAAC CCAGGGACTG CTGCTGAGAA CCAGGTTCAG  2308
HUMAN DELTA      ---------- ------AAA- --------G TTTTT----- ----------  1981

CONSENSUS        GAGAGGAAGG GAGAGGAAAC CCAGGGACTG YTKYTCAGAA CCAGGTTCAG  2350

MOUSE DELTA DNA  GCGAAGCTGG TTCTCTCAGA GTTAGCAGAG GCGCCCGACA CTGCCAGCCT  2358
HUMAN DELTA      ---------- ---------- ---------- ---------- ----------  1981

CONSENSUS        GCGAAGCTGG TTCTCTCAGA GTTAGCAGAG GCGCCCGACA CTGCCAGCCT  2400

MOUSE DELTA DNA  AGGCTTTGGC TGCCGCTGGA CTGCCTGCTG GTTGTTCCCA TTGCACTATG  2408
HUMAN DELTA      ---------- ---------- ---------- ---------- ----------  1981

CONSENSUS        AGGCTTTGGC TGCCGCTGGA CTGCCTGCTG GTTGTTCCCA TTGCACTATG  2450

MOUSE DELTA DNA  GACAGTTGCT TTGAAGAGTA TATATTTAAA TGGACGAGTG ACTTGATTCA  2458
HUMAN DELTA      ---------- ---------- ---------- ---------- ----------  1981

CONSENSUS        GACAGTTGCT TTGAAGAGTA TATATTTAAA TGGACGAGTG ACTTGATTCA  2500

MOUSE DELTA DNA  TATAGGAAGC ACGCACTGCC CACACGTCTA TCTTGGATTA CTATGAGCCA  2508
HUMAN DELTA      ---------- ---------- ---------- ---------- ----------  1981

CONSENSUS        TATAGGAAGC ACGCACTGCC CACACGTCTA TCTTGGATTA CTATGAGCCA  2550

MOUSE DELTA DNA  GTCTTTCCTT GAACTAGAAA CACAACTGCC TTTATTGTCC TTTTTGATAC  2558
HUMAN DELTA      ---------- ---------- ---------- ---------- ----------  1981

CONSENSUS        GTCTTTCCTT GAACTAGAAA CACAACTGCC TTTATTGTCC TTTTTGATAC  2600

MOUSE DELTA DNA  TGAGATGTGT TTTTTTTTTT CCTAGACGGG AAAAAGAAAA CGTGTGTTAT  2608
HUMAN DELTA      ---------- ---------- ---------- ---------- ----------  1981

CONSENSUS        TGAGATGTGT TTTTTTTTTT CCTAGACGGG AAAAAGAAAA CGTGTGTTAT  2650

MOUSE DELTA DNA  TTTTTGGGA TTTGTAAAAA TATTTTTCAT GATATCTGTA AAGCTTGAGT  2658
HUMAN DELTA      ---------- ---------- ---------- ---------- ----------  1981

CONSENSUS        TTTTTTGGGA TTTGTAAAAA TATTTTTCAT GATATCTGTA AAGCTTGAGT  2700

MOUSE DELTA DNA  ATTTTGTGAC GTTCATTTTT TTATAATTTA AATTTTGGTA AATATGTACA  2708
HUMAN DELTA      ---------- ---------- ---------- ---------- ----------  1981

CONSENSUS        ATTTTGTGAC GTTCATTTTT TTATAATTTA AATTTTGGTA AATATGTACA  2750
```

FIG.13F

| | | | | | | |
|---|---|---|---|---|---|---|
| MOUSE DELTA DNA | AAGGCACTTC | GGGTCTATGT | GACTATATTT | TTTTGTATAT | AAATGTATTT | 2758 |
| HUMAN DELTA | ---------- | ---------- | ---------- | ---------- | ---------- | 1981 |
| CONSENSUS | AAGGCACTTC | GGGTCTATGT | GACTATATTT | TTTTGTATAT | AAATGTATTT | 2800 |
| MOUSE DELTA DNA | ATGGAATATT | GTGCAAATGT | TATTTGAGTT | TTTTACTGTT | TTGTTAATGA | 2808 |
| HUMAN DELTA | ---------- | ---------- | ---------- | ---------- | ---------- | 1981 |
| CONSENSUS | ATGGAATATT | GTGCAAATGT | TATTTGAGTT | TTTTACTGTT | TTGTTAATGA | 2850 |
| MOUSE DELTA DNA | AGAAATTCAT | TTTAAAAATA | TTTTTCCAAA | ATAAATATAA | TGAACTACA | 2857 |
| HUMAN DELTA | ---------- | ---------- | ---------- | ---------- | ---------- | 1981 |
| CONSENSUS | AGAAATTCAT | TTTAAAAATA | TTTTTCCAAA | ATAAATATAA | TGAACTACA | 2899 |

NUCLEOTIDE AND PROTEIN SEQUENCES OF VERTEBRATE DELTA GENES AND METHODS BASED THEREON

The present application is a continuation application of application Ser. No. 09/783,931 filed Feb. 15, 2001 now U.S. Pat. No. 7,118,890, which is a divisional application of application Ser. No. 08/981,392, filed Apr. 7, 1998, now U.S. Pat. No. 6,262,025, which is the national stage of International Application No. PCT/US96/11178 filed Jun. 28, 1996, which claims the benefit of provisional Application Ser. No. 60/000,589 filed Jun. 28, 1995, which is incorporated by reference herein in its entirety.

1. INTRODUCTION

The present invention relates to vertebrate Delta genes and their encoded protein products, as well as derivatives and analogs thereof. Production of vertebrate Delta proteins, derivatives, and antibodies is also provided. The invention further relates to therapeutic compositions and methods of diagnosis and therapy.

2. BACKGROUND OF THE INVENTION

Genetic analyses in *Drosophila* have been extremely useful in dissecting the complexity of developmental pathways and identifying interacting loci. However, understanding the precise nature of the processes that underlie genetic interactions requires a knowledge of the protein products of the genes in question.

The vertebrate central nervous system is an intimate mixture of different cell types, almost all generated from the same source—the neurogenic epithelium that forms the neural plate and subsequently the neural tube. What are the mechanisms that control neurogenesis in this sheet of cells, directing some to become neurons while others remain non-neuronal? The answer is virtually unknown for vertebrates, but many of the cellular interactions and genes controlling cell fate decisions during neurogenesis have been well characterized in *Drosophila* (Campos-Ortega, 1993, J. Neurobiol. 24:1305-1327). Although the gross anatomical context of neurogenesis appears very different in insects and vertebrates, the possibility remains that, at a cellular level, similar events are occurring via conserved molecular mechanisms. Embryological, genetic and molecular evidence indicates that the early steps of ectodermal differentiation in *Drosophila* depend on cell interactions (Doe and Goodman, 1985, Dev. Biol. 111:206-219; Technau and Campos-Ortega, 1986, Dev. Biol. 195:445-454; Vassin et al., 1985, J. Neurogenet. 2:291-308; de la Concha et al., 1988, Genetics 118:499-508; Xu et al., 1990, Genes Dev. 4:464-475; Artavanis-Tsakonas, 1988, Trends Genet. 4:95-100). Mutational analyses reveal a small group of zygotically-acting genes, the so called neurogenic loci, which affect the choice of ectodermal cells between epidermal and neural pathways (Poulson, 1937, Proc. Natl. Acad. Sci. 23:133-137; Lehmann et al., 1983, Wilhelm Roux's Arch. Dev. Biol. 192:62-74; Jürgens et al., 1984, Wilhelm Roux's Arch. Dev. Biol. 193:283-295; Wieschaus et al., 1984, Wilhelm Roux's Arch. Dev. Biol. 193:296-307; Nüsslein-Volhard et al., 1984, Wilhelm Roux's Arch. Dev. Biol. 193:267-282). Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral -epidermal structures. This effect is due to the misrouting of epidermal precursor cells into a neuronal pathway, and implies that neurogenic gene function is necessary to divert cells within the neurogenic region from a neuronal fate to an epithelial fate.

Neural precursors arise in the *Drosophila* embryo from a neurogenic epithelium during successive waves of neurogenesis (Campos-Ortega & Hartenstein, 1985, The embryonic development of *Drosophila melanogaster* (Springer-Verlag, Berlin; New York); Doe, 1992, Development 116:855-863). The pattern of production of these cells is largely determined by the activity of the proneural and neurogenic genes. Proneural genes predispose clusters of cells to a neural fate (reviewed in Skeath & Carroll, 1994, Faseb J. 8:714-21), but only a subset of cells in a cluster become neural precursors. This restriction is due to the action of the neurogenic genes, which mediate lateral inhibition—a type of inhibitory cell signaling by which a cell committed to a neural fate forces its neighbors either to remain uncommitted or to enter a non-neural pathway (Artavanis-Tsakonas & Simpson, 1991, Trends Genet. 7:403-408; Doe & Goodman, 1985, Dev. Biol. 111:206-219). Mutations leading to a failure of lateral inhibition cause an overproduction of neurons—the "neurogenic" phenotype (Lehmann et al., 1981, Roux's Arch. Dev. Biol. 190:226-229; Lehmann et al., Roux's Arch. Dev. Biol. 192:62-74). In *Drosophila*, the inhibitory signal is delivered by a transmembrane protein encoded by the Delta neurogenic gene, which is displayed by the nascent neural cells (Heitzler & Simpson, 1991, Cell 64:1083-1092). Neighboring cells express a transmembrane receptor protein, encoded by the neurogenic gene Notch (Fortini & Artavanis-Tsakonas, 1993, Cell 75:1245-1247). Delta has been identified as a genetic unit capable of interacting with the Notch locus (Xu et al., 1990, Genes Dev. 4:464-475).

Mutational analyses also reveal that the action of the neurogenic genes is pleiotropic and is not limited solely to embryogenesis. For example, ommatidial, bristle and wing formation, which are known also to depend upon cell interactions, are affected by neurogenic mutations (Morgan et al., 1925, Bibliogr. Genet. 2:1-226; Welshons, 1956, Dros. Inf. Serv. 30:157-158; Preiss et al., 1988, EMBO J. 7:3917-3927; Shellenbarger and Mohler, 1978, Dev. Biol. 62:432-446; Technau and Campos-Ortega, 1986, Wilhelm Roux's Dev. Biol. 195:445-454; Tomlison and Ready, 1987, Dev. Biol. 120:366-376; Cagan and Ready, 1989, Genes Dev. 3:1099-1112). Neurogenic genes are also required for normal development of the muscles, gut, excretory and reproductive systems of the fly (Muskavitch, 1994, Dev. Biol. 166:415-430).

Both Notch and Delta are transmembrane proteins that span the membrane a single time (Wharton et al., 1985, Cell 43:567-581; Kidd and Young, 1986, Mol. Cell. Biol. 6:3094-3108; Vassin, et al., 1987, EMBO J. 6:3431-3440; Kopczynski, et al., 1988, Genes Dev. 2:1723-1735) and include multiple tandem EGF-like repeats in their extracellular domains (Muskavitch, 1994, Dev. Biol. 166:415-430). The Notch gene encodes a ~300 kd protein (we use "Notch" to denote this protein) with a large N-terminal extracellular domain that includes 36 epidermal growth factor (EGF)-like tandem repeats followed by three other cysteine-rich repeats, designated Notch/lin-12 repeats (Wharton, et al., 1985, Cell 43:567-581; Kidd and Young, 1986, Mol. Cell. Biol. 6:3094-3108; Yochem, et al., 1988, Nature 335:547-550). Molecular studies have lead to the suggestion that Notch and Delta constitute biochemically interacting elements of a cell communication mechanism involved in early developmental decisions (Fehon et al., 1990, Cell 61:523-534). Homologs are found in *Caenorhabditis elegans*, where the Notch-related gene lin-12 and the Delta-related gene lag-2 are also responsible for lateral inhibition (Sternberg, 1993, Current Biol.

3:763-765; Henderson et al., 1994, Development 120:2913-2924; Greenwald, 1994, Curr. Opin. Genet. Dev. 4:556-562). In vertebrates, several Notch homologs have also been identified (Kopan & Weintraub, 1993, J. Cell Biol. 121:631-641; Lardelli et al., 1994, Mech. Dev. 46:123-136; Lardelli & Lendahl, 1993, Exp. Cell Res. 204:364-372; Weinmaster et al., 1991, Development 113:199-205; Weinmaster et al., 1992, Development 116:931-941; Coffman et al., 1990, Science 249:1438-1441; Bierkamp & Campos-Ortega, 1993, Mech. Dev. 43:87-100), and they are expressed in many tissues and at many stages of development. Loss of Notch-1 leads to somite defects and embryonic death in mice (Swiatek et al., 1994, Genes Dev. 8:707-719; Conlon et al., Rossant, J. Development (J. Dev. 121:1533-1545), while constitutively active mutant forms of Notch-1 appear to inhibit cell differentiation in *Xenopus* and in cultured mammalian cells (Coffman et al., 1993, Cell 73:659-671; Kopan et al., 1994, Development 120:2385-2396; Nye et al., 1994, Development 120: 2421-2430).

The EGF-like motif has been found in a variety of proteins, including those involved in the blood clotting cascade (Furie and Furie, 1988, Cell 53: 505-518). In particular, this motif has been found in extracellular proteins such as the blood clotting factors IX and X (Rees et al., 1988, EMBO J. 7:2053-2061; Furie and Furie, 1988, Cell 53: 505-518), in other *Drosophila* genes (Knust et al., 1987 EMBO J. 761-766; Rothberg et al., 1988, Cell 55:1047-1059), and in some cell-surface receptor proteins, such as thrombomodulin (Suzuki et al., 1987, EMBO J. 6:1891-1897) and LDL receptor (Sudhof et al., 1985, Science 228:815-822). A protein binding site has been mapped to the EGF repeat domain in thrombomodulin and urokinase (Kurosawa et al., 1988, J. Biol. Chem 263: 5993-5996; Appella et al., 1987, J. Biol. Chem. 262:4437-4440).

Citation of references hereinabove shall not be construed as an admission that such references are prior art to the present invention.

3. SUMMARY OF THE INVENTION

The present invention relates to nucleotide sequences of vertebrate Delta genes (chick and mouse Delta, and related genes of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the Delta protein is a mammalian protein, preferably a human protein.

The invention relates to vertebrate Delta derivatives and analogs of the invention which are functionally active, i.e., they are capable of displaying one or more known functional activities associated with a full-length (wild-type) Delta protein. Such functional activities include but are not limited to antigenicity [ability to bind (or compete with Delta for binding) to an anti-Delta antibody], immunogenicity (ability to generate antibody which binds to Delta), ability to bind (or compete with Delta for binding) to Notch or other toporythmic proteins or fragments thereof ("adhesiveness"), ability to bind (or compete with Delta for binding) to a receptor for Delta. "Toporythmic proteins" as used herein, refers to the protein products of Notch, Delta, Serrate, Enhancer of split, and Deltex, as well as other members of this interacting set of genes which may be identified, e.g., by virtue of the ability of their gene sequences to hybridize, or their homology to Delta, Serrate, or Notch, or the ability of their genes to display phenotypic interactions or the ability of their protein products to interact biochemically.

The invention further relates to fragments (and derivatives and analogs thereof) of a vertebrate Delta that comprise one or more domains of the Delta protein, including but not limited to the intracellular domain, extracellular domain, transmembrane domain, DSL domain, domain amino-terminal to the DSL domain, or one or more EGF-like (homologous) repeats of a Delta protein, or any combination of the foregoing.

Antibodies to a vertebrate Delta, its derivatives and analogs, are additionally provided.

Methods of production of the vertebrate Delta proteins, derivatives and analogs, e.g., by recombinant means, are also provided.

The present invention also relates to therapeutic and diagnostic methods and compositions based on Delta proteins and nucleic acids. The invention provides for treatment of disorders of cell fate or differentiation by administration of a therapeutic compound of the invention. Such therapeutic compounds (termed herein "Therapeutics") include: Delta proteins and analogs and derivatives (including fragments) thereof; antibodies thereto; nucleic acids encoding the Delta proteins, analogs, or derivatives; and Delta antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or Delta function (hereinafter "Antagonist Therapeutics") are administered for therapeutic effect. In another embodiment, Therapeutics which promote Notch and/or Delta function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Delta protein can be diagnosed by detecting such levels, as described more fully infra.

In a preferred aspect, a Therapeutic of the invention is a protein consisting of at least a fragment (termed herein "adhesive fragment") of Delta which mediates binding to a Notch protein or a fragment thereof.

3.1. DEFINITIONS

As used herein, underscoring or italicizing the name of a gene shall indicate the gene, in contrast to its encoded protein product which is indicated by the name of the gene in the absence of any underscoring. For example, "*Delta*" shall mean the Delta gene, whereas "Delta" shall indicate the protein product of the Delta gene.

4. DESCRIPTION OF THE FIGURES

Figure 3A:
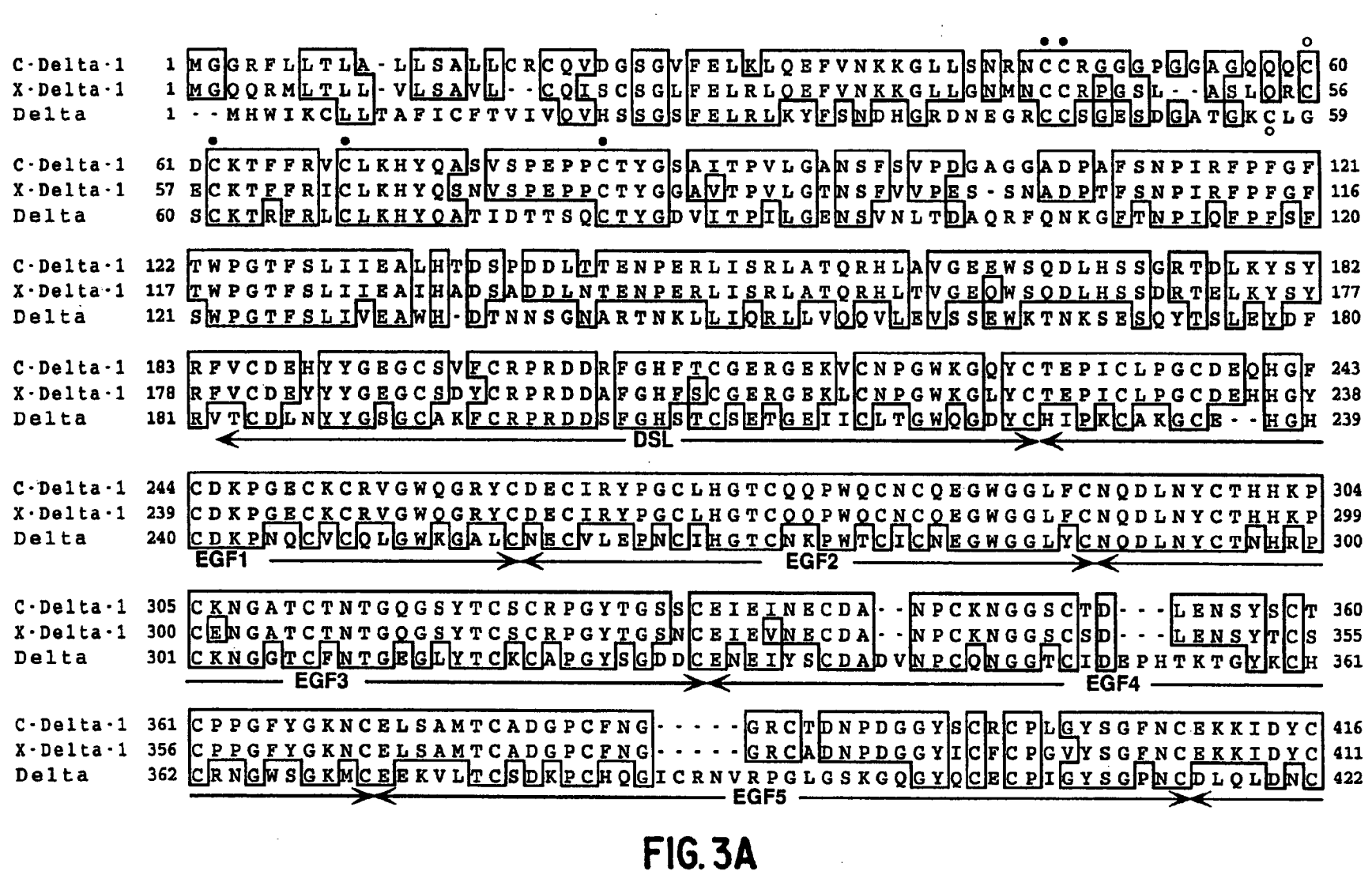

FIGS. 1A1-1A3-1B1-1B2. FIGS. 1A1-1A3. The DNA sequence of chick Delta (C-Delta-1) (SEQ ID NO:1). FIGS. 1B1-1B2. The DNA sequence of an alternatively spliced chick Delta (C-Delta-1) (SEQ ID NO:3).

FIG. 2. The predicted amino acid sequence of chick Delta (C-Delta-1) (SEQ ID NO:2).

Figure 3B:
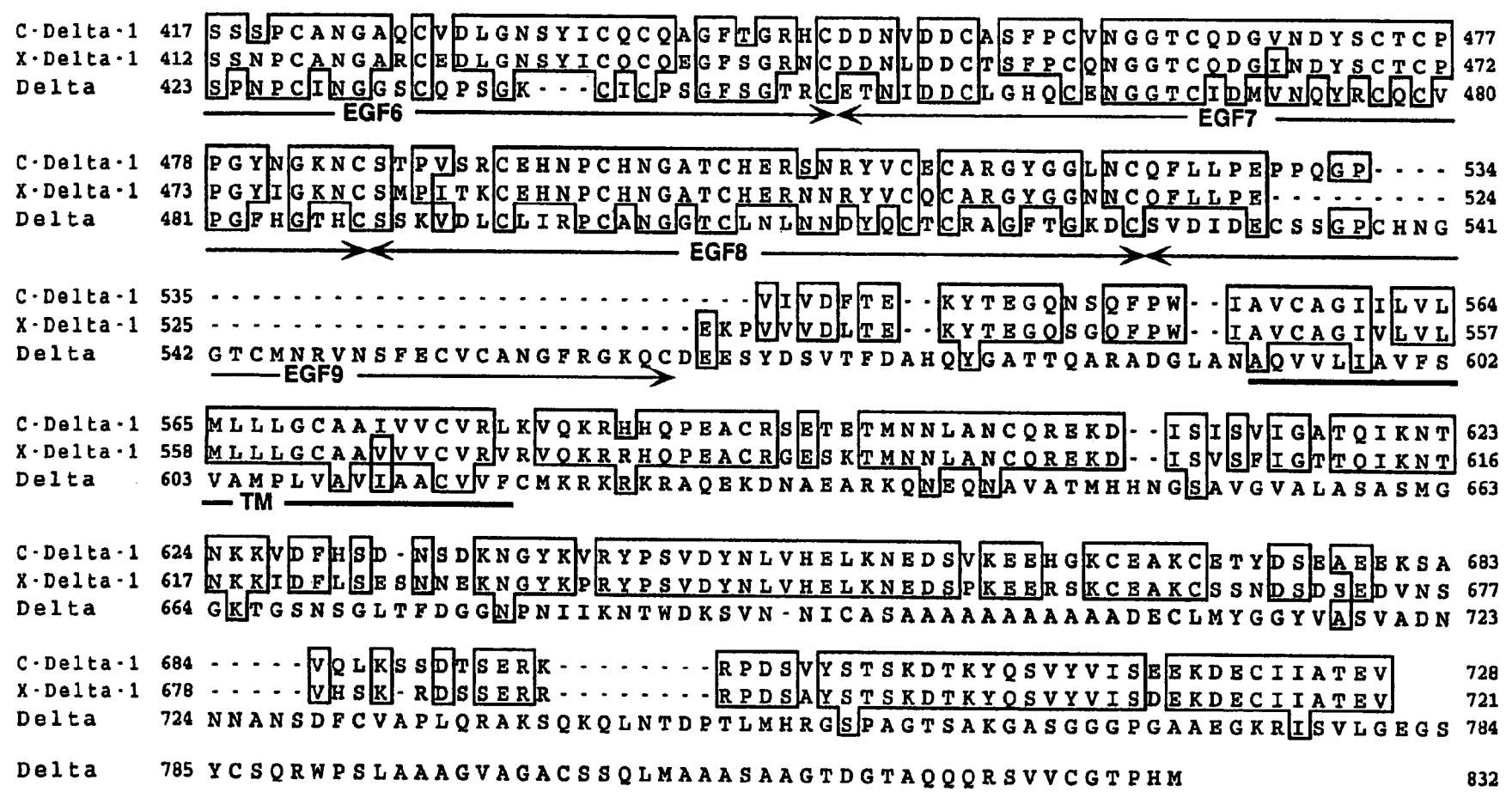

FIGS. 3A-3B. Predicted amino acid sequence of C-Delta-1 (SEQ ID NO:2), aligned with that of X-Delta-1 (*Xenopus* Delta; SEQ ID NO:5) and *Drosophila* Delta (SEQ ID NO:6) and, indicating the conserved domain structures: EGF repeats, DSL domain, and transmembrane domain (TM).

Conserved amino acids are boxed, and denote aligned and non-aligned N-terminal cysteine residues, respectively. Although the intracellular domains of C-Delta-1 and X-Delta-1 closely resemble each other, they show no significant homology to the corresponding part of *Drosophila* Delta.

FIG. 4. Alignment of DSL domains from C-Delta-1 (SEQ ID NO:2), *Drosophila* Delta (SEQ ID NO:6) (Vässin et al., 1987, EMBO J. 6:3431-3440; Kopczynski et al., 1988, Genes Dev. 2:1723-1735), *Drosophila* Serrate (SEQ ID NO:7) (Fleming et al., 1990, Genes Dev. 4:2188-2201; Thomas et al., 1991, Development 111:749-761), C-Serrate-1 (SEQ ID NO:8) (Myat, Henrique, Ish-Horowicz and Lewis, in preparation), Apx-1 (SEQ ID NO:9) (Mello et al., 1994, Cell 77:95-106) and Lag-2 (SEQ ID NO:10) (Henderson et al., 1994, Development 120:2913-2924; Tax et al., 1994, Nature 368: 150-154), showing the conserved Cysteine spacings, the amino acids that are conserved between presumed ligands for Notch-like proteins in *Drosophila* and vertebrates, and those that are further conserved in *C. elegans* ligands (boxes).

Figure 5B:
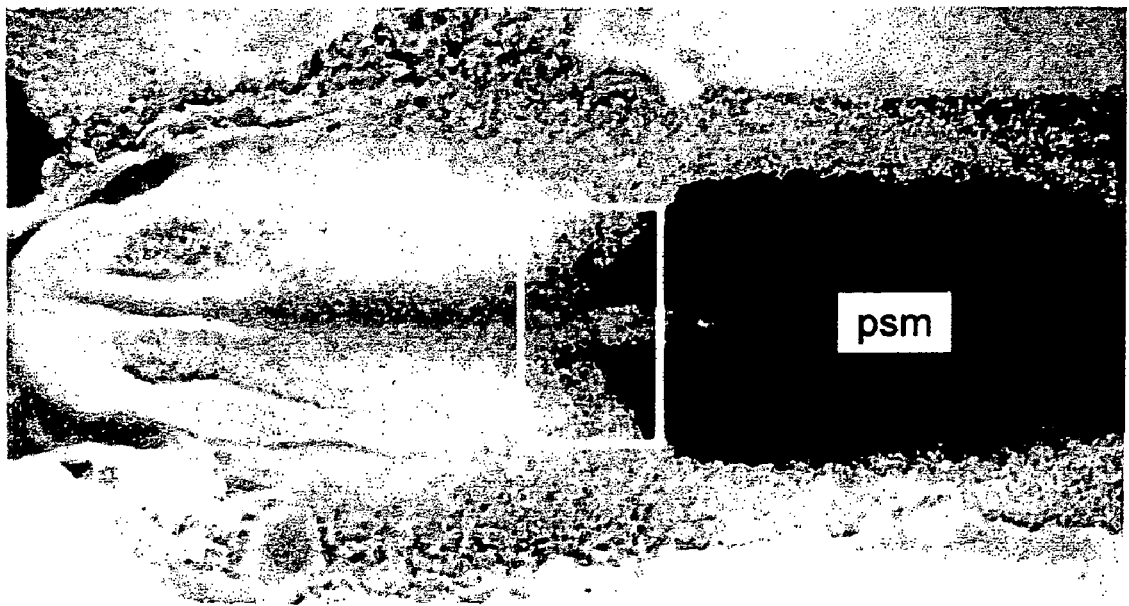
Figure 5C:
Figure 5D:
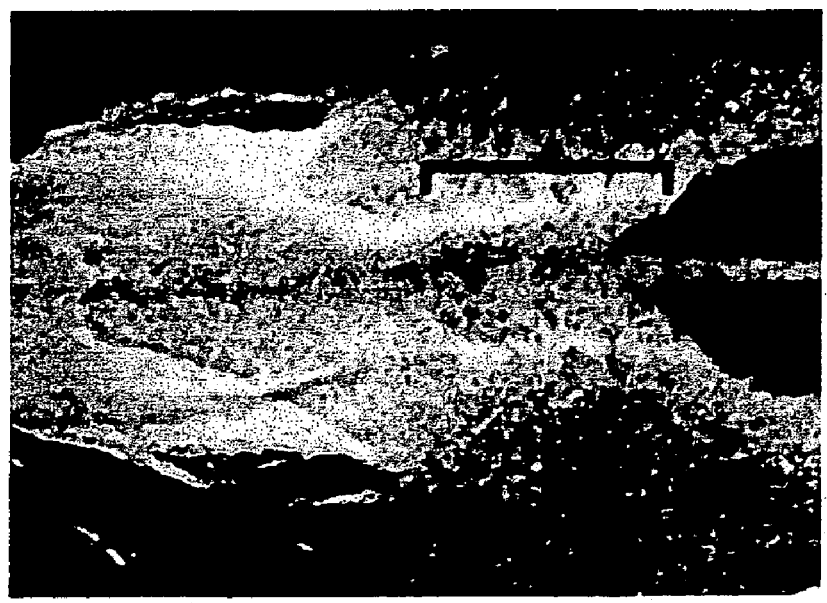
Figure 5E:
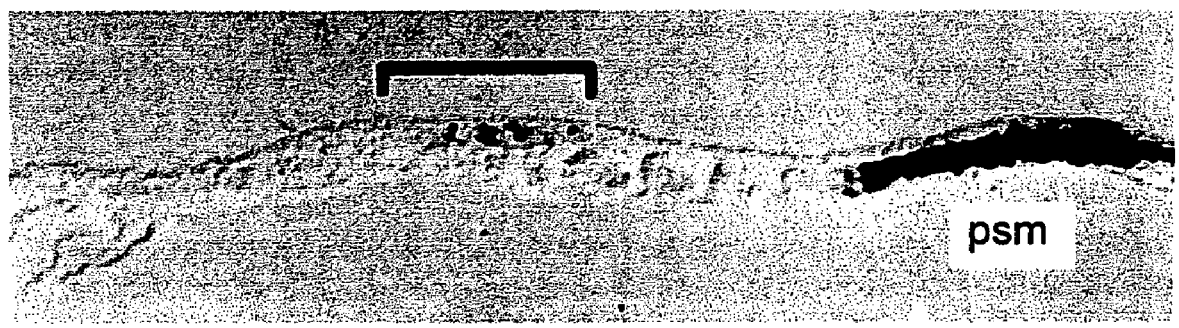

FIGS. 5A-5E. C-Delta-1 and C-Notch-1 expression correlate with onset of neurogenesis in the one-day (E1) neural plate. Anterior is to the left. Wholemount in situ hybridization specimens are shown in FIGS. 5a-d; 5e is a section. FIG. 5a, At stage 7, C-Notch-1 is expressed throughout most of the neural plate and part of the underlying presomitic mesoderm. FIG. 5b, C-Delta-1 at stage 7 is already detectable in the neural plate, in the future posterior hindbrain, just anterior to the first somite (white box). The posterior end of this neural domain is roughly level with the anterior margin of a domain of very strong expression in the underlying presomitic mesoderm (psm). Earlier expression in the neural plate may occur and be masked by expression in the underlying mesoderm (unpublished results). FIG. 5c, Higher magnification view of the area boxed in 5b, showing scattered cells in the neural plate expressing C-Delta-1. FIG. 5d, At stage 8, C-Delta-1 expression in the neural plate extends posteriorly as the neural plate develops. The domain of labelled neural plate cells visible in this photograph (bracketed) continues posteriorly over the presomitic mesoderm. FIG. 5e, Parasagittal section of a stage 8 embryo showing that C-Delta-1 is expressed in scattered cells of the neural plate (dorsal layer of tissue; bracketed), and broadly in the presomitic mesoderm (ventral layer). The plane of section is slightly oblique, missing the posterior part of the neural plate domain (cf. 5d).

Figure 6A:
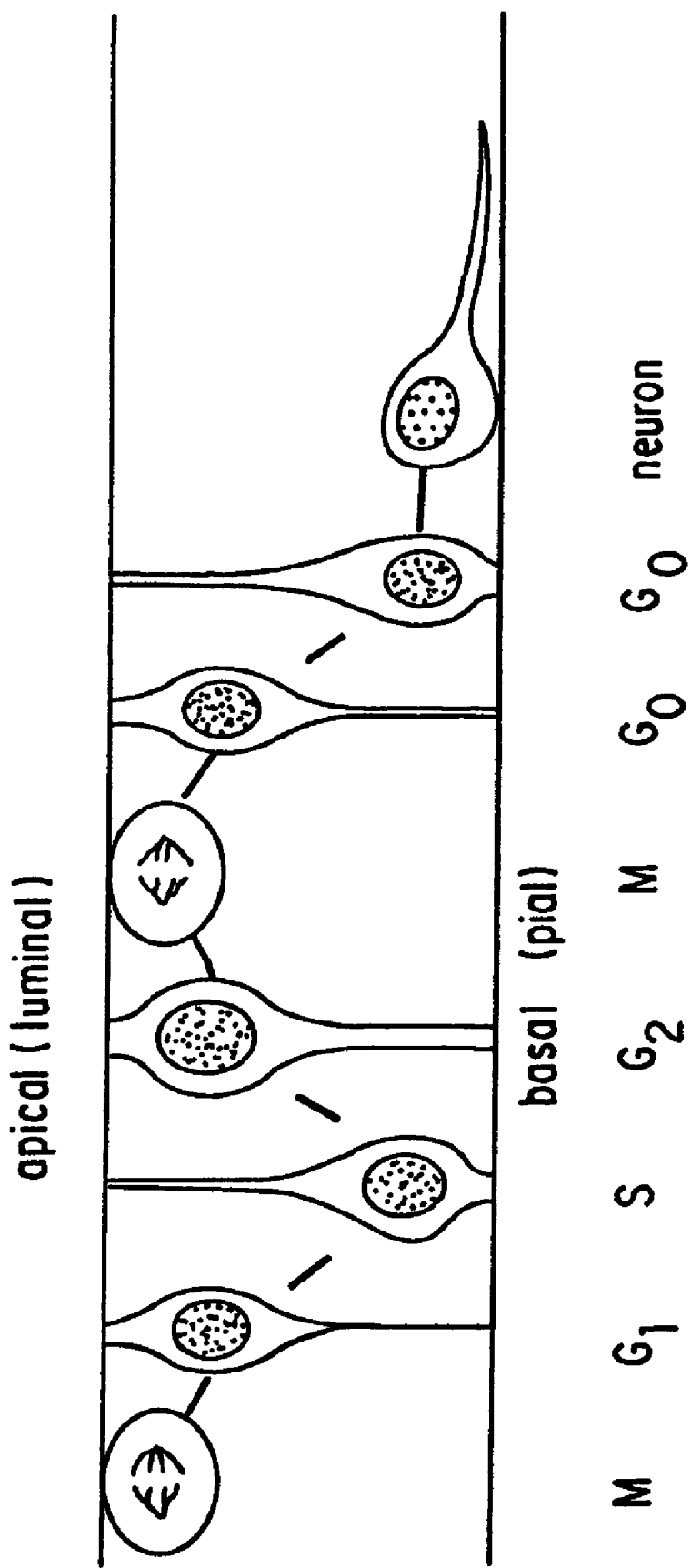
Figure 6B:
Figure 6C:

FIGS. 6A-6C. C-Delta-1-expressing cells do not incorporate BrdU. Of 612 C-Delta-1+ cells, 581 were BrdU− (76 sections; 6 embryos). FIG. 6a, Diagram showing how phase in the cell cycle is related to apico-basal position of the nucleus for cells in the neuroepithelium; S-phase nuclei lie basally (Fujita, 1963, J. Comp. Neurol. 120:37-42; Biffo et al., 1992, Histochem. Cytochem. 40:535-540). Nuclei are indicated by shading. FIG. 6b, Section through the neural tube of a stage 9 embryo labelled for 2 h with BrdU showing C-Delta-1-expressing cells (dark on blue background) and BrdU-labelled nuclei (pink). Labelled nuclei are predominantly basal, where DNA synthesis occurs, yet basal C-Delta-1-expressing cells are unlabelled. FIG. 6c, Section through a stage 9 embryo incubated for 4 h: many labelled nuclei have exited S-phase and have moved towards the lumen, but C-Delta-1-expressing cells are still basal and not labelled with BrdU.

FIGS. 7A-7B. The DNA sequence of mouse Delta (M-Delta-1) (SEQ ID NO:11).

FIG. 8. The predicted amino acid sequence of the mouse Delta (M-Delta-1) (SEQ ID NO:12).

FIGS. 9A-9B. An alignment of the predicted amino acid sequence of mouse M-Delta-1 (SEQ ID NO:12) with the chick C-Delta-1 (SEQ ID NO:2) which shows their extensive amino acid sequence identity. Identical amino acids are boxed. The consensus sequence between the two genes is at the bottom (SEQ ID NO:13).

FIGS. 10A-10B. The DNA sequence of a PCR amplified fragment of human Delta (H-Delta-1) (SEQ ID NO:14) and the predicted amino acid sequences using the three available open reading frames, 2nd line (SEQ ID NOS:15-17), 3rd line (SEQ ID NO:18), 4th line (SEQ ID NOS:19-22).

FIG. 11. An alignment of human H-Delta-1 (top line) and chick C-Delta-1 (bottom line). The predicted amino acid sequence of human Delta (SEQ ID NO:23) is shown in the top line. The sequence of human Delta was determined by "eye", in which the sequence of the appropriate reading frame was determined by maximizing homology with C-Delta-1. No single reading frame shown in FIGS. 10A-10B gave the correct sequence due to errors in the DNA sequence of FIGS. 10A-10B that caused reading frameshifts.

FIGS. 12A1-12A3-12B1-12B6. FIGS. 12A1-12A3 present the contig DNA sequence of human Delta (H-Delta-1) (SEQ ID NO:26) from clone HD1 18. FIGS. 12B1-12B6 present the nucleotide sequence shown in FIGS. 12A1-12A3 (top line, SEQ ID NO:26) and the deduced amino acid sequences using the three possible open reading frames, second line (SEQ ID NOS:27-42), third line (SEQ ID NOS:43-47), fourth line (SEQ ID NOS:48-64). The amino acid sequence with the greatest homology to the mouse Delta-1 amino acid sequence is boxed. This boxed amino acid sequence is the predicted amino acid sequence of human Delta; where the reading frame shifts indicates where a sequencing error is present in the sequence. No single reading frame shown in FIGS. 12A1-12A3 gave an uninterrupted amino acid sequence due to errors in the DNA sequence that caused shifts in the reading frame. X indicates an undetermined amino acid; N indicates an undetermined nucleotide.

FIGS. 13A-13G. An alignment of mouse M-Delta-1 DNA sequence (top line, SEQ ID NO:4) and human H-Delta-1 DNA sequence (second line, SEQ ID NO:26) and their consensus sequence (third line, SEQ ID NO:24).

Figure 14A:
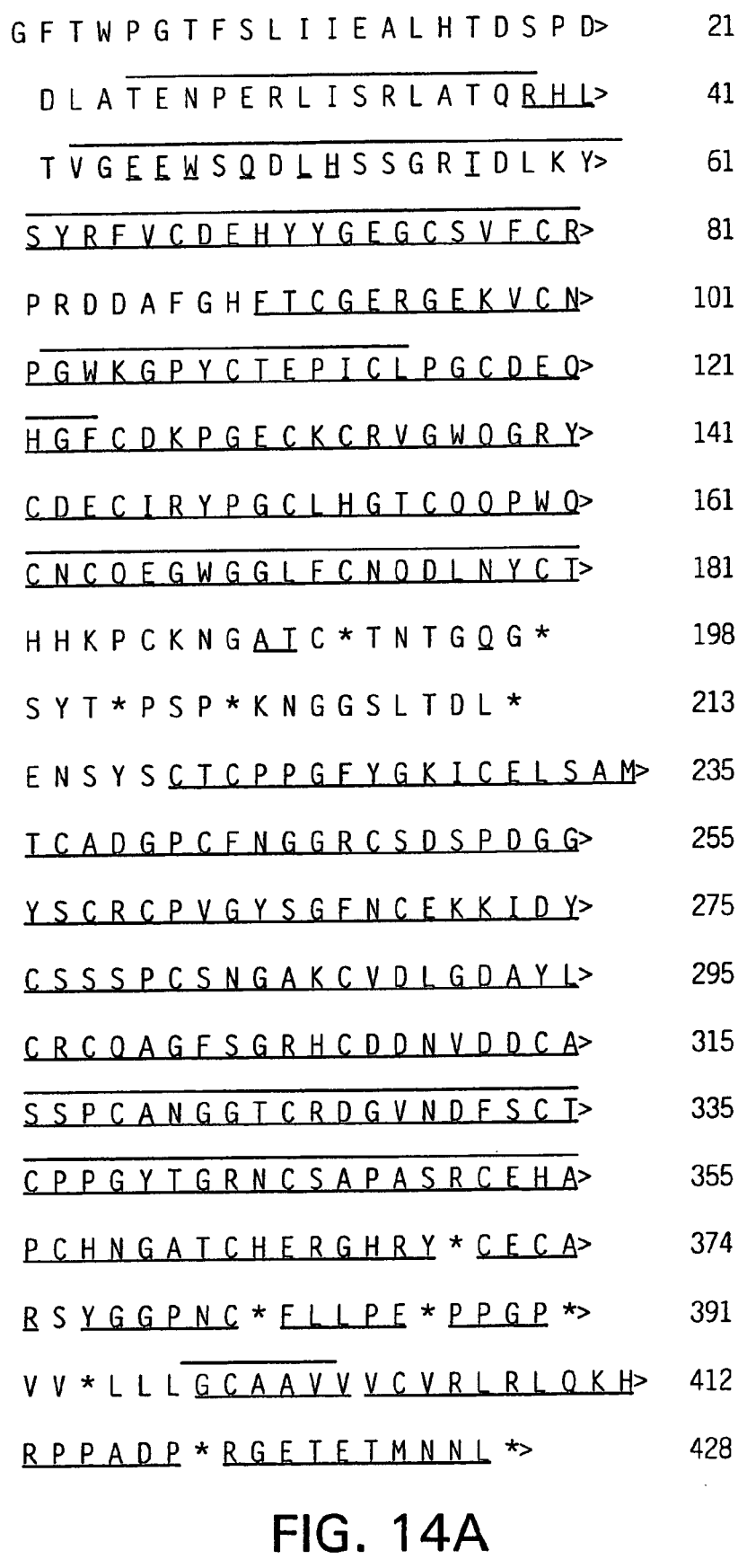
Figure 14B:
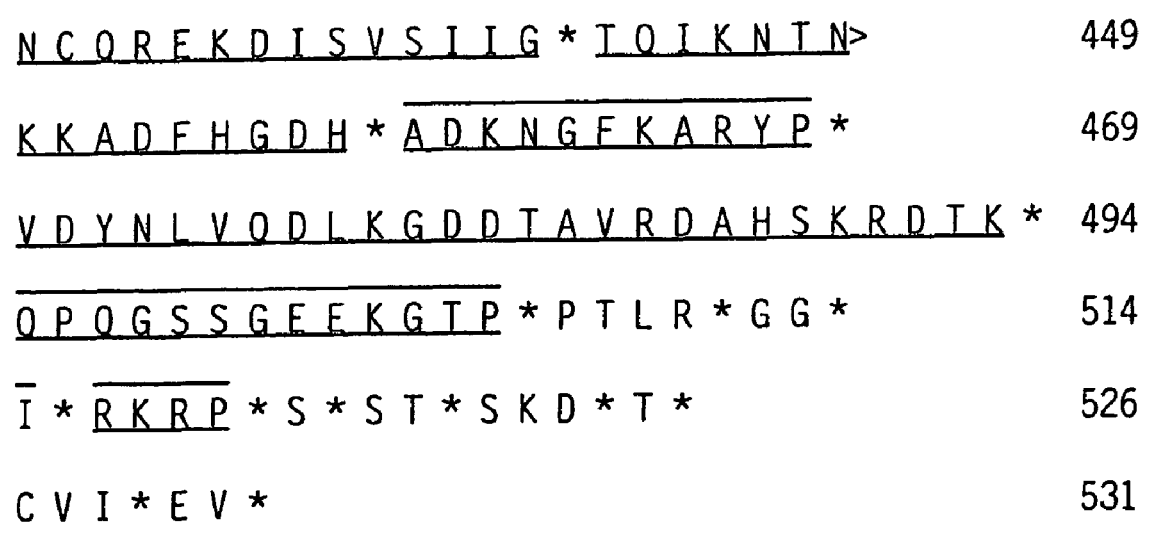

FIGS. 14A-14B. The composite human Delta (H-Delta-1) amino acid sequence (SEQ ID NOS:65-80, respectively) is presented, representing the boxed amino sequence from FIGS. 12B1-12B6. ">" indicates that the sequence continues on the line below. "*" indicates a break in the sequence.

5. DETAILED DESCRIPTION OF THE INVENTION

The present invention relates to nucleotide sequences of vertebrate Delta genes, and amino acid sequences of their encoded proteins. The invention further relates to fragments and other derivatives, and analogs, of vertebrate Delta proteins. Nucleic acids encoding such fragments or derivatives are also within the scope of the invention. The invention provides Delta genes and their encoded proteins of many different vertebrate species. The Delta genes of the invention include chick, mouse, and human Delta and related genes (homologs) in other vertebrate species. In specific embodiments, the Delta genes and proteins are from vertebrates, or more particularly, mammals. In a preferred embodiment of the invention, the Delta protein is a human protein. Production of the foregoing proteins and derivatives, e.g., by recombinant methods, is provided.

The invention relates to Delta derivatives and analogs of the invention which are functionally active, i.e., they are capable of displaying one or more known functional activities associated with a full-length (wild-type) Delta protein. Such functional activities include but are not limited to antigenicity [ability to bind (or compete with Delta for binding) to an anti-Delta antibody], immunogenicity (ability to generate antibody which binds to Delta), ability to bind (or compete with Delta for binding) to Notch or other toporythmic proteins or fragments thereof ("adhesiveness"), ability to bind (or compete with Delta for binding) to a receptor for Delta, ability to affect cell fate differentiation, and therapeutic activity. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Delta which comprise one or more domains of the Delta protein, including but not limited to the intracellular domain, extracellular domain, DSL domain, region amino-terminal to the DSL domain, transmembrane domain, membrane-associated region, or one or more EGF-like (homologous) repeats of a Delta protein, or any combination of the foregoing.

Antibodies to vertebrate Delta, its derivatives and analogs, are additionally provided.

As demonstrated infra, Delta plays a critical role in development and other physiological processes, in particular, as a ligand to Notch, which is involved in cell fate (differentiation) determination. In particular, Delta is believed to play a major role in determining cell fates in the central nervous system. The nucleic acid and amino acid sequences and antibodies thereto of the invention can be used for the detection and quantitation of Delta mRNA and protein of human and other species, to study expression thereof, to produce Delta and fragments and other derivatives and analogs thereof, in the study and manipulation of differentiation and other physiological processes. The present invention also relates to therapeutic and diagnostic methods and compositions based on Delta proteins and nucleic acids. The invention provides for treatment of disorders of cell fate or differentiation by administration of a therapeutic compound of the invention. Such therapeutic compounds (termed herein "Therapeutics") include: Delta proteins and analogs and derivatives (including fragments) thereof; antibodies thereto; nucleic acids encoding the Delta proteins, analogs, or derivatives; and Delta antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or Delta function (hereinafter "Antagonist Therapeutics") are administered for therapeutic effect. In another embodiment, Therapeutics which promote Notch and/or Delta function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Delta protein can be diagnosed by detecting such levels, as described more fully infra.

In a preferred aspect, a Therapeutic of the invention is a protein consisting of at least a fragment (termed herein "adhesive fragment") of Delta which mediates binding to a Notch protein or a fragment thereof.

The invention is illustrated by way of examples infra which disclose, inter alia, the cloning of a chick Delta homolog (Section 6), the cloning of a mouse Delta homolog (Section 7), and the cloning of a human Delta homolog (Section 8).

For clarity of disclosure, and not by way of limitation, the detailed description of the invention is divided into the subsections which follow.

5.1. Isolation of the Delta Genes

The invention relates to the nucleotide sequences of vertebrate Delta nucleic acids. In specific embodiments, human Delta nucleic acids comprise the cDNA sequences shown in FIGS. 10A-10B (SEQ ID NO:14) or in FIGS. 12A1-12A3 (SEQ ID NO:26), or the coding regions thereof, or nucleic acids encoding a vertebrate Delta protein (e.g., having the sequence of SEQ ID NO:1, 3, 11, 14 or 26). The invention provides nucleic acids consisting of at least 8 nucleotides (i.e., a hybridizable portion) of a vertebrate Delta sequence; in other embodiments, the nucleic acids consist of at least 25 (continuous) nucleotides, 50 nucleotides, 100 nucleotides, 150 nucleotides, or 200 nucleotides of a Delta sequence, or a full-length Delta coding sequence. The invention also relates to nucleic acids hybridizable to or complementary to the foregoing sequences or their complements. In specific aspects, nucleic acids are provided which comprise a sequence complementary to at least 10, 25, 50, 100, or 200 nucleotides or the entire coding region of a vertebrate Delta gene. In a specific embodiment, a nucleic acid which is hybridizable to a vertebrate (e.g., mammalian) Delta nucleic acid (e.g., having sequence SEQ ID NO:14 or SEQ ID NO:26, or an at least 10, 25, 50, 100, or 200 nucleotide portion thereof), or to a nucleic acid encoding a Delta derivative, under conditions of low stringency is provided. By way of example and not limitation, procedures using such conditions of low stringency are as follows (see also Shilo and Weinberg, 1981, Proc. Natl. Acad. Sci. USA 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20× $10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

In another specific embodiment, a nucleic acid which is hybridizable to a vertebrate (e.g., mammalian) Delta nucleic acid under conditions of high stringency is provided. By way of example and not limitation, procedures using such conditions of high stringency are as follows:

Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

Nucleic acids encoding fragments and derivatives of vertebrate Delta proteins (see Section 5.6), and Delta antisense nucleic acids (see Section 5.11) are additionally provided. As is readily apparent, as used herein, a "nucleic acid encoding a fragment or portion of a Delta protein" shall be construed as referring to a nucleic acid encoding only the recited fragment or portion of the Delta protein and not the other contiguous portions of the Delta protein as a continuous sequence.

Fragments of vertebrate Delta nucleic acids comprising regions of homology to other toporythmic proteins are also provided. The DSL regions (regions of homology with *Drosophila* Serrate and Delta) of Delta proteins of other species are also provided. Nucleic acids encoding conserved regions between Delta and Serrate, such as those shown in FIGS. 3A-3B and 8 are also provided.

Specific embodiments for the cloning of a vertebrate Delta gene, presented as a particular example but not by way of limitation, follows:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Delta product. In one embodiment, anti-Delta antibodies can be used for selection.

In another preferred aspect, PCR is used to amplify the desired sequence in a genomic or cDNA library, prior to selection. Oligonucleotide primers representing known Delta sequences (preferably vertebrate sequences) can be used as primers in PCR. In a preferred aspect, the oligonucleotide primers represent at least part of the Delta conserved segments of strong homology between Serrate and Delta. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Delta nucleotide sequence and the nucleic acid homolog being isolated. For cross species hybridization, low stringency conditions are preferred. For same species hybridization, moderately stringent conditions are preferred. After successful amplification of a segment of a Delta homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Delta proteins may be identified. Such a procedure is presented by way of example in various examples sections infra.

The above-methods are not meant to limit the following general description of methods by which clones of Delta may be obtained.

Any vertebrate cell potentially can serve as the nucleic acid source for the molecular cloning of the Delta gene. The nucleic acid sequences encoding Delta can be isolated from mammalian, human, porcine, bovine, feline, avian, equine, canine, as well as additional primate sources, etc. For example, we have amplified fragments of the Delta gene in mouse, chicken, and human, by PCR using cDNA libraries with Delta primers. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Delta (of any species) gene or its specific RNA, or a fragment thereof, e.g., an extracellular domain (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, binding activity, in vitro aggregation activity ("adhesiveness") or antigenic properties as known for Delta. If an antibody to Delta is available, the Delta protein may be identified by binding of labeled antibody to the putatively Delta synthesizing clones, in an ELISA (enzyme-linked immunosorbent assay)-type procedure.

The Delta gene can also be identified by mRNA selection by nucleic acid hybridization followed by in vitro translation. In this procedure, fragments are used to isolate complementary mRNAs by hybridization. Such DNA fragments may represent available, purified Delta DNA of another species (e.g., *Drosophila*). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Delta protein. A radiolabelled Delta cDNA can be synthesized using the selected mRNA (from the adsorbed polysomes) as a template. The radiolabelled mRNA or cDNA may then be used as a probe to identify the Delta DNA fragments from among other genomic DNA fragments.

Alternatives to isolating the Delta genomic DNA include, but are not limited to, chemically synthesizing the gene sequence itself from a known sequence or making cDNA to the mRNA which encodes the Delta protein. For example, RNA for cDNA cloning of the Delta gene can be isolated from cells which express Delta. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Delta gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated Delta gene, cDNA, or synthesized DNA sequence enables generation of multiple copies of the gene. Thus, the gene may be obtained in large quantities by growing transformants, isolating the recombinant DNA molecules from the transformants and; when necessary, retrieving the inserted gene from the isolated recombinant DNA.

The Delta sequences provided by the instant invention include those nucleotide sequences encoding substantially the same amino acid sequences as found in native vertebrate Delta proteins, and those encoded amino acid sequences with functionally equivalent amino acids, all as described in Section 5.6 infra for Delta derivatives.

5.2. Expression of the Delta Genes

The nucleotide sequence coding for a vertebrate Delta protein or a functionally active fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native Delta gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Delta gene is expressed. In other specific embodiments, the human Delta gene is expressed, or a sequence encoding a functionally active portion of human Delta. In yet another embodiment, a fragment of Delta comprising the extracellular domain, or other derivative, or analog of Delta is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Delta protein or peptide fragment may be regulated by a second nucleic acid sequence so that the Delta protein or peptide is expressed in a host transformed with the recombinant DNA molecule. For example, expression of a Delta protein may be controlled by any promoter/enhancer element known in the art. Promoters which may be used to control Delta gene expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Expression vectors containing Delta gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Delta gene is inserted within the marker gene sequence of the vector, recombinants containing the Delta insert can be identified by the absence of the marker gene function. In the third approach, recombinant expression vectors can be identified by assaying the foreign gene product expressed by the recombinant. Such assays can be based, for example, on the physical or functional properties of the Delta gene product in vitro assay systems, e.g., aggregation (binding) with Notch, binding to a receptor, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Delta protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian Delta protein. Furthermore, different vector/host expression systems may effect processing reactions such as proteolytic cleavages to different extents.

In other specific embodiments, the Delta protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. Identification and Purification of the Delta Gene Products

In particular aspects, the invention provides amino acid sequences of a vertebrate Delta, preferably a human Delta, and fragments and derivatives thereof which comprise an antigenic determinant (i.e., can be recognized by an antibody) or which are otherwise functionally active, as well as nucleic acid sequences encoding the foregoing. "Functionally active" material as used herein refers to that material displaying one or more known functional activities associated with a full-length (wild-type) Delta protein, e.g., binding to Notch or a portion thereof, binding to any other Delta ligand, antigenicity (binding to an anti-Delta antibody), etc.

In specific embodiments, the invention provides fragments of a Delta protein consisting of at least 6 amino acids, 10 amino acids, 25 amino acids, 50 amino acids, or of at least 75 amino acids. Molecules comprising such fragments are also provided. In other embodiments, the proteins comprise or consist essentially of an extracellular domain, DSL domain, epidermal growth factor-like repeat (ELR) domain, one or any combination of ELRs, transmembrane domain, or intracellular (cytoplasmic) domain, or a portion which binds to Notch, or any combination of the foregoing, of a vertebrate Delta protein. Fragments, or proteins comprising fragments, lacking some or all of the foregoing regions of a Delta protein are also provided. Nucleic acids encoding the foregoing are provided.

Once a recombinant which expresses the Delta gene sequence is identified, the gene product can be analyzed. This is achieved by assays based on the physical or functional properties of the product, including radioactive labelling of the product followed by analysis by gel electrophoresis, immunoassay, etc.

Once the Delta protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a Delta protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105-111).

In a specific embodiment of the present invention, such Delta proteins, whether produced by recombinant DNA techniques or by chemical synthetic methods, include but are not limited to those containing, as a primary amino acid sequence, all or part of the amino acid sequences substantially as depicted in FIGS. 2, 8, 11 or 14A-14B (SEQ ID NOS:2, 12, 23 and 65-80), as well as fragments and other derivatives, and analogs thereof.

5.4. Stricture of the Delta Genes and Proteins

The structure of the vertebrate Delta genes and proteins can be analyzed by various methods known in the art.

5.4.1. Genetic Analysis

The cloned DNA or cDNA corresponding to the Delta gene can be analyzed by methods including but not limited to Southern hybridization (Southern, E. M., 1975, J. Mol. Biol. 98:503-517), Northern hybridization (see e.g., Freeman et al., 1983, Proc. Natl. Acad. Sci. U.S.A. 80:4094-4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652-7656; Ochman et al., 1988, Genetics 120:621-623; Loh et al., 1989, Science 243:217-220) followed by Southern hybridization with a Delta-specific probe can allow the detection of the Delta gene in DNA from various cell types. Methods of amplification other than PCR are commonly known and can also be employed. In one embodiment, Southern hybridization can be used to determine the genetic linkage of Delta. Northern hybridization analysis can be used to determine the expression of the Delta gene. Various cell types, at various states of development or activity can be tested for Delta expression. Examples of such techniques and their results are described in Section 6, infra. The stringency of the hybridization conditions for both Southern and Northern hybridization can be manipulated to ensure detection of nucleic acids with the desired degree of relatedness to the specific Delta probe used.

Restriction endonuclease mapping can be used to roughly determine the genetic structure of the Delta gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499-560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. Protein Analysis

The amino acid sequence of the Delta protein can be derived by deduction from the DNA sequence, or alternatively, by direct sequencing of the protein, e.g., with an automated amino acid sequencer. The amino acid sequence of a representative Delta protein comprises the sequence substantially as depicted in FIG. 2, and detailed in Section 6, infra, with the representative mature protein that shown by amino acid numbers 1-728.

The Delta protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Delta protein and the corresponding regions of the gene sequence which encode such regions. Hydrophilic regions are more likely to be immunogenic.

Secondary, structural analysis (Chou, P. and Fasman, G., 1974, Biochemistry 13:222) can also be done, to identify regions of Delta that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. Generation of Antibodies to Delta Proteins and Derivatives Thereof

According to the invention, a vertebrate Delta protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to human Delta are produced. In another embodiment, antibodies to the extracellular domain of Delta are produced. In another embodiment, antibodies to the intracellular domain of Delta are produced.

Various procedures known in the art may be used for the production of polyclonal antibodies to a Delta protein or derivative or analog. In a particular embodiment, rabbit polyclonal antibodies to an epitope of the Delta protein encoded by a sequence depicted in FIGS. 1A1-1A3, 1B1-1B2, 7A-7B or 11, or a subsequence thereof, can be obtained. For the production of antibody, various host animals can be immunized by injection with the native Delta protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Delta protein sequence or analog thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for Delta together with genes from a human antibody molecule of appropriate biological activity can be used; such antibodies are within the scope of this invention.

According to the invention, techniques described for the production of single chain antibodies (U.S. Pat. No. 4,946,778) can be adapted to produce Delta-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for Delta proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a vertebrate Delta protein, one may assay generated hybridomas for a product which binds to a Delta fragment containing such domain. For selection of an antibody immunospecific to human Delta, one can select on the basis of positive binding to human Delta and a lack of binding to *Drosophila* Delta.

The foregoing antibodies can be used in methods known in the art relating to the localization and activity of the protein sequences of the invention (e.g., see Section 5.7, infra), e.g., for imaging these proteins, measuring levels thereof in appropriate physiological samples, in diagnostic methods, etc.

Antibodies specific to a domain of a Delta protein are also provided. In a specific embodiment, antibodies which bind to a Notch-binding fragment of Delta are provided.

In another embodiment of the invention (see infra), anti-Delta antibodies and fragments thereof containing the binding domain are Therapeutics.

5.6. Delta Proteins, Derivatives and Analogs

The invention further relates to vertebrate (e.g., mammalian) Delta proteins, and derivatives (including but not limited to fragments) and analogs of vertebrate Delta proteins. Nucleic acids encoding Delta protein derivatives and protein analogs are also provided. In one embodiment, the Delta proteins are encoded by the Delta nucleic acids described in Section 5.1 supra. In particular aspects, the proteins, derivatives, or analogs are of mouse, chicken, rat, pig, cow, dog, monkey, or human Delta proteins. In a specific embodiment, a mature, full-length vertebrate Delta protein is provided. In one embodiment, a vertebrate Delta protein lacking only the signal sequence (approximately the first 17 amino-terminal amino acids) is provided.

The production and use of derivatives and analogs related to Delta are within the scope of the present invention. In a specific embodiment, the derivative or analog is functionally active, i.e., capable of exhibiting one or more functional activities associated with a full-length, wild-type Delta protein. As one example, such derivatives or analogs which have the desired immunogenicity or antigenicity can be used, for example, in immunoassays, for immunization, for inhibition of Delta activity, etc. Such molecules which retain, or alternatively inhibit, a desired Delta property, e.g., binding to Notch or other toporythmic proteins, binding to a cell-surface receptor, can be used as inducers, or inhibitors, respectively, of such property and its physiological correlates. A specific embodiment relates to a Delta fragment that can be bound by an anti-Delta antibody but cannot bind to a Notch protein or other toporythmic protein. Derivatives or analogs of Delta can be tested for the desired activity by procedures known in the art, including but not limited to the assays described in Section 5.7.

In particular, Delta derivatives can be made by altering Delta sequences by substitutions, additions or deletions that provide for functionally equivalent molecules. Due to the degeneracy of nucleotide coding sequences, other DNA sequences which encode substantially the same amino acid sequence as a Delta gene may be used in the practice of the present invention. These include but are not limited to nucleotide sequences comprising all or portions of Delta genes which are altered by the substitution of different codons that encode a functionally equivalent amino acid residue within the sequence, thus producing a silent change. Likewise, the Delta derivatives of the invention include, but are not limited to, those containing, as a primary amino acid sequence, all or part of the amino acid sequence of a Delta protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a vertebrate Delta protein consisting of at least 10 (continuous) amino acids of the Delta protein is provided. In other embodiments, the fragment consists of at least 20 or 50 amino acids of the Delta protein. In specific embodiments, such fragments are not larger than 35, 100 or 200 amino acids. Derivatives or analogs of Delta include but are not limited to those peptides which are substantially homologous to a vertebrate Delta protein or fragments thereof (e.g., at least 30%, 50%, 70%, or 90% identity over an amino acid sequence of identical size—e.g., comprising a domain) or whose encoding nucleic acid is capable of hybridizing to a coding Delta sequence.

The Delta derivatives and analogs of the invention can be produced by various methods known in the art. The manipulations which result in their production can occur at the gene or protein level. For example, the cloned Delta gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Delta, care should be taken to ensure that the modified gene remains within the same translational reading frame as Delta, uninterrupted by translational stop signals, in the gene region where the desired Delta activity is encoded.

Additionally, the Delta-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc. PCR primers containing sequence changes can be used in PCR to introduce such changes into the amplified fragments.

Manipulations of the Delta sequence may also be made at the protein level. Included within the scope of the invention are Delta protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Delta can be chemically synthesized. For example, a peptide corresponding to a portion of a Delta protein which comprises the desired domain (see Section 5.6.1), or which mediates the desired aggregation activity in vitro, or binding to a receptor, can be synthesized by use of a peptide synthesizer.

Furthermore, if desired, nonclassical amino acids or chemical amino acid analogs can be introduced as a substitution or addition into the Delta sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the Delta derivative is a chimeric, or fusion, protein comprising a vertebrate Delta protein or fragment thereof (preferably consisting of at least a domain or motif of the Delta protein, or at least 10 amino acids of the Delta protein) joined at its amino- or carboxy-terminus via a peptide bond to an amino acid sequence of a different protein. In one embodiment, such a chimeric protein is produced by recombinant expression of a nucleic acid encoding the protein (comprising a Delta-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by peptide synthetic techniques, e.g., by use of a peptide synthesizer. In a specific embodiment, a chimeric nucleic acid encoding a mature Delta protein with a heterologous signal sequence is expressed such that the chimeric protein is expressed and processed by the cell to the mature Delta protein. As another example, and not by way of limitation, a recombinant molecule can be constructed according to the invention, comprising coding portions of both Delta and another toporythmic gene, e.g., Serrate. The encoded protein of such a recombinant molecule could exhibit properties associated with both Serrate and Delta and portray a novel profile of biological activities, including agonists as well as antagonists. The primary sequence of Delta and Serrate may also be used to predict tertiary structure of the molecules using computer simulation (Hopp and Woods, 1981, Proc. Natl. Acad. Sci. U.S.A. 78:3824-3828); Delta/Serrate chimeric recombinant genes could be designed in light of correlations between tertiary structure and biological function. Likewise, chimeric genes comprising portions of Delta fused to any heterologous protein-encoding sequences may be constructed. A specific embodiment relates to a chimeric protein comprising a fragment of Delta of at least six amino acids.

In another specific embodiment, the Delta derivative is a fragment of vertebrate Delta comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region. For example, such a Delta fragment can comprise one or more regions homologous to Serrate, including but not limited to the DSL domain or a portion thereof.

Other specific embodiments of derivatives and analogs are described in the subsections below and examples sections infra.

5.6.1. Derivatives of Delta Containing One or More Domains of the Protein

In a specific embodiment, the invention relates to vertebrate Delta derivatives and analogs, in particular Delta fragments and derivatives of such fragments, that comprise, or alternatively consist of, one or more domains of the Delta protein, including but not limited to the extracellular domain, signal sequence, region amino-terminal to the DSL domain, DSL domain, ELR domain, transmembrane domain, intracellular domain, and one or more of the EGF-like repeats (ELR) of the Delta protein (e.g., ELRs 1-9), or any combination of the foregoing. In particular examples relating to the chick and mouse Delta proteins, such domains are identified in Examples Section 6 and 7, respectively, and in FIGS. 3A-3B and 9A-9B. Thus, by way of example is provided, a molecule comprising an extracellular domain (approximately amino acids 1-545), signal sequence (approximately amino acids 1-17), region amino-terminal to the DSL domain (approximately amino acids 1-178), the DSL domain (approximately amino acids 179-223), EGF1 (approximately amino acids 229-260), EGF2 (approximately amino acids 261-292), EGF3 (approximately amino acids 293-332), EGF4 (approximately amino acids 333-370), EGF5 (approximately amino acids 371-409), EGF6 (approximately amino acids 410-447), EGF7 (approximately amino acids 448-485), EGF8 (approximately amino acids 486-523), transmembrane domain, and intracellular (cytoplasmic) domain (approximately amino acids 555-728) of a vertebrate Delta.

In another embodiment, the molecules comprising specific fragments of vertebrate Delta are those comprising fragments in the respective Delta protein most homologous to specific fragments of the *Drosophila* or chick Delta protein. In particular embodiments, such a molecule comprises or consists of the amino acid sequences of SEQ ID NO:2 or 23. Alternatively, a fragment comprising a domain of a Delta homolog can be identified by protein analysis methods as described in Section 5.3.2.

5.6.2. Derivatives of Delta that Mediate Binding to Toporythmic Protein Domains The invention also provides for vertebrate Delta fragments, and analogs or derivatives of such fragments, which mediate binding to toporythmic proteins (and thus are termed herein "adhesive"), and nucleic acid sequences encoding the foregoing.

In a particular embodiment, the adhesive fragment of a Delta protein comprises the DSL domain, or a portion thereof. Subfragments within the DSL domain that mediate binding to Notch can be identified by analysis of constructs expressing deletion mutants.

The ability to bind to a toporythmic protein (preferably Notch) can be demonstrated by in vitro aggregation assays with cells expressing such a toporythmic protein as well as cells expressing Delta or a Delta derivative (See Section 5.7). That is, the ability of a Delta fragment to bind to a Notch protein can be demonstrated by detecting the ability of the Delta fragment, when expressed on the surface of a first cell, to bind to a Notch protein expressed on the surface of a second cell.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

5.7. Assays of Delta Proteins, Derivatives and Analogs

The functional activity of vertebrate Delta proteins, derivatives and analogs can be assayed by various methods.

For example, in one embodiment, where one is assaying for the ability to bind or compete with wild-type Delta for binding to anti-Delta antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to a toporythmic protein, e.g., Notch, one can carry out an in vitro aggregation assay (see Fehon et al., 1990, Cell 61:523-534; Rebay et al., 1991, Cell 67:687-699).

In another embodiment, where a receptor for Delta is identified, receptor binding can be assayed, e.g., by means well-known in the art. In another embodiment, physiological correlates of Delta binding to cells expressing a Delta receptor (signal transduction) can be assayed.

In another embodiment, in insect or other model systems, genetic studies can be done to study the phenotypic effect of a Delta mutant that is a derivative or analog of wild-type Delta.

Other methods will be known to the skilled artisan and are within the scope of the invention.

5.8. Therapeutic Uses

The invention provides for treatment of disorders of cell fate or differentiation by administration of a therapeutic compound of the invention. Such therapeutic compounds (termed herein "Therapeutics") include: Delta proteins and analogs and derivatives (including fragments) thereof (e.g., as described hereinabove); antibodies thereto (as described hereinabove); nucleic acids encoding the Delta proteins, analogs, or derivatives (e.g., as described hereinabove); and Delta antisense nucleic acids. As stated supra, the Antagonist Therapeutics of the invention are those Therapeutics which antagonize, or inhibit, a Delta function and/or Notch function (since Delta is a Notch ligand). Such Antagonist Therapeutics are most preferably identified by use of known convenient in vitro assays, e.g., based on their ability to inhibit binding of Delta to another protein (e.g., a Notch protein), or inhibit any known Notch or Delta function as preferably assayed in vitro or in cell culture, although genetic assays (e.g., in *Drosophila*) may also be employed. In a preferred embodiment, the Antagonist Therapeutic is a protein or derivative thereof comprising a functionally active fragment such as a fragment of Delta which mediates binding to Notch, or an antibody thereto. In other specific embodiments, such an Antagonist Therapeutic is a nucleic acid capable of expressing a molecule comprising a fragment of Delta which binds to Notch, or a Delta antisense nucleic acid (see Section 5.11 herein). It should be noted that preferably, suitable in vitro or in vivo assays, as described infra, should be utilized to determine the effect of a specific Therapeutic and whether its administration is indicated for treatment of the affected tissue, since the developmental history of the tissue may determine whether an Antagonist or Agonist Therapeutic is desired.

In addition, the mode of administration, e.g., whether administered in soluble form or administered via its encoding nucleic acid for intracellular recombinant expression, of the Delta protein or derivative can affect whether it acts as an agonist or antagonist.

In another embodiment of the invention, a nucleic acid containing a portion of a Delta gene is used, as an Antagonist Therapeutic, to promote Delta inactivation by homologous recombination (Koller and Smithies, 1989, Proc. Natl. Acad. Sci. USA 86:8932-8935; Zijlstra et al., 1989, Nature 342: 435-438).

The Agonist Therapeutics of the invention, as described supra, promote Delta function. Such Agonist Therapeutics include but are not limited to proteins and derivatives comprising the portions of Notch that mediate binding to Delta, and nucleic acids encoding the foregoing (which can be administered to express their encoded products in vivo).

Further descriptions and sources of Therapeutics of the inventions are found in Sections 5.1 through 5.7 herein.

Molecules which retain, or alternatively inhibit, a desired Delta property, e.g., binding to Notch, binding to an intracellular ligand, can be used therapeutically as inducers, or inhibitors, respectively, of such property and its physiological correlates. In a specific embodiment, a peptide (e.g., in the range of 6-50 or 15-25 amino acids; and particularly of about 10, 15, 20 or 25 amino acids) containing the sequence of a portion of Delta which binds to Notch is used to antagonize Notch function. In a specific embodiment, such an Antagonist Therapeutic is used to treat or prevent human or other malignancies associated with increased Notch expression (e.g., cervical cancer, colon cancer, breast cancer, squamous adenocarcimas (see infra)). Derivatives or analogs of Delta can be tested for the desired activity by procedures known in the art, including but not limited to the assays described in the examples infra. For example, molecules comprising Delta fragments which bind to Notch EGF-repeats (ELR) 11 and 12 and which are smaller than a DSL domain, can be obtained and selected by expressing deletion mutants and assaying for binding of the expressed product to Notch by any of the several methods (e.g., in vitro cell aggregation assays, interaction trap system), some of which are described in the Examples Sections infra. In one specific embodiment, peptide libraries can be screened to select a peptide with the desired activity; such screening can be carried out by assaying, e.g., for binding to Notch or a molecule containing the Notch ELR 11 and 12 repeats.

Other Therapeutics include molecules that bind to a vertebrate Delta protein. Thus, the invention also provides a method for identifying such molecules. Such molecules can be identified by a method comprising contacting a plurality of molecules (e.g., in a peptide library, or combinatorial chemical library) with the Delta protein under conditions conducive to binding, and recovering any molecules that bind to the Delta protein.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch or Delta function, for example, in patients where Notch or Delta protein is lacking, genetically defective, biologically inactive or underactive, or underexpressed; and (2) in diseases or disorders wherein in vitro (or in vivo) assays (see infra) indicate the utility of Delta agonist administration. The absence or decreased levels in Notch or Delta function can be readily detected, e.g., by obtaining a patient tissue sample (e.g., from biopsy tissue) and assaying it in vitro for protein levels, structure and/or activity of the expressed Notch or Delta protein. Many methods standard in the art can be thus employed, including but not limited to immunoassays to detect and/or visualize Notch or Delta protein (e.g., Western blot, immunoprecipitation followed by sodium dodecyl sulfate polyacrylamide gel electrophoresis, immunocytochemistry, etc.) and/or hybridization assays to detect Notch or Delta expression by detecting and/or visualizing respectively Notch or Delta mRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating nerve injury or a nervous system degenerative disorder (see Section 5.8.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch or Delta dominant activated phenotype ("gain of function" mutations.) Administration of an Agonist Therapeutic is indicated in diseases or disorders determined or known to involve a Notch or Delta dominant negative phenotype ("loss of function" mutations). The functions of various structural domains of the Notch protein have been investigated in vivo, by ectopically expressing a series of Drosophila Notch deletion mutants under the hsp70 heat-shock promoter, as well as eye-specific promoters (see Rebay et al., 1993, Cell 74:319-329). Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. The results indicated that Notch functions as a receptor whose extracellular domain mediates ligand-binding, resulting in the transmission of developmental signals by the cytoplasmic domain.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436-446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch or Delta function, for example, where the Notch or Delta protein is overexpressed or overactive; and (2) in diseases or disorders wherein in vitro (or in vivo) assays indicate the utility of Delta antagonist administration. The increased levels of Notch or Delta function can be readily detected by methods such as those described above, by quantifying protein and/or RNA. In vitro assays with cells of patient tissue sample or the appropriate cell line or cell type, to determine therapeutic utility, can be carried out as described above.

5.8.1. Malignancies

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.8.1 and 5.9.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, *Medicine*, 2d Ed., J. B. Lippincott Co., Philadelphia):

TABLE 1

| MALIGNANCIES AND RELATED DISORDERS |
|---|
| Leukemia |
|   acute leukemia |
|     acute lymphocytic leukemia |
|     acute myelocytic leukemia |
|       myeloblastic |
|       promyelocytic |
|       myelomonocytic |
|       monocytic |
|       erythroleukemia |
|   chronic leukemia |
|     chronic myelocytic (granulocytic) leukemia |
|     chronic lymphocytic leukemia |
| Polycythemia vera |
| Lymphoma |
|   Hodgkin's disease |
|   non-Hodgkin's disease |
| Multiple myeloma |
| Waldenstrom's macroglobulinemia |
| Heavy chain disease |
| Solid tumors |
|   sarcomas and carcinomas |
|     fibrosarcoma |
|     myxosarcoma |
|     liposarcoma |
|     chondrosarcoma |
|     osteogenic sarcoma |
|     chordoma |
|     angiosarcoma |
|     endotheliosarcoma |

TABLE 1-continued

| MALIGNANCIES AND RELATED DISORDERS |
|---|
|     lymphangiosarcoma |
|     lymphangioendotheliosarcoma |
|     synovioma |
|     mesothelioma |
|     Ewing's tumor |
|     leiomyosarcoma |
|     rhabdomyosarcoma |
|     colon carcinoma |
|     pancreatic cancer |
|     breast cancer |
|     ovarian cancer |
|     prostate cancer |
|     squamous cell carcinoma |
|     basal cell carcinoma |
|     adenocarcinoma |
|     sweat gland carcinoma |
|     sebaceous gland carcinoma |
|     papillary carcinoma |
|     papillary adenocarcinomas |
|     cystadenocarcinoma |
|     medullary carcinoma |
|     bronchogenic carcinoma |
|     renal cell carcinoma |
|     hepatoma |
|     bile duct carcinoma |
|     choriocarcinoma |
|     seminoma |
|     embryonal carcinoma |
|     Wilms' tumor |
|     cervical cancer |
|     testicular tumor |
|     lung carcinoma |
|     small cell lung carcinoma |
|     bladder carcinoma |
|     epithelial carcinoma |
|     glioma |
|     astrocytoma |
|     medulloblastoma |
|     craniopharyngioma |
|     ependymoma |
|     pinealoma |
|     hemangioblastoma |
|     acoustic neuroma |
|     oligodendroglioma |
|     menangioma |
|     melanoma |
|     neuroblastoma |
|     retinoblastoma |

In specific embodiments, malignancy or dysproliferative changes (such as metaplasias and dysplasias) are treated or prevented in epithelial tissues such as those in the cervix, esophagus, and lung.

Malignancies of the colon and cervix exhibit increased expression of human Notch relative to such non-malignant tissue (see PCT Publication no. WO 94/07474 published Apr. 14, 1994, incorporated by reference herein in its entirety). Thus, in specific embodiments, malignancies or premalignant changes of the colon or cervix are treated or prevented by administering an effective amount of an Antagonist Therapeutic, e.g., a Delta derivative, that antagonizes Notch function. The presence of increased Notch expression in colon, and cervical cancer suggests that many more cancerous and hyperproliferative conditions exhibit upregulated Notch. Thus, in specific embodiments, various cancers, e.g., breast cancer, squamous adenocarcinoma, seminoma, melanoma, and lung cancer, and premalignant changes therein, as well as other hyperproliferative disorders, can be treated or prevented by administration of an Antagonist Therapeutic that antagonizes Notch function.

5.8.2. Nervous System Disorders

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;
(ii) ischemic lesions, in which a lack of oxygen in a portion of the nervous system results in neuronal injury or death, including cerebral infarction or ischemia, or spinal cord infarction or ischemia;
(iii) malignant lesions, in which a portion of the nervous system is destroyed or injured by malignant tissue which is either a nervous system associated malignancy or a malignancy derived from non-nervous system tissue;
(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;
(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;
(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;
(vii) neurological lesions associated with systemic diseases including but not limited to diabetes (diabetic neuropathy, Bell's palsy), systemic lupus erythematosus, carcinoma, or sarcoidosis;
(viii) lesions caused by toxic substances including alcohol, lead, or particular neurotoxins; and
(ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.8). For example, and not by way of limitation, Therapeutics which elicit any of the following effects may be useful according to the invention:

(i) increased survival time of neurons in culture;
(ii) increased sprouting of neurons in culture or in vivo;
(iii) increased production of a neuron-associated molecule in culture or in vivo, e.g., choline acetyltransferase or acetylcholinesterase with respect to motor neurons; or
(iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507-3515); increased sprouting of neurons may be detected by methods set forth in Pestronk et al. (1980, Exp. Neurol. 70:65-82) or Brown et al. (1981, Ann. Rev. Neurosci. 4:17-42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.8.3. Tissue Repair and Regeneration

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly). In another embodiment, a Therapeutic of the invention is used to treat degenerative or traumatic disorders of the sensory epithelium of the inner ear.

5.9. Prophylactic Uses

5.9.1. Malignancies

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W. B. Saunders Co., Philadelphia, pp. 112-113) etc.)

In another specific embodiment, an Antagonist Therapeutic of the invention is administered to a human patient to prevent progression to breast, colon, or cervical cancer.

5.9.2. Other Disorders

In other embodiments, a Therapeutic of the invention can be administered to prevent a nervous system disorder described in Section 5.8.2, or other disorder (e.g., liver cirrhosis, psoriasis, keloids, baldness) described in Section 5.8.3.

5.10. Demonstration of Therapeutic or Prophylactic Utility

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.11. Antisense Regulation of Delta Expression

The present invention provides the therapeutic or prophylactic use of nucleic acids of at least six nucleotides that are antisense to a gene or cDNA encoding Delta or a portion thereof. "Antisense" as used herein refers to a nucleic acid capable of hybridizing to a portion of a Delta RNA (preferably mRNA) by virtue of some sequence complementarity. Such antisense nucleic acids have utility as Antagonist Therapeutics of the invention, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Delta antisense nucleic acids provided by the instant invention can be used for the treatment of tumors or other disorders, the cells of which tumor type or disorder can be demonstrated (in vitro or in vivo) to express a Delta gene or a Notch gene. Such demonstration can be by detection of RNA or of protein.

The invention further provides pharmaceutical compositions comprising an effective amount of the Delta antisense nucleic acids of the invention in a pharmaceutically acceptable carrier, as described infra in Section 5.12. Methods for treatment and prevention of disorders (such as those described in Sections 5.8 and 5.9) comprising administering the pharmaceutical compositions of the invention are also provided.

In another embodiment, the invention is directed to methods for inhibiting the expression of a Delta nucleic acid sequence in a prokaryotic or eukaryotic cell comprising providing the cell with an effective amount of a composition comprising an antisense Delta nucleic acid of the invention.

Delta antisense nucleic acids and their uses are described in detail below.

5.11.1. Delta Antisense Nucleic Acids

The Delta antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549).

In a preferred aspect of the invention, a Delta antisense oligonucleotide is provided, preferably of single-stranded DNA. In a most preferred aspect, such an oligonucleotide comprises a sequence antisense to the sequence encoding an SH3 binding domain or a Notch-binding domain of Delta, most preferably, of human Delta. The oligonucleotide may be modified at any position on its structure with substituents generally known in the art.

The Delta antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

In a specific embodiment, the Delta antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

In an alternative embodiment, the Delta antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Delta antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Delta antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc.

The antisense nucleic acids of the invention comprise a sequence complementary to at least a portion of an RNA transcript of a Delta gene, preferably a human Delta gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Delta antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Delta RNA it may contain and still form a stable duplex (or triplex, as the case may be). One skilled in the art can ascertain a tolerable degree of mismatch by use of standard procedures to determine the melting point of the hybridized complex.

5.11.2. Therapeutic Utility of Delta Antisense Nucleic Acids

The Delta antisense nucleic acids can be used to treat (or prevent) malignancies or other disorders, of a cell type which has been shown to express Delta or Notch. In specific embodiments, the malignancy is cervical, breast, or colon cancer, or squamous adenocarcinoma. Malignant, neoplastic, and pre-neoplastic cells which can be tested for such expression include but are not limited to those described supra in Sections 5.8.1 and 5.9.1. In a preferred embodiment, a single-stranded DNA antisense Delta oligonucleotide is used.

Malignant (particularly, tumor) cell types which express Delta or Notch RNA can be identified by various methods known in the art. Such methods include but are not limited to hybridization with a Delta or Notch-specific nucleic acid (e.g. by Northern hybridization, dot blot hybridization, in situ hybridization), observing the ability of RNA from the cell type to be translated in vitro into Notch or Delta, immunoassay, etc. In a preferred aspect, primary tumor tissue from a patient can be assayed for Notch or Delta expression prior to treatment, e.g., by immunocytochemistry or in situ hybridization.

Pharmaceutical compositions of the invention (see Section 5.12), comprising an effective amount of a Delta antisense nucleic acid in a pharmaceutically acceptable carrier, can be administered to a patient having a malignancy which is of a type that expresses Notch or Delta RNA or protein.

The amount of Delta antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Delta antisense nucleic acids are administered via liposomes, microparticles, or microcapsules. In various embodiments of the invention, it may be useful to use such compositions to achieve sustained release of the Delta antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448-2451; Renneisen et al., 1990, J. Biol. Chem. 265:16337-16342).

5.12. Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429-4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by infection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |

| Disorder | Preferred Forms of Administration |
| --- | --- |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.13. Diagnostic Utility

Delta proteins, analogues, derivatives, and subsequences thereof, Delta nucleic acids (and sequences complementary thereto), anti-Delta antibodies, have uses in diagnostics. Such molecules can be used in assays, such as immunoassays, to detect, prognose, diagnose, or monitor various conditions, diseases, and disorders affecting Delta expression, or monitor the treatment thereof. In particular, such an immunoassay is carried out by a method comprising contacting a sample derived from a patient with an anti-Delta antibody under conditions such that immunospecific binding can occur, and detecting or measuring the amount of any immunospecific binding by the antibody. In a specific aspect, such binding of antibody, in tissue sections, preferably in conjunction with binding of anti-Notch antibody can be used to detect aberrant Notch and/or Delta localization or aberrant levels of Notch-Delta colocalization in a disease state. In a specific embodiment, antibody to Delta can be used to assay in a patient tissue or serum sample for the presence of Delta where an aberrant level of Delta is an indication of a diseased condition. Aberrant levels of Delta binding ability in an endogenous Notch protein, or aberrant levels of binding ability to Notch (or other Delta ligand) in an endogenous Delta protein may be indicative of a disorder of cell fate (e.g., cancer, etc.) By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Delta genes and related nucleic acid sequences and subsequences, including complementary sequences, and other toporythmic gene sequences, can also be used in hybridization assays. Delta nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Delta expression and/or activity as described supra. In particular, such a hybridization assay is carried out by a method comprising contacting a sample containing nucleic acid with a nucleic acid probe capable of hybridizing to Delta DNA or RNA, under conditions such that hybridization can occur, and detecting or measuring any resulting hybridization.

Additionally, since Delta binds to Notch, Delta or a binding portion thereof can be used to assay for the presence and/or amounts of Notch in a sample, e.g., in screening for malignancies which exhibit increased Notch expression such as colon and cervical cancers.

6. A Delta Homolog in the Chick is Expressed in Prospective Neurons

As described herein, we have isolated and characterized a chick Delta homologue, C-Delta-1. We show that C-Delta-1 is expressed in prospective neurons during neurogenesis, as new cells are being born and their fates decided. Our data in the chick, suggest that both the Delta/Notch signalling mechanism and its role in neurogenesis have been conserved in vertebrates.

6.1. Cloning of C-Delta-1

We identified a chick Delta homologue, C-Delta-1, using the polymerase chain reaction (PCR) and degenerate oligonucleotide primers (FIGS. 1A1-1A3, 1B1-1B2 and 2, SEQ ID NOS:1, 2, 3 and 4). C-Delta-1 was cloned by PCR using the degenerate oligonucleotide primers TTCGGITT(C/T)AC-ITGGCCIGGIAC (SEQ ID NO:81) and TCIATGCAIGTIC-CICC(A/G)TT (SEQ ID NO:82) which correspond to the fly Delta protein sequences FGFTWPGT (SEQ ID NO:83) and NGGTCID (SEQ ID NO:84), respectively (Vässin et al., 1987, EMBO J. 6:3431-3440; Kopczynski et al., 1988, Genes Dev. 2:1723-1735). The initial reaction used 50 ng of first-strand oligo-d(T)-primed cDNA from stage 4-6 embryos, 1 g of each primer, 0.2 mM dNTPs, 2 U. of Taq polymerase, in 50 l of the supplied buffer (Perkin-Elmer). 40 cycles of amplification were performed at 94° C./30 sec; 50° C./2 min; 72° C./2 min. Amplified DNA fragments were separated on an agarose gel, cloned in Bluescript pKS-(Stratagene) and sequenced. Two Delta homologs were identified, one of which (C-Delta-1) is expressed in the nervous system. Of the homolog that is expressed in the nervous system, two variants were identified that differ at the carboxy-terminal end of the encoded protein due to an alternative splicing event at the 3' end of the C-Delta-1 gene. One encoded protein has 12 extra amino acids at the carboxy-terminal end, relative to the other encoded protein. The sequence of the shorter encoded variant is set forth in SEQ ID NO:2. The longer variant encoded by SEQ ID NO:3 and identified by the amino acid sequence of SEQ ID NO:4, consists of the amino acid sequence of SEQ ID NO:2 plus twelve additional amino acids at the 3' end (SIP-PGSRTSLGV) (SEQ ID NO:85). The longer variant was used in the experiments described below. When tested for biological activity by injection of RNA into Xenopus oocytes, each of the variants had the same biological activity.

DNA fragments corresponding to C-Delta-1 were used to screen a stage 17 spinal cord cDNA library and several full-length clones were obtained and sequenced. We amplified DNA fragments from chick C-Notch-1 gene by similar methods (data not shown); partial sequence data and pattern of expression indicate close similarity to the rodent Notch-1 gene (Weinmaster et al., 1991, Development 113:199-205; Weinmaster et al., 1992, Development 116:931-941; Lardelli & Lendahl, 1993, Exp. Cell Res. 204:364-372). Sequences were analyzed using the Wisconsin GCG set of programs. The GenBank Accession number for the Chick Delta-1 mRNA is U26590. The DNA sequence of C-Delta-1 corresponds to a protein of 722 amino acids, structurally homologous to Drosophila Delta (FIGS. 3A-3B, 4) and clearly distinct from vertebrate homologs of the Delta-related Serrate protein, which we have also cloned (data not shown). C-Delta-1 contains a putative transmembrane domain, a signal sequence and 8 EGF-like repeats in its extracellular region (one repeat less than Drosophila Delta). The amino-terminal domain of C-Delta-1 is closely related to a similar domain in the fly Delta protein, described as necessary and sufficient for in vitro binding to Notch (Muskavitch, 1994, Dev. Biol. 166: 415-430). This conserved region includes the so-called DSL motif (FIG. 4) (Henderson et al., 1994, Development 120: 2913-2924; Tax et al., 1994, Nature 368:150-154), shared by all known members of the family of presumed ligands of Notch-like proteins (Delta and Serrate in Drosophila; Lag-2 and Apx-1 in Caenorhabditis elegans) (Henderson et al., 1994, Development 120:2913-2924; Tax et al., 1994, Nature 368:150-154; Fleming et al., 1990, Genes Dev. 4:2188-2201; Thomas et al., 1991, Development 111:749-761; Mello et al., 1994, Cell 77:95-106). A second cysteine-rich N-terminal region is conserved between the fly and chick proteins, but absent from the related C. elegans proteins (FIG. 4). The Xenopus Delta-1 homologue, X-Delta-1 which encodes a protein that is 81% identical to C-Delta-1 and shows all the above structural motifs (FIGS. 3A-3B), has also been cloned. The structural conservation between the chick and fly Delta proteins, including domains identified as critical for Notch binding (Muskavitch, 1994, Dev. Biol. 166:415-430), suggests that C-Delta-1 functions as a ligand for a chick Notch protein, and that a Delta/Notch-mediated mechanism of lateral inhibition might operate in the chick.

6.2. C-Delta-1 and C-Notch-1 Expression Correlates with Onset of Neurogenesis During Drosophila neurogenesis, Delta is transiently expressed in neural precursors, inhibiting neighboring Notch-expressing cells from also becoming neural (Haenlin et al., 1990, Development 110:905-914; Kooh et al., 1993, Development 117:493-507). If C-Delta-1 acts similarly during chick neurogenesis, it should also be transiently expressed in neuronal precursor cells, while these are becoming determined. An analysis of C-Delta-1 expression in the developing CNS indicates that this is indeed the case.

In summary, wholemount in situ hybridization was performed. Formaldehyde fixed embryos were treated with protease and refixed with 4% formaldehyde/0.1% glutaraldehyde. Hybridization with DIG-labelled RNA probes was performed under stringent conditions (1.3×SSC, 50% formamide, 65° C., pH5) in a buffer containing 0.2% Tween-20 and 0.5% CHAPS. Washed embryos were treated with Boehringer Blocking Reagent and incubated overnight in alkaline phosphatase-coupled anti-DIG antibody. After extensive washes, embryos were stained from 30 min to overnight. The embryo in FIG. 5e was wax-sectioned after hybridization.

C-Delta-1 expression in the neural plate is first detected at stage 6-7 (31 h, 0/1 somite), in scattered cells just anterior to the presomitic mesoderm (FIG. 5b, 5c). This region gives rise to the mid/posterior hindbrain, where the earliest differentiated CNS neurons are first detected by a neurofilament antibody at stage 9 (31 h, 7-9 somites) (Sechrist & Bronner-Fraser, 1991, Neuron 7:947-963), 6h after the initial C-Delta-1 expression (Table 2).

TABLE 2

| | Hamburger-Hamilton Stage (nominal age in h; somite nos.) | | |
|---|---|---|---|
| Neural tube domains | End final S-phase | Initial C-Delta-1 expression | Initial NF expression |
| Mid/posterior Hindbrain | 4 (19 h; 0) | 6 (24 h; 0) | 9 (31 h; 7-9) |
| Spinal cord, somites 5-8 | 6 (24 h; 0) | 8 (28 h; 4-6) | 10 (36 h; 10-12) |
| Forebrain/ Midbrain | 7 (25 h; 1-3) | 8 (28 h; 4-6) | 10 (36 h; 10-12) |
| Spinal cord, somites 9-12 | 8 (28 h; 4-6) | 9 (31 h; 7-9) | 11 (43 h; 13-15) |

As neurogenesis proceeds, expression of C-Delta-1 continues to foreshadow the spatio-temporal pattern of neuronal differentiation (Table 2), spreading posteriorly along the spinal cord and anteriorly into the midbrain and forebrain (FIG. 5d, 5e). For example, the most posterior expressing cells in the stage 8 spinal cord are at the level of the prospective 6th somite, 6-8 h before the first neurons at that level express neurofilament antigen (Sechrist & Bronner-Fraser, 1991, Neuron 7:947-963) (Table 2). Table 2 shows that the appearance of C-Delta-1 expression closely follows the withdrawal of the first neuronal precursors from the division cycle and precedes the appearance of neurofilament (NF) antigen in the resultant differentiating neurons. Mid-hindbrain comprises rhombomeres 4-6, the level of the otic primordium; posterior hindbrain includes rhombomeres 7 and 8, and somites 1-4. Data for the timing of withdrawal from cell-division and for neurofilament expression are taken from Sechrist et al., 1991, Neuron 7:947-963. In all cases, C-Delta-1 is expressed in scattered cells within domains of uniform C-Notch-1 expression (FIG. 5a).

6.3. Localization and Time-Course Expression of C-Delta-1

The localization and time-course of C-Delta-1 expression indicate that the gene is switched on at an early step in neurogenesis, and that the cells expressing C-Delta-1 are prospective neurons that have not yet begun to display differentiation markers. To test this hypothesis, we made use of the observations of Sechrist and Bronner-Fraser (Sechrist & Bronner-Fraser, 1991, Neuron 7:947-963) that prospective neurons are the only non-cycling cells in the early neural tube. They finish their final S phase 11-15 h before expressing neurofilament antigen (Table 2) and their nuclei, after completing a last mitosis, adopt a characteristic location near the basal surface of the neuroepithelium, where all the other cell nuclei are in S-phase (Sechrist & Bronner-Fraser, 1991, Neuron 7:947-963; Martin & Langman, 1965, J. Embryol. Exp. Morphol. 14:23-35) (FIG. 6a). We labelled stage 7-9 embryos with bromodeoxyuridine (BrdU), and double-stained for BrdU incorporation and C-Delta-1 expression. 95% of the C-Delta-1-expressing cells were unlabelled, with their nuclei predominantly located near the basal surface, where most other nuclei were BrdU-labelled (FIG. 6b, 6c). 75 µl 0.1 mM BrdU in PBS was dropped onto stage 7-9 embryos which were incubated at 38° C. for 2-4 h before fixation for in situ hybridization. 15µm cryostat sections were hybridized with DIG-labelled RNA probes, essentially according to the method of Strähle et al. (Strähle et al., 1994, Trends In Genet. Sci. 10:75-76). After staining, slides were washed in PBS, and processed for BrdU immunodetection (Biffo et al., 1992, Histochem. Cytochem. 40:535-540). Anti-BrdU (1:1000; Sigma) was detected using FITC-coupled goat anti-mouse secondary antibody (Cappel). C-Delta-1 expression was examined by DIC microscopy, and BrdU-labelling by conventional and confocal fluorescence microscopy. These results imply that C-Delta-1 is expressed in cells that have withdrawn from the cell cycle and must indeed be prospective neurons. The few BrdU$^+$/C-Delta-1$^+$ cells have their nuclei outside the basal zone; these may be cells that finished their final S-phase soon after exposure to BrdU, moved apically to complete their final mitosis, and switched on C-Delta-1 expression. C-Delta-1 is also expressed in the later neural tube and peripheral nervous system. Again, the timing of expression and the location of the expressing cells imply that they are neuronal precursors that have not yet begun to differentiate (data not shown). Thus, C-Delta-1 expression appears to be the earliest known marker for prospective neurons.

In addition, the transcription pattern of both C-Delta-1 and C-Serrate-1 overlap that of C-Notch-1 in many regions of the embryo (data not shown) which suggest that C-Notch-1, like Notch in *Drosophila*, is a receptor for both proteins. In particular, all three genes are expressed in the neurogenic region of the developing central nervous system, and here a striking relationship is seen: the expression of both C-Serrate-1 and C-Delta-1 is confined to the domain of C-Notch-1 expression; but within this domain, the regions of C-Serrate-1 and C-Delta-1 are precisely complementary. The overlapping expression patterns suggest conservation of their functional relationship with Notch and imply that development of the chick and in particular the central nervous system involves the concerted interaction of C-Notch-1 with different ligands at different locations.

6.4. Discussion

The *Xenopus* homolog of C-Delta-1 has been cloned in a similar manner. In brief, a PCR fragment of X-Delta-1 was isolated and sequenced. This fragment was then used to identify the full length clone of X-Delta-1. The X-Delta-1 expression pattern was studied. It was shown that X-Delta-1 is expressed in scattered cells in the domain of the neural plate where primary neuronal precursors are being generated, suggesting that the cells expressing X-Delta-1 are the prospective primary neurons. In addition, X-Delta-1 is also expressed at other sites and times of neurogenesis, including the anterior neural plate and neurogenic placodes and later stages of neural tube development when secondary neurons are generated. Ectopic X-Delta-1 activity inhibited production of primary neurons; interference with endogenous X-Delta-1 activity resulted in overproduction of primary neurons. These results show that X-Delta-1 mediates lateral inhibition delivered by prospective neurons to adjacent cells. It was shown that ectopic expression of X-Delta-1 in *Xenopus* eggs suppresses primary neurogenesis, and that ectopic expression of a truncated X-Delta-1 protein which retains only two amino acids of the cytoplasmic domain interferes with endogenous signalling and leads to extra cells developing as neuronal precursors. (Chitnis et al., Nature (in press). Preliminary evidence indicates that C-Delta-1 has a similar inhibitory action when expressed in *Xenopus* embryos (data not shown). We propose that C-Delta-1, like its *Drosophila* and *Xenopus* counterparts, mediates lateral inhibition throughout neurogenesis to restrict the proportion of cells that, at any time, become committed to a neural fate. C-Delta-1 is generally expressed during neurogenesis in many other sites, in both the CNS and PNS, and, for example, the developing ear. It has been shown in the CNS that C-Notch is expressed in the ventricular zone of the E5 chick hindbrain, in dividing cells adjacent to the lumen of the neural tube. C-Delta-1 is expressed in the adjacent layer of cells, which have stopped dividing and are becoming committed as neuronal precursor cells. Thus, Delta/Notch signalling could act here, as in other neural tissues, to maintain a population of uncommitted cycling neuronal stem cells.

7. Isolation and Characterization of a Mouse Delta Homolog

A mouse Delta homolog, termed M-Delta-1, was isolated as follows:
Mouse Delta-1 gene
Tissue Origin: 8.5 and 9.5-day mouse embryonic RNA
Isolation Method:
a) random primed cDNA against above RNA
b) PCR of above cDNA using
PCR primer 1: GGITTCACITGGCCIGGIACNTT (SEQ ID NO:86) [encoding GFTWPGTF (SEQ ID NO:94), a region which is specific for Delta-, not Serrate-like proteins]
PCR primer 2: GTICCICC(G/A)TT(C/T)TT(G/A)CAIGG(G/A)TT (SEQ ID NO:87) [encoding NPCKNGGT (SEQ ID NO:88), a sequence present in many of the EGF-like repeats]
Amplification conditions: 50 ng cDNA, 1 μg each primer, 0.2 mM dNTP's, 1.8 U Taq (Perkin-Elmer) in 50 μl of supplied buffer. 40 cycles of: 94° C./30 sec, 45° C./2 min, 72° C./1 min extended by 2 sec each cycle.
The amplified fragment was an approximately 650 base pair fragment which was partially sequenced to determine its relationship to C-Delta-1.
c) a mouse 11.5 day cDNA library (Clontech) was screened. Of several positive clones, one (pMDL2; insert size approximately 4 kb) included the complete protein-coding region whose DNA sequence was completely determined.
FIGS. 7A-7B (SEQ ID NO:11) show the nucleotide sequence of the isolated clone containing M-Delta-1 DNA.
FIG. 8 (SEQ ID NO:12) shows the predicted amino acid sequence of M-Delta-1.
FIGS. 9A-9B show an amino acid alignment of the predicted amino acid sequences for M-Delta-1 and C-Delta-1. Identical amino acids are boxed showing the extensive sequence homology. The consensus sequence is shown below (SEQ ID NO:13).
Expression pattern: The expression pattern was determined to be essentially the same as that observed for C-Delta-1, in particular, in the presomitic mesoderm, central nervous system, peripheral nervous system, and kidney.

8. Isolation and Characterization of a Human Delta Homolog

A human Delta-1 homolog, termed H-Delta-1 (HDl), was isolated as follows:

A human genomic library with inserts ranging in size from 100-150 kb was probed with an EcoRI fragment of the mouse Delta-1 (M-Delta-1) gene. From the library a genomic human PAC clone was isolated which hybridized to the EcoRI fragment. Next, two degenerate oligonucleotides were used to amplify by PCR a fragment of the genomic human PAC clone. The degenerate oligos were:
5' ACIATGAA(C/T)AA(C/T)CTIGCIAA(C/T)TG (SEQ ID NO:89) [encoding TMNNLANC (SEQ ID NO:90)] and
3' AC(A/G)TAIACIGA(C/T)TG(A/G)TA(C/T)TTIGT (SEQ ID NO:91) [encoding TKYQSVYV (SEQ ID NO:92) or
3' GC(A/G/T)ATIAC(A/G)CA(C/T)TC(A/G)TC(C/T)TT (C/T)TC (SEQ ID NO:93) [encoding EKDECVIA (SEQ ID NO:25).
On the basis of the cDNA sequences for chicken and mouse Delta-1, it was expected that fragments of approximately 354 and 387 base pairs would be isolated, using the 5' and the two different 3' oligos, respectively. In fact, however, two single isolates of 525 base pairs and another that was 30 base pairs smaller, as expected, were obtained. The larger isolate was sequenced by dideoxy sequencing. The nucleotide sequence is shown in FIGS. 10A-10B (SEQ ID NO:14). Also shown in FIGS. 10A-10B are the predicted amino acid sequences of the amplified DNA fragment (SEQ ID NOS:15-22) for the three different readings frames. Due to sequencing errors, the full uninterrupted sequence between both primers was not identified. As a consequence, one cannot predict the amino acid sequence directly from the DNA sequence obtained. However, FIG. 11 shows the amino acid sequence homology between human Delta-1 (top line) (SEQ ID NO:23) and chick Delta-1 (bottom line) as determined by eye. Because of the sequencing errors, the homology was obtained by switching amongst the three different reading frames to identify the homologous regions.
Using the larger isolate (SEQ ID NO:14) as probe, a human fetal brain plasmid library (Clontech) was screened in an attempt to isolate full-length H-Delta-1 (HDl) genes. This yielded four positive plaques. Two of these positives (HDl3 and HDl24) survived rescreening and reacted positively with a large human genomic fragment on a Southern Blot. These positive clones were subcloned by digesting with EcoRI and ligating the fragments into a Bluescript KS⁻ vector. The nucleotide sequences of the inserts were obtained by dideoxy sequencing using T3 and T7 primers. The results showed that HDl24 was homologous to chicken Delta-1 at both ends; however, one end of HDl3 showed no homology. Restriction digestions with a panel of enzymes showed very similar patterns between the two clones, each of which had an insert of about 2 kb, but with differences at the 3' end of HDl3.
HDl3 and HDl24 were cut with BstXI, XbaI, HindIII and XhoI and the restriction fragments were inserted into Bluescript KS⁻, and then sequenced as described above to obtain internal sequence. The sequence that was obtained represents the 3' about 2000 bases of HDl, extending into the 3' non-coding region. HDl3 is contained within HDl24; however, the added sequence at the 5' end of HDl3 is likely due to a cloning artifact.
Since the sequence thus obtained did not contain the 5' end of HDl, HDl24 was used as a probe for subsequent hybridizations in a T cell library and in another fetal brain library (Lambda-Zap, Stratagene). A screen of the T cell library resulted in no positives. However, screening the Lambda-Zap library resulted in two positive clones, HDl13 and HDl18. These clones were inserted into a Bluescript KS⁻ vector using EcoRI as described above. The inserts were digested with a panel of restriction enzymes for comparison with HDl3 and HDl24, and the 5' and 3' ends were sequenced using T3 and T7 primers. HDl13 was determined to be only a small piece of cDNA that when sequenced showed no homology to any known Delta. However, HDl18 was 3 kb in length, and included the entire sequence of HD124 with additional 5' sequences. A set of clones were isolated using nested deletions from HDl18; these clones were then subjected to dideoxy sequencing using an automated sequencer. FIGS. 12A1-12A3 present the partial nucleotide contig sequence (SEQ ID NO:26) of human Delta obtained from clone HDl18. Due to sequencing errors, the full uninterrupted nucleotide sequence of human Delta was not determined. FIGS. 12B1-12B6 show the partial nucleotide contig sequence (SEQ ID NO:26) of human Delta (top line), with the predicted amino acid sequence in three different reading frames presented below, the second line being reading frame 1 (SEQ ID NOS: 27-42), the third line being reading frame 2 (SEQ ID NOS: 43-47), and the fourth line being reading frame 3 (SEQ ID NOS:48-64).

Sequence homology was determined by eye using the mouse Delta-1 amino acid sequence. The sequences with the greatest degree of homology to the mouse amino acid sequence are boxed in FIGS. 12B1-12B6, and represent the predicted amino acid sequence of human Delta-1. The composite resulting amino acid sequence is shown in FIGS. 14A-14B. (In FIGS. 14A-14B, the various uninterrupted portions of the human Delta sequence are assigned respectively, SEQ ID NOS:65 through 80.) Note that due to sequencing errors, the reading frame with the greatest homology is not the same throughout the sequence and shifts at positions where there are errors in the sequence.

Further, the homology determined by eye to chicken and mouse Delta indicates that the amino acid sequence deduced from the determined human Delta nucleotide sequence contains all but about the N-terminal 100-150 amino acids of human Delta-1.

FIGS. 13A-13G present the nucleotide sequence of mouse Delta-1 (top line, SEQ ID NO:4) and the contig nucleotide sequence of human Delta-1 as depicted in FIGS. 12A1-12A3 and 12B1-12B6 (second line, SEQ ID NO:26) and the nucleotide consensus sequence between mouse and human Delta (third line, SEQ ID NO:24).

Using probes containing the human Delta 5' nucleotide sequences presented in FIGS. 12A1-12A3, cDNA libraries are probed to isolate the 540 end of the human Delta gene. Primary positive clones are obtained and then confirmed as secondary positives. The secondary positives are purified and grown further. The DNA is then isolated and subcloned for sequencing.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method of treating a malignancy in a subject comprising administering to a subject in which such treatment is desired an effective amount of an antibody, or an antibody fragment, which antibody or antibody fragment (a) specifically binds to the extracellular domain of a native human Delta protein, and (b) inhibits binding of the native human Delta protein to a Notch protein; in which the native human Delta protein comprises said extracellular domain and comprises 20 continuous amino acids of SEQ ID NO:23, and binds to a Notch protein.

2. The method according to claim 1, which antibody or antibody fragment specifically binds to the region aminoterminal to the DSL domain, the DSL domain, or the epidermal growth factor-like repeat domain of the human Delta protein.

3. The method according to claim 1, in which the antibody is monoclonal.

4. The method according to claim 1, in which the antibody is polyclonal.

5. The method according to any one of claims 1, 2, 3 and 4, in which the malignancy is characterized by:
   increased Notch activity or increased expression of a Notch protein or of a Notch derivative capable of being bound by an anti-Notch antibody, relative to normal levels of Notch activity or expression.

6. The method according to any one of claims 1, 2, 3 and 4, in which the malignancy is cervical cancer, breast cancer, colon cancer, melanoma, seminoma or lung cancer.

7. The method according to any one of claims 1, 2, 3 and 4, which antibody or antibody fragment does not bind to the *Drosophila* Delta protein, the amino acid sequence of which *Drosophila* Delta protein is SEQ ID NO:6.

8. The method according to claim 5, which antibody or antibody fragment does not bind to the *Drosophila* Delta protein, the amino acid sequence of which *Drosophila* Delta protein is SEQ ID NO:6.

9. The method according to any one of claims 1, 2 and 3, in which the antibody is a human antibody.

10. The method according to any one of claims 1, 2 and 3, in which the antibody is a chimeric antibody.

11. The method according to any one of claims 1, 2 and 3, in which the subject is a human subject.

12. The method according to claim 7, in which the subject is a human subject.

13. The method according to claim 8, in which the subject is a human subject.

14. The method according to claim 9, in which the subject is a human subject.

15. The method according to claim 10, in which the subject is a human subject.

* * * * *

SEQUENCE LISTING

```
<160> NUMBER OF SEQ ID NOS: 95

<210> SEQ ID NO 1
<211> LENGTH: 2508
<212> TYPE: DNA
<213> ORGANISM: Gallus gallus
<220> FEATURE:
<221> NAME/KEY: CDS
<222> LOCATION: (277)...(2460)
<223> OTHER INFORMATION: Chick Delta (C-Delta-1) gene

<400> SEQUENCE: 1
gaattcggca cgaggttttt tttttttttt ttccctctt ttctttcttt tccttttgcc      60
atccgaaaga gctgtcagcc gccgccgggc tgcacctaaa ggcgtcggta gggggataac     120
agtcagagac cctcctgaaa gcaggagacg ggacggtacc cctccggctc tgcggggcgg    180
ctgcggcccc tccgttcttt cccctcccc gagagacact cttcctttcc ccccacgaag     240
acacaggggc aggaacgcga gcgctgcccc tccgcc atg gga ggc cgc ttc ctg     294
                                         Met Gly Gly Arg Phe Leu
                                         1               5 ctg acg ctc gcc ctc ctc tcg gcg ctg ctg tgc cgc tgc cag gtt gac     342
Leu Thr Leu Ala Leu Leu Ser Ala Leu Leu Cys Arg Cys Gln Val Asp
            10                  15                  20 ggc tcc ggg gtg ttc gag ctg aag ctg cag gag ttt gtc aac aag aag     390
Gly Ser Gly Val Phe Glu Leu Lys Leu Gln Glu Phe Val Asn Lys Lys
        25                  30                  35 ggg ctg ctc agc aac cgc aac tgc tgc cgg ggg ggc ggc ccc gga ggc     438
Gly Leu Leu Ser Asn Arg Asn Cys Cys Arg Gly Gly Gly Pro Gly Gly
    40                  45                  50 gcc ggg cag cag cag tgc gac tgc aag acc ttc ttc cgc gtc tgc ctg     486
Ala Gly Gln Gln Gln Cys Asp Cys Lys Thr Phe Phe Arg Val Cys Leu
55                  60                  65                  70
```

| | | |
|---|---|---|
| aag cac tac cag gcc agc gtc tcc ccc gag ccg ccc tgc acc tac ggc<br>Lys His Tyr Gln Ala Ser Val Ser Pro Glu Pro Pro Cys Thr Tyr Gly<br>75 80 85 | 534 | |
| agc gcc atc acc ccc gtc ctc ggc gcc aac tcc ttc agc gtc ccc gac<br>Ser Ala Ile Thr Pro Val Leu Gly Ala Asn Ser Phe Ser Val Pro Asp<br>90 95 100 | 582 | |
| ggc gcg ggc ggc gcc gac ccc gcc ttc agc aac ccc atc cgc ttc ccc<br>Gly Ala Gly Gly Ala Asp Pro Ala Phe Ser Asn Pro Ile Arg Phe Pro<br>105 110 115 | 630 | |
| ttc ggc ttc acc tgg ccc ggc acc ttc tcg ctc atc atc gag gct ctg<br>Phe Gly Phe Thr Trp Pro Gly Thr Phe Ser Leu Ile Ile Glu Ala Leu<br>120 125 130 | 678 | |
| cac acc gac tcc ccc gac gac ctc acc aca gaa aac ccc gag cgc ctc<br>His Thr Asp Ser Pro Asp Asp Leu Thr Thr Glu Asn Pro Glu Arg Leu<br>135 140 145 150 | 726 | |
| atc agc cgc ctg gcc acc cag agg cac ctg gcg gtg ggc gag gag tgg<br>Ile Ser Arg Leu Ala Thr Gln Arg His Leu Ala Val Gly Glu Glu Trp<br>155 160 165 | 774 | |
| tcc cag gac ctg cac agc agc ggc cgc acc gac ctc aag tac tcc tat<br>Ser Gln Asp Leu His Ser Ser Gly Arg Thr Asp Leu Lys Tyr Ser Tyr<br>170 175 180 | 822 | |
| cgc ttt gtg tgt gat gag cac tac tac ggg gaa ggc tgc tct gtc ttc<br>Arg Phe Val Cys Asp Glu His Tyr Tyr Gly Glu Gly Cys Ser Val Phe<br>185 190 195 | 870 | |
| tgc cgg ccc cgt gac gac cgc ttc ggt cac ttc acc tgt gga gag cgt<br>Cys Arg Pro Arg Asp Asp Arg Phe Gly His Phe Thr Cys Gly Glu Arg<br>200 205 210 | 918 | |
| ggc gag aag gtc tgc aac cca ggc tgg aag ggc cag tac tgc act gag<br>Gly Glu Lys Val Cys Asn Pro Gly Trp Lys Gly Gln Tyr Cys Thr Glu<br>215 220 225 230 | 966 | |
| ccg att tgc ttg cct ggg tgt gac gag cag cac ggc ttc tgc gac aaa<br>Pro Ile Cys Leu Pro Gly Cys Asp Glu Gln His Gly Phe Cys Asp Lys<br>235 240 245 | 1014 | |
| cct ggg gaa tgc aag tgc aga gtg ggt tgg cag ggg cgg tac tgt gac<br>Pro Gly Glu Cys Lys Cys Arg Val Gly Trp Gln Gly Arg Tyr Cys Asp<br>250 255 260 | 1062 | |
| gag tgc atc cga tac cca ggc tgc ctg cac ggt acc tgt cag cag cca<br>Glu Cys Ile Arg Tyr Pro Gly Cys Leu His Gly Thr Cys Gln Gln Pro<br>265 270 275 | 1110 | |
| tgg cag tgc aac tgc cag gaa ggc tgg ggc ggc ctt ttc tgc aac cag<br>Trp Gln Cys Asn Cys Gln Glu Gly Trp Gly Gly Leu Phe Cys Asn Gln<br>280 285 290 | 1158 | |
| gac ctg aac tac tgc act cac cac aag cca tgc aag aat ggt gcc aca<br>Asp Leu Asn Tyr Cys Thr His His Lys Pro Cys Lys Asn Gly Ala Thr<br>295 300 305 310 | 1206 | |
| tgc acc aac acc ggt cag ggg agc tac act tgt tct tgc cga cct ggg<br>Cys Thr Asn Thr Gly Gln Gly Ser Tyr Thr Cys Ser Cys Arg Pro Gly<br>315 320 325 | 1254 | |
| tac aca ggc tcc agc tgc gag att gaa atc aac gaa tgt gat gcc aac<br>Tyr Thr Gly Ser Ser Cys Glu Ile Glu Ile Asn Glu Cys Asp Ala Asn<br>330 335 340 | 1302 | |
| cct tgc aag aat ggt gga agc tgc acg gat ctc gag aac agc tat tcc<br>Pro Cys Lys Asn Gly Gly Ser Cys Thr Asp Leu Glu Asn Ser Tyr Ser<br>345 350 355 | 1350 | |
| tgt acc tgc ccc cca ggc ttc tat ggt aaa aac tgt gag ctg agt gca<br>Cys Thr Cys Pro Pro Gly Phe Tyr Gly Lys Asn Cys Glu Leu Ser Ala<br>360 365 370 | 1398 | |
| atg act tgt gct gat gga ccg tgc ttc aat gga ggg cga tgc act gac<br>Met Thr Cys Ala Asp Gly Pro Cys Phe Asn Gly Gly Arg Cys Thr Asp<br>375 380 385 390 | 1446 | |

```
aac cct gat ggt gga tac agc tgc cgc tgc cca ctg ggt tat tct ggg      1494
Asn Pro Asp Gly Gly Tyr Ser Cys Arg Cys Pro Leu Gly Tyr Ser Gly
            395                 400                 405 ttc aac tgt gaa aag aaa atc gat tac tgc agt tcc agc cct tgt gct      1542
Phe Asn Cys Glu Lys Lys Ile Asp Tyr Cys Ser Ser Ser Pro Cys Ala
        410                 415                 420 aat gga gcc cag tgc gtt gac ctg ggg aac tcc tac ata tgc cag tgc      1590
Asn Gly Ala Gln Cys Val Asp Leu Gly Asn Ser Tyr Ile Cys Gln Cys
    425                 430                 435 cag gct ggc ttc act ggc agg cac tgt gac gac aac gtg gac gat tgc      1638
Gln Ala Gly Phe Thr Gly Arg His Cys Asp Asp Asn Val Asp Asp Cys
440                 445                 450 gcc tcc ttc ccc tgc gtc aat gga ggg acc tgt cag gat ggg gtc aac      1686
Ala Ser Phe Pro Cys Val Asn Gly Gly Thr Cys Gln Asp Gly Val Asn
455                 460                 465                 470 gac tac tcc tgc acc tgc ccc ccg gga tac aac ggg aag aac tgc agc      1734
Asp Tyr Ser Cys Thr Cys Pro Pro Gly Tyr Asn Gly Lys Asn Cys Ser
            475                 480                 485 acg ccg gtg agc aga tgc gag cac aac ccc tgc cac aat ggg gcc acc      1782
Thr Pro Val Ser Arg Cys Glu His Asn Pro Cys His Asn Gly Ala Thr
        490                 495                 500 tgc cac gag aga agc aac cgc tac gtg tgc gag tgc gct cgg ggc tac      1830
Cys His Glu Arg Ser Asn Arg Tyr Val Cys Glu Cys Ala Arg Gly Tyr
    505                 510                 515 ggc ggc ctc aac tgc cag ttc ctg ctc ccc gag cca cct cag ggg ccg      1878
Gly Gly Leu Asn Cys Gln Phe Leu Leu Pro Glu Pro Pro Gln Gly Pro
520                 525                 530 gtc atc gtt gac ttc acc gag aag tac aca gag ggc cag aac agc cag      1926
Val Ile Val Asp Phe Thr Glu Lys Tyr Thr Glu Gly Gln Asn Ser Gln
535                 540                 545                 550 ttt ccc tgg atc gca gtg tgc gcc ggg att att ctg gtc ctc atg ctg      1974
Phe Pro Trp Ile Ala Val Cys Ala Gly Ile Ile Leu Val Leu Met Leu
            555                 560                 565 ctg ctg ggt tgc gcc gcc atc gtc gtc tgc gtc agg ctg aag gtg cag      2022
Leu Leu Gly Cys Ala Ala Ile Val Val Cys Val Arg Leu Lys Val Gln
        570                 575                 580 aag agg cac cac cag ccc gag gcc tgc agg agt gaa acg gag acc atg      2070
Lys Arg His His Gln Pro Glu Ala Cys Arg Ser Glu Thr Glu Thr Met
    585                 590                 595 aac aac ctg gcg aac tgc cag cgc gag aag gac atc tcc atc agc gtc      2118
Asn Asn Leu Ala Asn Cys Gln Arg Glu Lys Asp Ile Ser Ile Ser Val
600                 605                 610 atc ggt gcc act cag att aaa aac aca aat aag aaa gta gac ttt cac      2166
Ile Gly Ala Thr Gln Ile Lys Asn Thr Asn Lys Lys Val Asp Phe His
615                 620                 625                 630 agc gat aac tcc gat aaa aac ggc tac aaa gtt aga tac cca tca gtg      2214
Ser Asp Asn Ser Asp Lys Asn Gly Tyr Lys Val Arg Tyr Pro Ser Val
            635                 640                 645 gat tac aat ttg gtg cat gaa ctc aag aat gag gac tct gtg aaa gag      2262
Asp Tyr Asn Leu Val His Glu Leu Lys Asn Glu Asp Ser Val Lys Glu
        650                 655                 660 gag cat ggc aaa tgc gaa gcc aag tgt gaa acg tat gat tca gag gca      2310
Glu His Gly Lys Cys Glu Ala Lys Cys Glu Thr Tyr Asp Ser Glu Ala
    665                 670                 675 gaa gag aaa agc gca gta cag cta aaa agt agt gac act tct gaa aga      2358
Glu Glu Lys Ser Ala Val Gln Leu Lys Ser Ser Asp Thr Ser Glu Arg
680                 685                 690 aaa cgg cca gat tca gta tat tcc act tca aag gac aca aag tac cag      2406
Lys Arg Pro Asp Ser Val Tyr Ser Thr Ser Lys Asp Thr Lys Tyr Gln
695                 700                 705                 710
```

```
tcg gtg tac gtc ata tca gaa gag aaa gat gag tgc atc ata gca act    2454
Ser Val Tyr Val Ile Ser Glu Glu Lys Asp Glu Cys Ile Ile Ala Thr
            715                 720                 725 gag gtg taaaacagac gtgacgtggc aaagcttatc gataccgtca tcaagctt       2508
Glu Val
```

<210> SEQ ID NO 2
<211> LENGTH: 728
<212> TYPE: PRT
<213> ORGANISM: Gallus gallus

<400> SEQUENCE: 2

```
Met Gly Gly Arg Phe Leu Leu Thr Leu Ala Leu Leu Ser Ala Leu Leu
1               5                   10                  15

Cys Arg Cys Gln Val Asp Gly Ser Gly Val Phe Glu Leu Lys Leu Gln
            20                  25                  30

Glu Phe Val Asn Lys Lys Gly Leu Leu Ser Asn Arg Asn Cys Cys Arg
        35                  40                  45

Gly Gly Gly Pro Gly Gly Ala Gly Gln Gln Gln Cys Asp Cys Lys Thr
    50                  55                  60

Phe Phe Arg Val Cys Leu Lys His Tyr Gln Ala Ser Val Ser Pro Glu
65                  70                  75                  80

Pro Pro Cys Thr Tyr Gly Ser Ala Ile Thr Pro Val Leu Gly Ala Asn
                85                  90                  95

Ser Phe Ser Val Pro Asp Gly Ala Gly Gly Ala Asp Pro Ala Phe Ser
            100                 105                 110

Asn Pro Ile Arg Phe Pro Phe Gly Phe Thr Trp Pro Gly Thr Phe Ser
        115                 120                 125

Leu Ile Ile Glu Ala Leu His Thr Asp Ser Pro Asp Asp Leu Thr Thr
    130                 135                 140

Glu Asn Pro Glu Arg Leu Ile Ser Arg Leu Ala Thr Gln Arg His Leu
145                 150                 155                 160

Ala Val Gly Glu Glu Trp Ser Gln Asp Leu His Ser Ser Gly Arg Thr
                165                 170                 175

Asp Leu Lys Tyr Ser Tyr Arg Phe Val Cys Asp Glu His Tyr Tyr Gly
            180                 185                 190

Glu Gly Cys Ser Val Phe Cys Arg Pro Arg Asp Asp Arg Phe Gly His
        195                 200                 205

Phe Thr Cys Gly Glu Arg Gly Glu Lys Val Cys Asn Pro Gly Trp Lys
    210                 215                 220

Gly Gln Tyr Cys Thr Glu Pro Ile Cys Leu Pro Gly Cys Asp Glu Gln
225                 230                 235                 240

His Gly Phe Cys Asp Lys Pro Gly Glu Cys Lys Cys Arg Val Gly Trp
                245                 250                 255

Gln Gly Arg Tyr Cys Asp Glu Cys Ile Arg Tyr Pro Gly Cys Leu His
            260                 265                 270

Gly Thr Cys Gln Gln Pro Trp Gln Cys Asn Cys Gln Glu Gly Trp Gly
        275                 280                 285

Gly Leu Phe Cys Asn Gln Asp Leu Asn Tyr Cys Thr His His Lys Pro
    290                 295                 300

Cys Lys Asn Gly Ala Thr Cys Thr Asn Thr Gly Gln Gly Ser Tyr Thr
305                 310                 315                 320

Cys Ser Cys Arg Pro Gly Tyr Thr Gly Ser Ser Cys Glu Ile Glu Ile
                325                 330                 335

Asn Glu Cys Asp Ala Asn Pro Cys Lys Asn Gly Gly Ser Cys Thr Asp
```

```
                    340                 345                 350
Leu Glu Asn Ser Tyr Ser Cys Thr Cys Pro Gly Phe Tyr Gly Lys
            355                 360                 365
Asn Cys Glu Leu Ser Ala Met Thr Cys Ala Asp Gly Pro Cys Phe Asn
        370                 375                 380
Gly Gly Arg Cys Thr Asp Asn Pro Asp Gly Gly Tyr Ser Cys Arg Cys
385                 390                 395                 400
Pro Leu Gly Tyr Ser Gly Phe Asn Cys Glu Lys Lys Ile Asp Tyr Cys
                405                 410                 415
Ser Ser Ser Pro Cys Ala Asn Gly Ala Gln Cys Val Asp Leu Gly Asn
            420                 425                 430
Ser Tyr Ile Cys Gln Cys Gln Ala Gly Phe Thr Gly Arg His Cys Asp
        435                 440                 445
Asp Asn Val Asp Asp Cys Ala Ser Phe Pro Cys Val Asn Gly Gly Thr
    450                 455                 460
Cys Gln Asp Gly Val Asn Asp Tyr Ser Cys Thr Cys Pro Pro Gly Tyr
465                 470                 475                 480
Asn Gly Lys Asn Cys Ser Thr Pro Val Ser Arg Cys Glu His Asn Pro
                485                 490                 495
Cys His Asn Gly Ala Thr Cys His Glu Arg Ser Asn Arg Tyr Val Cys
            500                 505                 510
Glu Cys Ala Arg Gly Tyr Gly Gly Leu Asn Cys Gln Phe Leu Leu Pro
        515                 520                 525
Glu Pro Pro Gln Gly Pro Val Ile Val Asp Phe Thr Glu Lys Tyr Thr
    530                 535                 540
Glu Gly Gln Asn Ser Gln Phe Pro Trp Ile Ala Val Cys Ala Gly Ile
545                 550                 555                 560
Ile Leu Val Leu Met Leu Leu Leu Gly Cys Ala Ala Ile Val Val Cys
                565                 570                 575
Val Arg Leu Lys Val Gln Lys Arg His His Gln Pro Glu Ala Cys Arg
            580                 585                 590
Ser Glu Thr Glu Thr Met Asn Asn Leu Ala Asn Cys Gln Arg Glu Lys
        595                 600                 605
Asp Ile Ser Ile Ser Val Ile Gly Ala Thr Gln Ile Lys Asn Thr Asn
    610                 615                 620
Lys Lys Val Asp Phe His Ser Asp Asn Ser Asp Lys Asn Gly Tyr Lys
625                 630                 635                 640
Val Arg Tyr Pro Ser Val Asp Tyr Asn Leu Val His Glu Leu Lys Asn
                645                 650                 655
Glu Asp Ser Val Lys Glu Glu His Gly Lys Cys Glu Ala Lys Cys Glu
            660                 665                 670
Thr Tyr Asp Ser Glu Ala Glu Lys Ser Ala Val Gln Leu Lys Ser
        675                 680                 685
Ser Asp Thr Ser Glu Arg Lys Arg Pro Asp Ser Val Tyr Ser Thr Ser
    690                 695                 700
Lys Asp Thr Lys Tyr Gln Ser Val Tyr Val Ile Ser Glu Glu Lys Asp
705                 710                 715                 720
Glu Cys Ile Ile Ala Thr Glu Val
                725

<210> SEQ ID NO 3
<211> LENGTH: 2883
<212> TYPE: DNA
<213> ORGANISM: Gallus gallus
<220> FEATURE:
```

<223> OTHER INFORMATION: Alternatively spliced chick Delta (C-Delta-1) gene

<400> SEQUENCE: 3

```
gaattcggca cgaggttttt tttttttttt ttccctctct ttctttcttt tccttttgcc      60
atccgaaaga gctgtcagcc gccgccgggc tgcacctaaa ggcgtcggta gggggataac     120
agtcagagac cctcctgaaa gcaggagacg ggacggtacc cctccggctc tgcggggcgg     180
ctgcggcccc tccgttcttt cccctcccc gagagacact cttcctttcc ccccacgaag      240
acacaggggc aggaacgcga gcgctgcccc tccgccatgg gaggccgctt cctgctgacg     300
ctcgccctcc tctcggcgct gctgtgccgc tgccaggttg acggctccgg ggtgttcgag     360
ctgaagctgc aggagtttgt caacaagaag gggctgctca gcaaccgcaa ctgctgccgg     420
ggggcggcc ccggaggcgc cgggcagcag cagtgcgact gcaagacctt cttccgcgtc      480
tgcctgaagc actaccaggc cagcgtctcc cccgagccgc cctgcaccta cggcagcgcc     540
atcaccccg tcctcggcgc caactccttc agcgtccccg acggcgcggg cggcgccgac      600
cccgccttca gcaaccccat ccgcttcccc ttcggcttca cctggccgg caccttctcg      660
ctcatcatcg aggctctgca caccgactcc ccgacgacc tcaccacaga aaaccccgag      720
cgcctcatca gccgcctggc cacccagagg cacctggcgg tgggcgagga gtggtcccag     780
gacctgcaca gcagcggccg caccgacctc aagtactcct atcgctttgt gtgtgatgag     840
cactactacg gggaaggctg ctctgtcttc tgccggcccc gtgacgaccg cttcggtcac     900
ttcacctgtg gagagcgtgg cgagaaggtc tgcaacccag gctggaaggg ccagtactgc     960
actgagccga tttgcttgcc tgggtgtgac gagcagcacg gcttctgcga caaacctggg    1020
gaatgcaagt gcagagtggg ttggcagggg cggtactgtg acgagtgcat ccgatatccca   1080
ggctgcctgc acggtacctg tcagcagcca tggcagtgca actgccagga aggctggggc    1140
ggccttttct gcaaccagga cctgaactac tgcactcacc acaagccatg caagaatggt    1200
gccacatgca ccaacaccgg tcaggggagc tacacttgtt cttgccgacc tgggtacaca    1260
ggctccagct gcgagattga aatcaacgaa tgtgatgcca accttgcaa gaatggtgga    1320
agctgcacgg atctcgagaa cagctattcc tgtacctgcc ccccaggctt ctatggtaaa    1380
aactgtgagc tgagtgcaat gacttgtgct gatggaccgt gcttcaatgg agggcgatgc    1440
actgacaacc ctgatggtgg atacagctgc cgctgcccac tgggttattc tgggttcaac    1500
tgtgaaaaga aaatcgatta ctgcagttcc agcccttgtg ctaatggagc ccagtgcgtt    1560
gacctgggga actcctacat atgccagtgc caggctggct tcactggcag gcactgtgac    1620
gacaacgtgg acgattgcgc ctccttcccc tgcgtcaatg gagggacctg tcaggatggg    1680
gtcaacgact actcctgcac ctgcccccg ggatacaacg gaagaactg cagcacgccg      1740
gtgagcagat gcgagcacaa cccctgccac aatggggcca cctgccacga gaagcaac      1800
cgctacgtgt gcgagtgcgc tcggggctac ggcggcctca actgccagtt cctgctcccc    1860
gagccacctc aggggccggt catcgttgac ttcaccgaga agtacacaga gggccagaac    1920
agccagtttc cctggatcgc agtgtgcgcc gggattattc tggtcctcat gctgctgctg    1980
ggttgcgccg ccatcgtcgt ctgcgtcagg ctgaaggtgc agaagaggca ccaccagccc    2040
gaggcctgca ggagtgaaac ggagaccatg aacaacctgg cgaactgcca gcgcgagaag    2100
gacatctcca tcagcgtcat cggtgccact cagattaaaa acacaaataa gaaagtagac    2160
tttcacagcg ataactccga taaaaacggc tacaaagtta gatacccatc agtggattac    2220
aatttggtgc atgaactcaa gaatgaggac tctgtgaaag aggagcatgg caaatgcgaa    2280
```

-continued

```
gccaagtgtg aaacgtatga ttcagaggca gaagagaaaa gcgcagtaca gctaaaaagt    2340
agtgacactt ctgaaagaaa acggccagat tcagtatatt ccacttcaaa ggacacaaag    2400
taccagtcgg tgtacgtcat atcagaagag aaagatgagt gcatcatagc aactgaggtt    2460
agtatcccac ctggcagtcg gacaagtctt ggtgtgtgat tcccatccag cgcaggtcag    2520
ggcggccaaa ccattctacc tgctgccaca gtcatctgta cccaatgaaa actggccacc    2580
ttcagtctgt ggcactgcag acgttgaaaa aacttgttgt ggattaacat aagctccagt    2640
gggggttaca gggacagcaa ttttttgcagg caagggtata actgtagtgc agttgtagct    2700 tactaacccct actgactcat tctttcgtgt gcttcctgca gagcctgttt ttgcttggca    2760
ttgaggtgaa gtcctgaccc tctgcatcct catagtcctc tgctttcttt ttattaacct    2820
cttctggtct ctgcttgtct tttctctcaa caggtgtaaa acagacgtga cgtggcaaag    2880
ctt                                                                  2883
```

<210> SEQ ID NO 4
<211> LENGTH: 2857
<212> TYPE: DNA
<213> ORGANISM: mouse
<220> FEATURE:
<223> OTHER INFORMATION: mouse Delta-1 gene

<400> SEQUENCE: 4

```
gtccagcggt accatgggcc gtcggagcgc gctaccccctt gccgtggtct ctgccctgct     60
gtgccaggtc tggagctccg gcgtatttga gctgaagctg caggagttcg tcaacaagaa    120
ggggctgctg ggaaccgca actgctgccg cggggggctct ggcccgcctt cgcctgcag     180 gaccttcttt cgcgtatgcc tcaaccacta ccaggccagc gtgtcaccgg agccaccctg    240
cacctacggc agtgctgtca cgccagtgct gggtctcgac tccttcagcc tgcctgatgg    300
cgcaggcatc gacccccgcct tcagcaaccc atccgattcc ccttccggct tcacctggcc    360
aggtaccttc tctctgatca ttgaagccct ccatacagac tctcccgatg acctcgcaac    420
agaaaaccca gaaagactca tcagccgcct gaccacacag aggcacctca ctgtgggacg    480
aatggtctca ggaccttcac agtagcggcc gcacagacct ccggtactct taccggtttg    540
tgtgtgacga gcactactac ggagaaggtt gctctgtgtt ctgccgacct cgggatgacg    600 ccttggggcca cttcacctgc ggggacagag gggagaagat gtgcgaccct ggctggaaag    660
gccagtactg cactgaccca atctgtctgc agggtgtga tgaccaacat ggatactgtg    720
acaaaccagg ggagtgcaag tgcagagttg gctggcaggg ccgctactgc gatgagtgca    780
tccgataccc aggttgtctc catggcacct gccagcaacc ctggcagtgt aactgccagg    840
aaggctgggg gggccttttc tgcaaccaag acctgaacta ctgtactcac cataagccgt    900
gcaggaatgg agccacctgc accaacacgg ccaggggag ctacacatgt tcctgccgac    960
tggggtatac aggtgccaac tgtgagctgg aagtagatga gtgtgctcct agccctgca   1020 agaacggagc gagctgcacg gaccttgagg acagcttctc ttgcacctgc cctcccggct   1080
tctatggcaa ggtctgtgag cttgagcgcc atgacctgtg cagatggccc ttgcttcaat   1140
ggaggacgat gttcagataa ccctgacgga ggctacacct gccattgccc cttgggcttc   1200
tctggcttca actgtgagaa gaagatggat ctctgcggct cttccccctt gttctaacgg   1260
tgccaagtgt gtggaccctcg gcaactctta cctgtgccgg tgccaggctg gcttctccgg   1320
gacctactgc gaggacaatg tggatgactg tgcctcctcc ccgtgtgcaa atggggggcac   1380 ctgccgggac agtgtgaacg acttctcctc tacctgccca cctggctaca cgggcaagaa   1440
```

```
ctgcagcgcc cctgtcagca ggtgtgagca tgcaccctgc cataatgggg ccacctgcca      1500 ccagagggc cagcgctaca tgtgtgagtg cgcccagggc tatggcggcc ccaactgcca       1560
gtttctgctc cctgagccac caccagggcc catggtggtg acctcagtg agaggcatat        1620 ggagagccag ggcgggccct tcccctcggt ggcggtgtgt gccggggtgg tgcttgtcct      1680
cctgctgctg ctgggctgtg ctgctgtggt ggtctgcgtc cggctgaagc tacagaaaca      1740
ccagcctcca cctgaaccct gtgggggaga gacagaaacc atgaacaacc tagccaattg      1800
ccagcgcgag aaggacgttt ctgttagcat cattggggct acccagatca agaacaccaa      1860
caagaaggcg gactttcacg gggaccatgg agccaagaag agcagcttta aggtccgata      1920
ccccactgtg gactataacc tcgttcgaga cctcaaggga gatgaagcca cggtcaggga     1980
tacacacagc aaacgtgaca ccaagtgcca gtcacagagc tctgcaggag aagagaagat     2040
cgccccaaca cttaggggtg gggagattcc tgacagaaaa aggccagagt ctgtctactc      2100
tacttcaaag gacaccaagt accagtcggt gtatgttctg tctgcagaaa aggatgagtg       2160
tgttatagcg actgagctgt aagatggaag cgatgtggca aaattcccat ttctctcaaa       2220
taaaattcca aggatatagc cccgatgaat gctgctgaga gaggaaggga gaggaaaccc     2280
agggactgct gctgagaacc aggttcaggc gaagctggtt ctctcagagt tagcagaggc       2340
gcccgacact gccagcctag gctttggctg ccgctggact gcctgctggt tgttcccatt       2400
gcactatgga cagttgctt gaagagtata tatttaaatg gacgagtgac ttgattcata       2460
tacgaagcac gcactgccca cacgtctatc ttggattact atgagccagt ctttccttga       2520
actagaaaca caactgcctt tattgtcctt tttgatactg agatgtgttt ttttttttcc       2580
tagacgggaa aaagaaaacg tgtgttattt ttttgggatt tgtaaaaata ttttttcatga     2640 tatctgtaaa gcttgagtat tttgtgacgt tcattttttt ataatttaaa ttttggtaaa      2700
tatgtacaaa ggcacttcgg gtctatgtga ctatattttt ttgtatataa atgtatttat      2760
ggaatattgt gcaaatgtta tttgagtttt ttactgtttt gttaatgaag aaattcattt      2820
taaaaatatt tttccaaaat aaatataatg aactaca                              2857
```

<210> SEQ ID NO 5
<211> LENGTH: 721
<212> TYPE: PRT
<213> ORGANISM: Xenopus

<400> SEQUENCE: 5

Met Gly Gln Gln Arg Met Leu Thr Leu Leu Val Leu Ser Ala Val Leu
1               5                   10                  15

Cys Gln Ile Ser Cys Ser Gly Leu Phe Glu Leu Arg Leu Gln Glu Phe
            20                  25                  30

Val Asn Lys Lys Gly Leu Leu Gly Asn Met Asn Cys Cys Arg Pro Gly
        35                  40                  45

Ser Leu Ala Ser Leu Gln Arg Cys Glu Cys Lys Thr Phe Phe Arg Ile
    50                  55                  60

Cys Leu Lys His Tyr Gln Ser Asn Val Ser Pro Glu Pro Pro Cys Thr
65                  70                  75                  80

Tyr Gly Gly Ala Val Thr Pro Val Leu Gly Thr Asn Ser Phe Val Val
                85                  90                  95

Pro Glu Ser Ser Asn Ala Asp Pro Thr Phe Ser Asn Pro Ile Arg Phe
            100                 105                 110

Pro Phe Gly Phe Thr Trp Pro Gly Thr Phe Ser Leu Ile Ile Glu Ala
        115                 120                 125

```
Ile His Ala Asp Ser Ala Asp Asp Leu Asn Thr Glu Asn Pro Glu Arg
    130                 135                 140

Leu Ile Ser Arg Leu Ala Thr Gln Arg His Leu Thr Val Gly Glu Gln
145                 150                 155                 160

Trp Ser Gln Asp Leu His Ser Ser Asp Arg Thr Glu Leu Lys Tyr Ser
                    165                 170                 175

Tyr Arg Phe Val Cys Asp Glu Tyr Tyr Gly Glu Gly Cys Ser Asp
                180                 185                 190

Tyr Cys Arg Pro Arg Asp Asp Ala Phe Gly His Phe Ser Cys Gly Glu
        195                 200                 205

Lys Gly Glu Lys Leu Cys Asn Pro Gly Trp Lys Gly Leu Tyr Cys Thr
210                 215                 220

Glu Pro Ile Cys Leu Pro Gly Cys Asp Glu His Gly Tyr Cys Asp
225                 230                 235                 240

Lys Pro Gly Glu Cys Lys Cys Arg Val Gly Trp Gln Gly Arg Tyr Cys
                    245                 250                 255

Asp Glu Cys Ile Arg Tyr Pro Gly Cys Leu His Gly Thr Cys Gln Gln
                260                 265                 270

Pro Trp Gln Cys Asn Cys Gln Glu Gly Trp Gly Gly Leu Phe Cys Asn
            275                 280                 285

Gln Asp Leu Asn Tyr Cys Thr His His Lys Pro Cys Glu Asn Gly Ala
    290                 295                 300

Thr Cys Thr Asn Thr Gly Gln Gly Ser Tyr Thr Cys Ser Cys Arg Pro
305                 310                 315                 320

Gly Tyr Thr Gly Ser Asn Cys Glu Ile Glu Val Asn Glu Cys Asp Ala
                325                 330                 335

Asn Pro Cys Lys Asn Gly Gly Ser Cys Ser Asp Leu Glu Asn Ser Tyr
            340                 345                 350

Thr Cys Ser Cys Pro Pro Gly Phe Tyr Gly Lys Asn Cys Glu Leu Ser
        355                 360                 365

Ala Met Thr Cys Ala Asp Gly Pro Cys Phe Asn Gly Gly Arg Cys Ala
    370                 375                 380

Asp Asn Pro Asp Gly Gly Tyr Ile Cys Phe Cys Pro Val Gly Tyr Ser
385                 390                 395                 400

Gly Phe Asn Cys Glu Lys Lys Ile Asp Tyr Cys Ser Ser Asn Pro Cys
                405                 410                 415

Ala Asn Gly Ala Arg Cys Glu Asp Leu Gly Asn Ser Tyr Ile Cys Gln
            420                 425                 430

Cys Gln Glu Gly Phe Ser Gly Arg Asn Cys Asp Asp Asn Leu Asp Asp
        435                 440                 445

Cys Thr Ser Phe Pro Cys Gln Asn Gly Gly Thr Cys Gln Asp Gly Ile
    450                 455                 460

Asn Asp Tyr Ser Cys Thr Cys Pro Pro Gly Tyr Ile Gly Lys Asn Cys
465                 470                 475                 480

Ser Met Pro Ile Thr Lys Cys Glu His Asn Pro Cys His Asn Gly Ala
                485                 490                 495

Thr Cys His Glu Arg Asn Asn Arg Tyr Val Cys Gln Cys Ala Arg Gly
            500                 505                 510

Tyr Gly Gly Asn Asn Cys Gln Phe Leu Leu Pro Glu Glu Lys Pro Val
        515                 520                 525

Val Val Asp Leu Thr Glu Lys Tyr Thr Glu Gly Gln Ser Gly Gln Phe
    530                 535                 540

Pro Trp Ile Ala Val Cys Ala Gly Ile Val Leu Val Leu Met Leu Leu
```

```
                        545                 550                 555                 560
Leu Gly Cys Ala Ala Val Val Cys Val Arg Val Arg Val Gln Lys
                    565                 570                 575

Arg Arg His Gln Pro Glu Ala Cys Arg Gly Glu Ser Lys Thr Met Asn
                580                 585                 590

Asn Leu Ala Asn Cys Gln Arg Glu Lys Asp Ile Ser Val Ser Phe Ile
            595                 600                 605

Gly Thr Thr Gln Ile Lys Asn Thr Asn Lys Lys Ile Asp Phe Leu Ser
        610                 615                 620

Glu Ser Asn Asn Glu Lys Asn Gly Tyr Lys Pro Arg Tyr Pro Ser Val
625                 630                 635                 640

Asp Tyr Asn Leu Val His Glu Leu Lys Asn Glu Asp Ser Pro Lys Glu
                645                 650                 655

Glu Arg Ser Lys Cys Glu Ala Lys Cys Ser Ser Asn Asp Ser Asp Ser
                660                 665                 670

Glu Asp Val Asn Ser Val His Ser Lys Arg Asp Ser Ser Glu Arg Arg
            675                 680                 685

Arg Pro Asp Ser Ala Tyr Ser Thr Ser Lys Asp Thr Lys Tyr Gln Ser
        690                 695                 700

Val Tyr Val Ile Ser Asp Glu Lys Asp Glu Cys Ile Ile Ala Thr Glu
705                 710                 715                 720

Val

<210> SEQ ID NO 6
<211> LENGTH: 832
<212> TYPE: PRT
<213> ORGANISM: Drosophila

<400> SEQUENCE: 6

Met His Trp Ile Lys Cys Leu Leu Thr Ala Phe Ile Cys Phe Thr Val
1               5                   10                  15

Ile Val Gln Val His Ser Ser Gly Ser Phe Glu Leu Arg Leu Lys Tyr
                20                  25                  30

Phe Ser Asn Asp His Gly Arg Asp Asn Glu Gly Arg Cys Cys Ser Gly
            35                  40                  45

Glu Ser Asp Gly Ala Thr Gly Lys Cys Leu Gly Ser Cys Lys Thr Arg
        50                  55                  60

Phe Arg Leu Cys Leu Lys His Tyr Gln Ala Thr Ile Asp Thr Thr Ser
65                  70                  75                  80

Gln Cys Thr Tyr Gly Asp Val Ile Thr Pro Ile Leu Gly Glu Asn Ser
                85                  90                  95

Val Asn Leu Thr Asp Ala Gln Arg Phe Gln Asn Lys Gly Phe Thr Asn
            100                 105                 110

Pro Ile Gln Phe Pro Phe Ser Phe Ser Trp Pro Gly Thr Phe Ser Leu
        115                 120                 125

Ile Val Glu Ala Trp His Asp Thr Asn Asn Ser Gly Asn Ala Arg Thr
        130                 135                 140

Asn Lys Leu Leu Ile Gln Arg Leu Leu Val Gln Gln Val Leu Glu Val
145                 150                 155                 160

Ser Ser Glu Trp Lys Thr Asn Lys Ser Glu Ser Gln Tyr Thr Ser Leu
                165                 170                 175

Glu Tyr Asp Phe Arg Val Thr Cys Asp Leu Asn Tyr Tyr Gly Ser Gly
            180                 185                 190

Cys Ala Lys Phe Cys Arg Pro Arg Asp Asp Ser Phe Gly His Ser Thr
        195                 200                 205
```

-continued

```
Cys Ser Glu Thr Gly Glu Ile Ile Cys Leu Thr Gly Trp Gln Gly Asp
    210                 215                 220

Tyr Cys His Ile Pro Lys Cys Ala Lys Gly Cys Glu His Gly His Cys
225                 230                 235                 240

Asp Lys Pro Asn Gln Cys Val Cys Gln Leu Gly Trp Lys Gly Ala Leu
                245                 250                 255

Cys Asn Glu Cys Val Leu Glu Pro Asn Cys Ile His Gly Thr Cys Asn
            260                 265                 270

Lys Pro Trp Thr Cys Ile Cys Asn Glu Gly Trp Gly Gly Leu Tyr Cys
        275                 280                 285

Asn Gln Asp Leu Asn Tyr Cys Thr Asn His Arg Pro Cys Lys Asn Gly
    290                 295                 300

Gly Thr Cys Phe Asn Thr Gly Glu Gly Leu Tyr Thr Cys Lys Cys Ala
305                 310                 315                 320

Pro Gly Tyr Ser Gly Asp Asp Cys Glu Asn Glu Ile Tyr Ser Cys Asp
                325                 330                 335

Ala Asp Val Asn Pro Cys Gln Asn Gly Gly Thr Cys Ile Asp Glu Pro
            340                 345                 350

His Thr Lys Thr Gly Tyr Lys Cys His Cys Arg Asn Gly Trp Ser Gly
        355                 360                 365

Lys Met Cys Glu Glu Lys Val Leu Thr Cys Ser Asp Lys Pro Cys His
    370                 375                 380

Gln Gly Ile Cys Arg Asn Val Arg Pro Gly Leu Gly Ser Lys Gly Gln
385                 390                 395                 400

Gly Tyr Gln Cys Glu Cys Pro Ile Gly Tyr Ser Gly Pro Asn Cys Asp
                405                 410                 415

Leu Gln Leu Asp Asn Cys Ser Pro Asn Pro Cys Ile Asn Gly Gly Ser
            420                 425                 430

Cys Gln Pro Ser Gly Lys Cys Ile Cys Pro Ser Gly Phe Ser Gly Thr
        435                 440                 445

Arg Cys Glu Thr Asn Ile Asp Asp Cys Leu Gly His Gln Cys Glu Asn
    450                 455                 460

Gly Gly Thr Cys Ile Asp Met Val Asn Gln Tyr Arg Cys Gln Cys Val
465                 470                 475                 480

Pro Gly Phe His Gly Thr His Cys Ser Ser Lys Val Asp Leu Cys Leu
                485                 490                 495

Ile Arg Pro Cys Ala Asn Gly Gly Thr Cys Leu Asn Leu Asn Asn Asp
            500                 505                 510

Tyr Gln Cys Thr Cys Arg Ala Gly Phe Thr Gly Lys Asp Cys Ser Val
        515                 520                 525

Asp Ile Asp Glu Cys Ser Ser Gly Pro Cys His Asn Gly Gly Thr Cys
    530                 535                 540

Met Asn Arg Val Asn Ser Phe Glu Cys Val Cys Ala Asn Gly Phe Arg
545                 550                 555                 560

Gly Lys Gln Cys Asp Glu Glu Ser Tyr Asp Ser Val Thr Phe Asp Ala
                565                 570                 575

His Gln Tyr Gly Ala Thr Thr Gln Ala Arg Ala Asp Gly Leu Ala Asn
            580                 585                 590

Ala Gln Val Val Leu Ile Ala Val Phe Ser Val Ala Met Pro Leu Val
        595                 600                 605

Ala Val Ile Ala Ala Cys Val Val Phe Cys Met Lys Arg Lys Arg Lys
    610                 615                 620

Arg Ala Gln Glu Lys Asp Asn Ala Glu Ala Arg Lys Gln Asn Glu Gln
```

```
                625                 630                 635                 640
Asn Ala Val Ala Thr Met His His Asn Gly Ser Ala Gly Val Ala
                645                 650                 655
Leu Ala Ser Ala Ser Met Gly Gly Lys Thr Gly Ser Asn Ser Gly Leu
                660                 665                 670
Thr Phe Asp Gly Gly Asn Pro Asn Ile Ile Lys Asn Thr Trp Asp Lys
                675                 680                 685
Ser Val Asn Asn Ile Cys Ala Ser Ala Ala Ala Ala Ala Ala
                690                 695                 700
Ala Ala Ala Asp Glu Cys Leu Met Tyr Gly Gly Tyr Val Ala Ser Val
705                 710                 715                 720
Ala Asp Asn Asn Ala Asn Ser Asp Phe Cys Val Ala Pro Leu Gln
                725                 730                 735
Arg Ala Lys Ser Gln Lys Gln Leu Asn Thr Asp Pro Thr Leu Met His
                740                 745                 750
Arg Gly Ser Pro Ala Gly Thr Ser Ala Lys Gly Ala Ser Gly Gly Gly
                755                 760                 765
Pro Gly Ala Ala Glu Gly Lys Arg Ile Ser Val Leu Gly Glu Gly Ser
770                 775                 780
Tyr Cys Ser Gln Arg Trp Pro Ser Leu Ala Ala Gly Val Ala Gly
785                 790                 795                 800
Asp Leu Phe Ile Gln Leu Met Ala Ala Ser Val Ala Gly Thr Asp
                805                 810                 815
Gly Thr Ala Gln Gln Gln Arg Ser Val Val Cys Gly Thr Pro His Met
                820                 825                 830

<210> SEQ ID NO 7
<211> LENGTH: 46
<212> TYPE: PRT
<213> ORGANISM: Drosophila

<400> SEQUENCE: 7

Val Gln Cys Ala Val Thr Tyr Tyr Asn Thr Thr Phe Cys Thr Thr Phe
1               5                   10                  15
Cys Arg Pro Arg Asp Asp Gln Phe Gly His Tyr Ala Cys Gly Ser Glu
                20                  25                  30
Gly Gln Lys Leu Cys Leu Asn Gly Trp Gln Gly Val Asn Cys
                35                  40                  45

<210> SEQ ID NO 8
<211> LENGTH: 45
<212> TYPE: PRT
<213> ORGANISM: Gallus gallus

<400> SEQUENCE: 8

Val Thr Cys Ala Glu His Tyr Tyr Gly Phe Gly Cys Asn Lys Phe Cys
1               5                   10                  15
Arg Pro Arg Asp Asp Phe Phe Thr His His Thr Cys Asp Gln Asn Gly
                20                  25                  30
Asn Lys Thr Cys Leu Glu Gly Trp Thr Gly Pro Glu Cys
                35                  40                  45

<210> SEQ ID NO 9
<211> LENGTH: 43
<212> TYPE: PRT
<213> ORGANISM: Drosophila

<400> SEQUENCE: 9
```

```
Asn Leu Cys Ser Ser Asn Tyr His Gly Lys Arg Cys Asn Arg Tyr Cys
  1               5                  10                  15

Ile Ala Asn Ala Lys Leu His Trp Glu Cys Ser Thr His Gly Val Arg
             20                  25                  30

Arg Cys Ser Ala Gly Trp Ser Gly Glu Asp Cys
         35                  40

<210> SEQ ID NO 10
<211> LENGTH: 45
<212> TYPE: PRT
<213> ORGANISM: Drosophila

<400> SEQUENCE: 10

Val Thr Cys Ala Arg Asn Tyr Phe Gly Asn Arg Cys Glu Asn Phe Cys
  1               5                  10                  15

Asp Ala His Leu Ala Lys Ala Ala Arg Lys Arg Cys Asp Ala Met Gly
             20                  25                  30

Arg Leu Arg Cys Asp Ile Gly Trp Met Gly Pro His Cys
         35                  40                  45

<210> SEQ ID NO 11
<211> LENGTH: 2692
<212> TYPE: DNA
<213> ORGANISM: mouse
<220> FEATURE:
<221> NAME/KEY: CDS
<222> LOCATION: (31)...(2199)
<223> OTHER INFORMATION: Mouse Delta (M-Delta-1) gene

<400> SEQUENCE: 11
ctgcaggaat tcsmycgcat gctcccggcc gcc atg ggc cgt cgg agc gcg cta      54
                                   Ala Met Gly Arg Arg Ser Ala Leu
                                                 1               5 gcc ctt gcc gtg gtc tct gcc ctg ctg tgc cag gtc tgg agc tcc ggc     102
Ala Leu Ala Val Val Ser Ala Leu Leu Cys Gln Val Trp Ser Ser Gly
         10                  15                  20 gta ttt gag ctg aag ctg cag gag ttc gtc aac aag aag ggg ctg ctg     150
Val Phe Glu Leu Lys Leu Gln Glu Phe Val Asn Lys Lys Gly Leu Leu
 25                  30                  35                  40 ggg aac cgc aac tgc tgc cgc ggg ggc tct ggc ccg cct tgc gcc tgc     198
Gly Asn Arg Asn Cys Cys Arg Gly Gly Ser Gly Pro Pro Cys Ala Cys
                 45                  50                  55 agg acc ttc ttt cgc gta tgc ctc aag cac tac cag gcc agc gtg tca     246
Arg Thr Phe Phe Arg Val Cys Leu Lys His Tyr Gln Ala Ser Val Ser
             60                  65                  70 ccg gag cca ccc tgc acc tac ggc agt gcc gtc acg cca gtg ctg ggt     294
Pro Glu Pro Pro Cys Thr Tyr Gly Ser Ala Val Thr Pro Val Leu Gly
         75                  80                  85 gtc gac tcc ttc agc ctg cct gat ggc gca ggc atc gac ccc gcc ttc     342
Val Asp Ser Phe Ser Leu Pro Asp Gly Ala Gly Ile Asp Pro Ala Phe
     90                  95                 100 agc aac ccc atc cga ttc ccc ttc ggc ttc acc tgg cca ggt acc ttc     390
Ser Asn Pro Ile Arg Phe Pro Phe Gly Phe Thr Trp Pro Gly Thr Phe
105                 110                 115                 120 tct ctg atc att gaa gcc ctc cat aca gac tct ccc gat gac ctc gca     438
Ser Leu Ile Ile Glu Ala Leu His Thr Asp Ser Pro Asp Asp Leu Ala
                125                 130                 135 aca gaa aac cca gaa aga ctc atc agc cgc ctg acc aca cag agg cac     486
Thr Glu Asn Pro Glu Arg Leu Ile Ser Arg Leu Thr Thr Gln Arg His
            140                 145                 150 ctc act gtg gga gaa gaa tgg tct cag gac ctt cac agt agc ggc cgc     534
Leu Thr Val Gly Glu Glu Trp Ser Gln Asp Leu His Ser Ser Gly Arg
```

-continued

|  | 155 |  |  |  | 160 |  |  |  | 165 |  |  |  |  |
|---|---|---|---|---|---|---|---|---|---|---|---|---|---|
| aca | gac | ctc | cgg | tac | tct | tac | cgg | ttt | gtg | tgt | gac | gag cac tac tac | 582 |
| Thr | Asp | Leu | Arg | Tyr | Ser | Tyr | Arg | Phe | Val | Cys | Asp | Glu His Tyr Tyr | |
|  | 170 | | | | 175 | | | | 180 | | | | |

```
aca gac ctc cgg tac tct tac cgg ttt gtg tgt gac gag cac tac tac    582
Thr Asp Leu Arg Tyr Ser Tyr Arg Phe Val Cys Asp Glu His Tyr Tyr
        170                 175                 180 gga gaa ggt tgc tct gtg ttc tgc cga cct cgg gat gac gcc ttt ggc    630
Gly Glu Gly Cys Ser Val Phe Cys Arg Pro Arg Asp Asp Ala Phe Gly
185                 190                 195                 200 cac ttc acc tgc ggg gac aga ggg gag aag atg tgc gac cct ggc tgg    678
His Phe Thr Cys Gly Asp Arg Gly Glu Lys Met Cys Asp Pro Gly Trp
            205                 210                 215 aaa ggc cag tac tgc act gac cca atc tgt ctg cca ggg tgt gat gac    726
Lys Gly Gln Tyr Cys Thr Asp Pro Ile Cys Leu Pro Gly Cys Asp Asp
        220                 225                 230 caa cat gga tac tgt gac aaa cca ggg gag tgc aag tgc aga gtt ggc    774
Gln His Gly Tyr Cys Asp Lys Pro Gly Glu Cys Lys Cys Arg Val Gly
            235                 240                 245 tgg cag ggc cgc tac tgc gat gag tgc atc cga tac cca ggt tgt gtc    822
Trp Gln Gly Arg Tyr Cys Asp Glu Cys Ile Arg Tyr Pro Gly Cys Val
250                 255                 260 cat ggc acc tgc cag caa ccc tgg cag tgt aac tgc cag gaa ggc tgg    870
His Gly Thr Cys Gln Gln Pro Trp Gln Cys Asn Cys Gln Glu Gly Trp
265                 270                 275                 280 ggg ggc ctt ttc tgc aac caa gac ctg aac tac tgt act cac cat aag    918
Gly Gly Leu Phe Cys Asn Gln Asp Leu Asn Tyr Cys Thr His His Lys
                285                 290                 295 ccg tgc agg aat gga gcc acc tgc acc aac acg ggc cag ggg agc tac    966
Pro Cys Arg Asn Gly Ala Thr Cys Thr Asn Thr Gly Gln Gly Ser Tyr
            300                 305                 310 aca tgt tcc tgc cga cct ggg tat aca ggt gcc aac tgt gag ctg gaa   1014
Thr Cys Ser Cys Arg Pro Gly Tyr Thr Gly Ala Asn Cys Glu Leu Glu
        315                 320                 325 gta gat gag tgt gct cct agc ccc tgc aag aac gga gcg agc tgc acg   1062
Val Asp Glu Cys Ala Pro Ser Pro Cys Lys Asn Gly Ala Ser Cys Thr
330                 335                 340 gac ctt gag gac agc ttc tct tgc acc tgc cct ccc ggc ttc tat ggc   1110
Asp Leu Glu Asp Ser Phe Ser Cys Thr Cys Pro Pro Gly Phe Tyr Gly
345                 350                 355                 360 aag gtc tgt gag ctg agc gcc atg acc tgt gca gat ggc cct tgc ttc   1158
Lys Val Cys Glu Leu Ser Ala Met Thr Cys Ala Asp Gly Pro Cys Phe
                365                 370                 375 aat gga gga cga tgt tca gat aac cct gac gga ggc tac acc tgc cat   1206
Asn Gly Gly Arg Cys Ser Asp Asn Pro Asp Gly Gly Tyr Thr Cys His
            380                 385                 390 tgc ccc ttg ggc ttc tct ggc ttc aac tgt gag aag aag atg gat ctc   1254
Cys Pro Leu Gly Phe Ser Gly Phe Asn Cys Glu Lys Lys Met Asp Leu
        395                 400                 405 tgc ggc tct tcc cct tgt tct aac ggt gcc aag tgt gtg gac ctc ggc   1302
Cys Gly Ser Ser Pro Cys Ser Asn Gly Ala Lys Cys Val Asp Leu Gly
410                 415                 420 aac tct tac ctg tgc cgg tgc cag gct ggc ttc tcc ggg agg tac tgc   1350
Asn Ser Tyr Leu Cys Arg Cys Gln Ala Gly Phe Ser Gly Arg Tyr Cys
425                 430                 435                 440 gag gac aat gtg gat gac tgt gcc tcc tcc ccg tgt gca aat ggg ggc   1398
Glu Asp Asn Val Asp Asp Cys Ala Ser Ser Pro Cys Ala Asn Gly Gly
                445                 450                 455 acc tgc cgg gac agt gtg aac gac ttc tcc tgt acc tgc cca cct ggc   1446
Thr Cys Arg Asp Ser Val Asn Asp Phe Ser Cys Thr Cys Pro Pro Gly
            460                 465                 470 tac acg ggc aag aac tgc agc gcc cct gtc agc agg tgt gag cat gca   1494
Tyr Thr Gly Lys Asn Cys Ser Ala Pro Val Ser Arg Cys Glu His Ala
```

-continued

```
              475                 480                 485
ccc tgc cat aat ggg gcc acc tgc cac cag agg ggc cag cgc tac atg      1542
Pro Cys His Asn Gly Ala Thr Cys His Gln Arg Gly Gln Arg Tyr Met
490                 495                 500 tgt gag tgc gcc cag ggc tat ggc ggc ccc aac tgc cag ttt ctg ctc      1590
Cys Glu Cys Ala Gln Gly Tyr Gly Gly Pro Asn Cys Gln Phe Leu Leu
505                 510                 515                 520 cct gag cca cca cca ggg ccc atg gtg gtg gac ctc agt gag agg cat      1638
Pro Glu Pro Pro Pro Gly Pro Met Val Val Asp Leu Ser Glu Arg His
                525                 530                 535 atg gag agc cag ggc ggg ccc ttc ccc tgg gtg gcc gtg tgt gcc ggg      1686
Met Glu Ser Gln Gly Gly Pro Phe Pro Trp Val Ala Val Cys Ala Gly
            540                 545                 550 gtg gtg ctt gtc ctc ctg ctg ctg ggc tgt gct gct gtg gtg gtc          1734
Val Val Leu Val Leu Leu Leu Leu Gly Cys Ala Ala Val Val Val
            555                 560                 565 tgc gtc cgg ctg aag cta cag aaa cac cag cct cca cct gaa ccc tgt      1782
Cys Val Arg Leu Lys Leu Gln Lys His Gln Pro Pro Pro Glu Pro Cys
570                 575                 580 ggg gga gag aca gaa acc atg aac aac cta gcc aat tgc cag cgc gag      1830
Gly Gly Glu Thr Glu Thr Met Asn Asn Leu Ala Asn Cys Gln Arg Glu
585                 590                 595                 600 aag gac gtt tct gtt agc atc att ggg gct acc cag atc aag aac acc      1878
Lys Asp Val Ser Val Ser Ile Ile Gly Ala Thr Gln Ile Lys Asn Thr
                605                 610                 615 aac aag aag gcg gac ttt cac ggg gac cat gga gcc gag aag agc agc      1926
Asn Lys Lys Ala Asp Phe His Gly Asp His Gly Ala Glu Lys Ser Ser
            620                 625                 630 ttt aag gtc cga tac ccc act gtg gac tat aac ctc gtt cga gac ctc      1974
Phe Lys Val Arg Tyr Pro Thr Val Asp Tyr Asn Leu Val Arg Asp Leu
            635                 640                 645 aag gga gat gaa gcc acg gtc agg gat aca cac agc aaa cgt gac acc      2022
Lys Gly Asp Glu Ala Thr Val Arg Asp Thr His Ser Lys Arg Asp Thr
650                 655                 660 aag tgc cag tca cag agt ctg cag gag aag aga aga tcg ccc caa cac      2070
Lys Cys Gln Ser Gln Ser Leu Gln Glu Lys Arg Arg Ser Pro Gln His
665                 670                 675                 680 tta ggg gtg ggg aga ttc ctg aca gaa aac agg cca gag tct gtc tac      2118
Leu Gly Val Gly Arg Phe Leu Thr Glu Asn Arg Pro Glu Ser Val Tyr
                685                 690                 695 tct act tca aag gac acc aag tac cag tcg gtg tat gtt ctg tct gca      2166
Ser Thr Ser Lys Asp Thr Lys Tyr Gln Ser Val Tyr Val Leu Ser Ala
            700                 705                 710 gaa aag gat gag tgt gtt ata gcg act gag gtg taagatggaa gcgatgtggc    2219
Glu Lys Asp Glu Cys Val Ile Ala Thr Glu Val
            715                 720 aaaattccca tttctcttaa ataaaattcc aaggatatag ccccgatgaa tgctgctgag    2279
agaggaaggg agaggaaacc cagggactgc tgctgagaac caggttcagg cgaacgtggt    2339
tctctcagag ttagcagagg cgcccgacac tgccagccta ggctttggct gccgctggac    2399
tgcctgctgg ttgttcccat tgcactatgg acagttgctt tgaagagtat atatttaaat    2459
ggacgagtga cttgattcat ataggaagca cgcactgccc acacgtctat cttggattac    2519
tatgagccag tctttccttg aactagaaac acaactgcct ttattgtcct ttttgatact    2579
gagatgtgtt ttttttttttt cctagacggg aaaaagaaaa cgtgtgttat ttttttttggg  2639 atttgtaaaa atattttttca tgattatggg agagctccca acgcgttgga ggt          2692

<210> SEQ ID NO 12
```

```
<211> LENGTH: 722
<212> TYPE: PRT
<213> ORGANISM: mouse

<400> SEQUENCE: 12
```

| | | | | | | | | | | | | | | | |
|---|---|---|---|---|---|---|---|---|---|---|---|---|---|---|---|
|Met|Gly|Arg|Arg|Ser|Ala|Leu|Ala|Leu|Ala|Val|Val|Ser|Ala|Leu|Leu|
|1| | | |5| | | | |10| | | | |15| |
|Cys|Gln|Val|Trp|Ser|Ser|Gly|Val|Phe|Glu|Leu|Lys|Leu|Gln|Glu|Phe|
| | | |20| | | | |25| | | | |30| | |
|Val|Asn|Lys|Lys|Gly|Leu|Leu|Gly|Asn|Arg|Asn|Cys|Cys|Arg|Gly|Gly|
| | | |35| | | | |40| | | | |45| | |
|Ser|Gly|Pro|Pro|Cys|Ala|Cys|Arg|Thr|Phe|Phe|Arg|Val|Cys|Leu|Lys|
| |50| | | | |55| | | | |60| | | | |
|His|Tyr|Gln|Ala|Ser|Val|Ser|Pro|Glu|Pro|Cys|Thr|Tyr|Gly|Ser|
|65| | | | |70| | | | |75| | | | |80|
|Ala|Val|Thr|Pro|Val|Leu|Gly|Val|Asp|Ser|Phe|Ser|Leu|Pro|Asp|Gly|
| | | | |85| | | | |90| | | | |95| |
|Ala|Gly|Ile|Asp|Pro|Ala|Phe|Ser|Asn|Pro|Ile|Arg|Phe|Pro|Phe|Gly|
| | | |100| | | | |105| | | | |110| | |
|Phe|Thr|Trp|Pro|Gly|Thr|Phe|Ser|Leu|Ile|Ile|Glu|Ala|Leu|His|Thr|
| | | |115| | | | |120| | | | |125| | |
|Asp|Ser|Pro|Asp|Asp|Leu|Ala|Thr|Glu|Asn|Pro|Glu|Arg|Leu|Ile|Ser|
| |130| | | | |135| | | | |140| | | | |
|Arg|Leu|Thr|Thr|Gln|Arg|His|Leu|Thr|Val|Gly|Glu|Glu|Trp|Ser|Gln|
|145| | | | |150| | | | |155| | | | |160|
|Asp|Leu|His|Ser|Ser|Gly|Arg|Thr|Asp|Leu|Arg|Tyr|Ser|Tyr|Arg|Phe|
| | | | |165| | | | |170| | | | |175| |
|Val|Cys|Asp|Glu|His|Tyr|Tyr|Gly|Glu|Gly|Cys|Ser|Val|Phe|Cys|Arg|
| | | |180| | | | |185| | | | |190| | |
|Pro|Arg|Asp|Asp|Ala|Phe|Gly|His|Phe|Thr|Cys|Gly|Asp|Arg|Gly|Glu|
| | | |195| | | | |200| | | | |205| | |
|Lys|Met|Cys|Asp|Pro|Gly|Trp|Lys|Gly|Gln|Tyr|Cys|Thr|Asp|Pro|Ile|
| |210| | | | |215| | | | |220| | | | |
|Cys|Leu|Pro|Gly|Cys|Asp|Asp|Gln|His|Gly|Tyr|Cys|Asp|Lys|Pro|Gly|
|225| | | | |230| | | | |235| | | | |240|
|Glu|Cys|Lys|Cys|Arg|Val|Gly|Trp|Gln|Gly|Arg|Tyr|Cys|Asp|Glu|Cys|
| | | | |245| | | | |250| | | | |255| |
|Ile|Arg|Tyr|Pro|Gly|Cys|Val|His|Gly|Thr|Cys|Gln|Gln|Pro|Trp|Gln|
| | | |260| | | | |265| | | | |270| | |
|Cys|Asn|Cys|Gln|Glu|Gly|Trp|Gly|Gly|Leu|Phe|Cys|Asn|Gln|Asp|Leu|
| | | |275| | | | |280| | | | |285| | |
|Asn|Tyr|Cys|Thr|His|His|Lys|Pro|Cys|Arg|Asn|Gly|Ala|Thr|Cys|Thr|
| |290| | | | |295| | | | |300| | | | |
|Asn|Thr|Gly|Gln|Gly|Ser|Tyr|Thr|Cys|Ser|Cys|Arg|Pro|Gly|Tyr|Thr|
|305| | | | |310| | | | |315| | | | |320|
|Gly|Ala|Asn|Cys|Glu|Leu|Glu|Val|Asp|Glu|Cys|Ala|Pro|Ser|Pro|Cys|
| | | | |325| | | | |330| | | | |335| |
|Lys|Asn|Gly|Ala|Ser|Cys|Thr|Asp|Leu|Glu|Asp|Ser|Phe|Ser|Cys|Thr|
| | | |340| | | | |345| | | | |350| | |
|Cys|Pro|Pro|Gly|Phe|Tyr|Gly|Lys|Val|Cys|Glu|Leu|Ser|Ala|Met|Thr|
| | | |355| | | | |360| | | | |365| | |
|Cys|Ala|Asp|Gly|Pro|Cys|Phe|Asn|Gly|Gly|Arg|Cys|Ser|Asp|Asn|Pro|
| |370| | | | |375| | | | |380| | | | |
|Asp|Gly|Gly|Tyr|Thr|Cys|His|Cys|Pro|Leu|Gly|Phe|Ser|Gly|Phe|Asn|
|385| | | | |390| | | | |395| | | | |400|

Cys Glu Lys Lys Met Asp Leu Cys Gly Ser Pro Cys Ser Asn Gly
                405                 410                 415

Ala Lys Cys Val Asp Leu Gly Asn Ser Tyr Leu Cys Arg Cys Gln Ala
            420                 425                 430

Gly Phe Ser Gly Arg Tyr Cys Glu Asp Asn Val Asp Asp Cys Ala Ser
        435                 440                 445

Ser Pro Cys Ala Asn Gly Gly Thr Cys Arg Asp Ser Val Asn Asp Phe
450                 455                 460

Ser Cys Thr Cys Pro Pro Gly Tyr Thr Gly Lys Asn Cys Ser Ala Pro
465                 470                 475                 480

Val Ser Arg Cys Glu His Ala Pro Cys His Asn Gly Ala Thr Cys His
                485                 490                 495

Gln Arg Gly Gln Arg Tyr Met Cys Glu Cys Ala Gln Gly Tyr Gly Gly
            500                 505                 510

Pro Asn Cys Gln Phe Leu Leu Pro Glu Pro Pro Pro Gly Pro Met Val
        515                 520                 525

Val Asp Leu Ser Glu Arg His Met Glu Ser Gln Gly Gly Pro Phe Pro
530                 535                 540

Trp Val Ala Val Cys Ala Gly Val Val Leu Val Leu Leu Leu Leu Leu
545                 550                 555                 560

Gly Cys Ala Ala Val Val Val Cys Val Arg Leu Lys Leu Gln Lys His
                565                 570                 575

Gln Pro Pro Pro Glu Pro Cys Gly Gly Glu Thr Glu Thr Met Asn Asn
            580                 585                 590

Leu Ala Asn Cys Gln Arg Glu Lys Asp Val Ser Val Ser Ile Ile Gly
        595                 600                 605

Ala Thr Gln Ile Lys Asn Thr Asn Lys Lys Ala Asp Phe His Gly Asp
610                 615                 620

His Gly Ala Glu Lys Ser Ser Phe Lys Val Arg Tyr Pro Thr Val Asp
625                 630                 635                 640

Tyr Asn Leu Val Arg Asp Leu Lys Gly Asp Glu Ala Thr Val Arg Asp
                645                 650                 655

Thr His Ser Lys Arg Asp Thr Lys Cys Gln Ser Gln Ser Leu Gln Glu
            660                 665                 670

Lys Arg Arg Ser Pro Gln His Leu Gly Val Gly Arg Phe Leu Thr Glu
        675                 680                 685

Asn Arg Pro Glu Ser Val Tyr Ser Thr Ser Lys Asp Thr Lys Tyr Gln
690                 695                 700

Ser Val Tyr Val Leu Ser Ala Glu Lys Asp Glu Cys Val Ile Ala Thr
705                 710                 715                 720

Glu Val

<210> SEQ ID NO 13
<211> LENGTH: 578
<212> TYPE: PRT
<213> ORGANISM: Artificial Sequence
<220> FEATURE:
<223> OTHER INFORMATION: Consenses sequence of Chick Delta and Mouse
      Delta

<400> SEQUENCE: 13

Met Gly Arg Leu Leu Ala Ser Ala Leu Leu Cys Val Ser Gly Val Phe
1               5                   10                  15

Glu Leu Lys Leu Gln Glu Phe Val Asn Lys Lys Gly Leu Leu Asn Arg
            20                  25                  30

```
Asn Cys Cys Arg Gly Gly Cys Cys Thr Phe Phe Arg Val Cys Leu
            35                  40                  45
Lys His Tyr Gln Ala Ser Val Ser Pro Glu Pro Pro Cys Thr Tyr Gly
 50                  55                  60
Ser Ala Thr Pro Val Leu Gly Ser Phe Ser Pro Asp Gly Ala Gly Asp
 65                  70                  75                  80
Pro Ala Phe Ser Asn Pro Ile Arg Phe Pro Phe Gly Phe Thr Trp Pro
                 85                  90                  95
Gly Thr Phe Ser Leu Ile Ile Glu Ala Leu His Thr Asp Ser Pro Asp
                100                 105                 110
Asp Leu Thr Glu Asn Pro Glu Arg Leu Ile Ser Arg Leu Thr Gln Arg
            115                 120                 125
His Leu Val Gly Glu Glu Trp Ser Gln Asp Leu His Ser Ser Gly Arg
130                 135                 140
Thr Asp Leu Tyr Ser Tyr Arg Phe Val Cys Asp Glu His Tyr Tyr Gly
145                 150                 155                 160
Glu Gly Cys Ser Val Phe Cys Arg Pro Arg Asp Asp Phe Gly His Phe
                165                 170                 175
Thr Cys Gly Arg Gly Glu Lys Cys Pro Gly Trp Lys Gly Gln Tyr Cys
            180                 185                 190
Thr Pro Ile Cys Leu Pro Gly Cys Asp Gln His Gly Cys Asp Lys Pro
            195                 200                 205
Gly Glu Cys Lys Cys Arg Val Gly Trp Gln Gly Arg Tyr Cys Asp Glu
210                 215                 220
Cys Ile Arg Tyr Pro Gly Cys Val His Gly Thr Cys Gln Gln Pro Trp
225                 230                 235                 240
Gln Cys Asn Cys Gln Glu Gly Trp Gly Gly Leu Phe Cys Asn Gln Asp
                245                 250                 255
Leu Asn Tyr Cys Thr His His Lys Pro Cys Asn Gly Ala Thr Cys Thr
            260                 265                 270
Asn Thr Gly Gln Gly Ser Tyr Thr Cys Ser Cys Arg Pro Gly Tyr Thr
            275                 280                 285
Gly Cys Glu Glu Glu Cys Pro Cys Lys Asn Gly Ser Cys Thr Asp Leu
290                 295                 300
Glu Ser Ser Cys Thr Cys Pro Pro Gly Phe Tyr Gly Lys Cys Glu Leu
305                 310                 315                 320
Ser Ala Met Thr Cys Ala Asp Gly Pro Cys Phe Asn Gly Gly Arg Cys
                325                 330                 335
Asp Asn Pro Asp Gly Gly Tyr Cys Cys Pro Leu Gly Ser Gly Phe Asn
            340                 345                 350
Cys Glu Lys Lys Asp Cys Ser Ser Pro Cys Asn Gly Ala Cys Val Asp
            355                 360                 365
Leu Gly Asn Ser Tyr Cys Cys Gln Ala Gly Phe Gly Arg Cys Asp Asn
370                 375                 380
Val Asp Asp Cys Ala Ser Pro Cys Asn Gly Gly Thr Cys Asp Val Asn
385                 390                 395                 400
Asp Ser Cys Thr Cys Pro Pro Gly Tyr Gly Lys Asn Cys Ser Pro Val
                405                 410                 415
Ser Arg Cys Glu His Pro Cys His Asn Gly Ala Thr Cys His Arg Arg
            420                 425                 430
Tyr Cys Glu Cys Ala Gly Tyr Gly Gly Asn Cys Gln Phe Leu Leu Pro
            435                 440                 445
Glu Pro Pro Gly Pro Val Asp Glu Glu Gln Phe Pro Trp Ala Val Cys
450                 455                 460
```

```
Ala Gly Leu Val Leu Leu Leu Gly Cys Ala Ala Val Cys Val
465                 470                 475                 480

Arg Leu Lys Gln Lys Pro Glu Cys Glu Thr Glu Thr Met Asn Asn Leu
                485                 490                 495

Ala Asn Cys Gln Arg Glu Lys Asp Ser Ser Ile Gly Ala Thr Gln Ile
            500                 505                 510

Lys Asn Thr Asn Lys Lys Asp Phe His Asp Lys Lys Val Arg Tyr Pro
        515                 520                 525

Val Asp Tyr Asn Leu Val Leu Lys Val His Lys Lys Cys Ser Glu Glu
    530                 535                 540

Lys Ala Leu Arg Lys Arg Pro Ser Val Tyr Ser Thr Ser Lys Asp Thr
545                 550                 555                 560

Lys Tyr Gln Ser Val Tyr Val Ser Glu Lys Asp Glu Cys Ile Ala Thr
                565                 570                 575

Glu Val
```

```
<210> SEQ ID NO 14
<211> LENGTH: 525
<212> TYPE: DNA
<213> ORGANISM: Homo sapiens

<400> SEQUENCE: 14
tacgatgaay aacctggcga actgccagcg tgagaaggac atctcagtca gcatcatcgg     60
ggcyacgtca gatcargaac accaacaaga aggcggactt ymcascgggg gaccasagcg    120
tccgacaaga atggmtttca aggcccgcta ccccagcgtg actataact cgtgcaggac     180 ctcaagggtg acgacaccgc cgtcaggacg tcgcacagca agcgtgacac caagtgccag    240
tccccaggct cctcaggag gagaagggga ccccgaccac actcaggggk tgcgtgctgc     300
gggccgggct caggaggggg tacctggggg gtgtcttcct ggaaccactg ctccgtttct    360
cttcccaaat gttctcatgc attcattgtg gattttctct attttcctt tagtggagaa    420 gcatctgaaa gaaaaaggcc ggactcgggc tgttcaactt caaaagacac caagtaccag    480
tcggtgtacg tcatatccga ggagaaggac gagtgcgtca tcgca                   525
```

```
<210> SEQ ID NO 15
<211> LENGTH: 10
<212> TYPE: PRT
<213> ORGANISM: Artificial Sequence
<220> FEATURE:
<223> OTHER INFORMATION: Predicted amino acid sequence of humna delta
<220> FEATURE:
<221> NAME/KEY: VARIANT
<222> LOCATION: 4
<223> OTHER INFORMATION: Xaa = Any Amino Acid

<400> SEQUENCE: 15

Tyr Asp Glu Xaa Pro Gly Glu Leu Pro Ala
1               5                   10
```

```
<210> SEQ ID NO 16
<211> LENGTH: 44
<212> TYPE: PRT
<213> ORGANISM: Artificial Sequence
<220> FEATURE:
<223> OTHER INFORMATION: Predicted amino acid sequence of humna delta
<220> FEATURE:
<221> NAME/KEY: VARIANT
<222> LOCATION: 11, 15, 23, 24, 28
<223> OTHER INFORMATION: Xaa = Any Amino Acid

<400> SEQUENCE: 16
```

-continued

```
Glu Gly His Leu Ser Gln His His Arg Gly Xaa Val Arg Ser Xaa Thr
 1               5                  10                  15

Pro Thr Arg Arg Arg Thr Xaa Xaa Arg Gly Thr Xaa Ala Ser Asp Lys
             20                  25                  30

Asn Gly Phe Gln Gly Pro Leu Pro Gln Arg Gly Leu
         35                  40
```

<210> SEQ ID NO 17
<211> LENGTH: 118
<212> TYPE: PRT
<213> ORGANISM: Artificial Sequence
<220> FEATURE:
<223> OTHER INFORMATION: Predicted amino acid sequence of humna delta
<220> FEATURE:
<221> NAME/KEY: VARIANT
<222> LOCATION: 41
<223> OTHER INFORMATION: Xaa = Any Amino Acid

<400> SEQUENCE: 17

```
Leu Val Gln Asp Leu Lys Gly Asp Asp Thr Ala Val Arg Thr Ser His
 1               5                  10                  15

Ser Lys Arg Asp Thr Lys Cys Gln Ser Pro Gly Ser Ser Gly Arg Arg
             20                  25                  30

Arg Gly Pro Arg Pro His Ser Gly Xaa Ala Cys Cys Gly Pro Gly Ser
         35                  40                  45

Gly Gly Gly Thr Trp Gly Val Ser Ser Trp His Cys Ser Val Ser Leu
     50                  55                  60

Pro Lys Cys Ser His Ala Phe Ile Val Asp Phe Leu Tyr Phe Pro Phe
65                  70                  75                  80

Ser Gly Glu Ala Ser Glu Arg Lys Arg Pro Asp Ser Gly Cys Ser Thr
                 85                  90                  95

Ser Lys Asp Thr Lys Tyr Gln Ser Val Tyr Val Ile Ser Glu Glu Lys
            100                 105                 110

Asp Glu Cys Val Ile Ala
        115
```

<210> SEQ ID NO 18
<211> LENGTH: 173
<212> TYPE: PRT
<213> ORGANISM: Artificial Sequence
<220> FEATURE:
<223> OTHER INFORMATION: Predicted amino acid sequence of human delta
<220> FEATURE:
<221> NAME/KEY: VARIANT
<222> LOCATION: 34, 35, 39, 44, 96
<223> OTHER INFORMATION: Xaa = Any Amino Acid

<400> SEQUENCE: 18

```
Thr Met Asn Asn Leu Ala Asn Cys Gln Arg Glu Lys Asp Ile Ser Val
 1               5                  10                  15

Ser Ile Ile Gly Ala Thr Ser Asp Gln Glu His Gln Gln Glu Gly Gly
             20                  25                  30

Leu Xaa Xaa Gly Gly Pro Xaa Pro Thr Arg Met Xaa Phe Lys Ala Arg
         35                  40                  45

Tyr Pro Ser Val Asp Tyr Asn Ser Cys Arg Thr Ser Arg Val Thr Thr
     50                  55                  60

Pro Pro Ser Gly Arg Arg Thr Ala Ser Val Thr Pro Ser Ala Ser Pro
65                  70                  75                  80

Gln Ala Pro Gln Gly Gly Glu Gly Asp Pro Asp His Thr Gln Gly Xaa
                 85                  90                  95
```

Arg Ala Ala Gly Arg Ala Gln Glu Gly Val Pro Gly Gly Cys Leu Pro
            100                 105                 110

Gly Thr Thr Ala Pro Phe Leu Phe Pro Asn Val Leu Met His Ser Leu
        115                 120                 125

Trp Ile Phe Ser Ile Phe Leu Leu Val Glu Lys His Leu Lys Glu Lys
130                 135                 140

Gly Arg Thr Arg Ala Val Gln Leu Gln Lys Thr Pro Ser Thr Ser Arg
145                 150                 155                 160

Cys Thr Ser Tyr Pro Arg Arg Thr Ser Ala Ser Ser
                165                 170

<210> SEQ ID NO 19
<211> LENGTH: 60
<212> TYPE: PRT
<213> ORGANISM: Artificial Sequence
<220> FEATURE:
<223> OTHER INFORMATION: Predicted amino acid sequence of human delta
<220> FEATURE:
<221> NAME/KEY: VARIANT
<222> LOCATION: 1, 19, 23, 32, 33, 36, 43
<223> OTHER INFORMATION: Xaa = Any Amino Acid

<400> SEQUENCE: 19

Xaa Thr Trp Arg Thr Ala Ser Val Arg Arg Thr Ser Gln Ser Ala Ser
1               5                   10                  15

Ser Gly Xaa Arg Gln Ile Xaa Asn Thr Asn Lys Lys Ala Asp Phe Xaa
            20                  25                  30

Xaa Gly Asp Xaa Ser Val Arg Gln Glu Trp Xaa Ser Arg Pro Ala Thr
        35                  40                  45

Pro Ala Trp Thr Ile Thr Arg Ala Gly Pro Gln Gly
    50                  55                  60

<210> SEQ ID NO 20
<211> LENGTH: 11
<212> TYPE: PRT
<213> ORGANISM: Artificial Sequence
<220> FEATURE:
<223> OTHER INFORMATION: Predicted amino acid sequence of human delta

<400> SEQUENCE: 20

Arg His Arg Arg Gln Asp Val Ala Gln Gln Ala
1               5                   10

<210> SEQ ID NO 21
<211> LENGTH: 61
<212> TYPE: PRT
<213> ORGANISM: Artificial Sequence
<220> FEATURE:
<223> OTHER INFORMATION: Predicted amino acid sequence of human delta

<400> SEQUENCE: 21

His Gln Val Pro Val Pro Arg Leu Leu Arg Glu Glu Lys Gly Thr Pro
1               5                   10                  15

Thr Thr Leu Arg Gly Cys Val Leu Arg Ala Gly Leu Arg Arg Gly Tyr
            20                  25                  30

Leu Gly Gly Val Phe Leu Glu Pro Leu Leu Arg Phe Ser Ser Gln Met
        35                  40                  45

Phe Ser Cys Ile His Cys Gly Phe Ser Leu Ser Phe
    50                  55                  60

<210> SEQ ID NO 22
<211> LENGTH: 33
<212> TYPE: PRT

```
<213> ORGANISM: Artificial Sequence
<220> FEATURE:
<223> OTHER INFORMATION: Predicted amino acid sequence of human delta

<400> SEQUENCE: 22

Lys Lys Lys Ala Gly Leu Gly Leu Phe Asn Phe Lys Lys Arg His Gln
  1               5                  10                  15

Val Pro Val Gly Val Arg His Ile Arg Gly Glu Gly Arg Val Arg His
             20                  25                  30

Arg

<210> SEQ ID NO 23
<211> LENGTH: 175
<212> TYPE: PRT
<213> ORGANISM: Artificial Sequence
<220> FEATURE:
<223> OTHER INFORMATION: Predicted amino acid sequence of human delta
<220> FEATURE:
<221> NAME/KEY: VARIANT
<222> LOCATION: 25, 34, 35, 38, 97
<223> OTHER INFORMATION: Xaa = Any Amino Acid

<400> SEQUENCE: 23

Thr Met Asn Asn Leu Ala Asn Cys Gln Arg Glu Lys Asp Ile Ser Val
  1               5                  10                  15

Ser Ile Ile Gly Ala Thr Gly Ile Xaa Asn Thr Asn Lys Lys Ala Asp
             20                  25                  30

Phe Xaa Xaa Gly Asp Xaa Ser Ser Asp Lys Asn Gly Phe Gln Lys Ala
         35                  40                  45

Arg Tyr Pro Ser Val Asp Tyr Asn Leu Val Gln Asp Leu Lys Gly Asp
 50                  55                  60

Asp Thr Ala Val Arg Thr Ser His Ser Lys Arg Asp Thr Lys Cys Gln
 65                  70                  75                  80

Ser Pro Gly Ser Ser Gly Arg Arg Gly Pro Arg Pro His Ser Gly
                 85                  90                  95

Xaa Ala Cys Cys Gly Pro Gly Ser Gly Gly Thr Trp Gly Val Ser
            100                 105                 110

Ser Trp Asn His Cys Ser Val Ser Leu Pro Lys Cys Ser His Ala Phe
            115                 120                 125

Ile Val Asp Phe Leu Tyr Phe Pro Phe Ser Gly Glu Ala Ser Glu Arg
        130                 135                 140

Lys Arg Pro Asp Ser Gly Cys Ser Thr Ser Lys Asp Thr Lys Tyr Gln
145                 150                 155                 160

Ser Val Tyr Val Ile Ser Glu Glu Lys Asp Glu Cys Val Ile Ala
                165                 170                 175

<210> SEQ ID NO 24
<211> LENGTH: 2899
<212> TYPE: DNA
<213> ORGANISM: Artificial Sequence
<220> FEATURE:
<223> OTHER INFORMATION: Consenses sequence of mouse delta and human
      delta
<220> FEATURE:
<221> NAME/KEY: misc_feature
<222> LOCATION: 854, 973, 984, 1582, 1787, 1819, 1864, 1916, 1951, 2033,
      2152, 2156, 2171, 2183, 2194, 2212, 2220, 2226, 2230, 2244,
      2245, 2264, 2265, 2266, 2287
<223> OTHER INFORMATION: n = A,T,C or G

<400> SEQUENCE: 24
gtccagcggt accatgggcc gtcggagcgc gctaccccttt gccgtggtct ctgccctgct    60
```

```
gtgccaggtc tggagctccg gcgtatttga gctgaagctg caggagttcg tcaacaagaa    120
ggggctgctg gggaaccgca actgctgccg cggggctct ggcccgcctt gcgcctgcag     180
gaccttcttt cgcgtatgcc tcaaccacta ccaggccagc gtgtcaccgg agccaccctg    240
cacctacgga agtgctgtca cgccagtgct gggtctcgac tccttcagcc tgcctsatkg    300
sgyasgsryc smccycgagg yckwcrgyaw csmyaagyyy gatatcgmmy tycggcttca    360
cctggccrgg yaccttctct ctgatyattg aagcyctcca yacagaytct ccygatgacc    420
tcgcaacaga aacccagaa agactcatca gccgcctgrc cacycagagg cacctsackg     480
tgggmgarga rtggtcycag gacctkcaca gyagcggccg cacrgacctc mrgtactcyt    540
accgsttygt gtgtgacgar cactactacg gagarggytg ctctgtkttc tgccgwccyc    600
gggaygaygc cttyggccac ttcacctgyg gggasmgwgg ggagaarrtg tgcraccctg    660
gctggaaagg scmgtactgc acwgasccra tctgyctgcc wggrtgtgat gascarcatg    720
gatwytgtga caaaccaggg gartgcaagt gcagagtkgg ctggcagggc cgstactgyg    780
atgagtgyat ccgytaycca ggytgtctcc atggcacctg ccagcarccc tggcagtgya    840
actgccagga aggntgggggg ggcctttcct gcaaccarga cctgaactac tgyacwcacc    900
ataagccstg cargaatgga gccacctgca acmaacacgg gccaggggga gctacacwtg    960
ktcyttggcc ggncykgggt ayanagggtg ccamctgyga agcttgggra ktrgaygagt    1020
tgttgmyccy agcccytggy aagaacggag sgagctksac ggaycttcgg agracagctw    1080
ctcytgyacc tgcccwcccg gcttctaygg caarrtctgt garytgagyg ccatgacctg    1140
tgcrgaygge ccttgcttya ayggrggwcg rtgytcagay arcccygayg gaggstacas    1200
ctgccrytgc ccktgggct wctcyggctt caactgtgag aagaaratkg ayywctgcrg     1260
ctcttcmccy tgttctaayg gtgccaagtg tgtggacctc ggyraykcyt acctgtgccg    1320
stgccaggcy ggcttctcsg ggaggyactg ygasgacaay gtggaygact gygcctcctc    1380
cccgtgygcm aaygggggca cctgccggga yrgygtgaac gacttgtcct gyacctgccc    1440
rcctggctac acgggcarga actgcagygc cccygycagc aggtgygagc aygcaccctg    1500
ccayaatggg gccacctgcc acsagagggg ccascgctay wtgtgygagt gygcccrrrg    1560
ctayggsggy cccaactgcc anttyctgct cccygaarcy gmccmccmgg scccayggtg    1620
gtggaamctc msykararrm aymtarragr gccrgggsgg gcccwtcccc tkggtggycg    1680
tgtgygccgg ggtsrtsctt gtcctcmtgc tgctgctggg ctgtgcygct gtggtggtct    1740
gcgtccggct gargctrcag aarcaccrgc cyccascyga mccctgnsgg ggrgagacrg    1800
araccatgaa caacctrgnc aaytgccagc gygagaagga crtytcwgty agcatcatyg    1860
gggnyacsca catcaagaac accaacaaga aggcggactt ycacggggac cayrgngccr    1920
asaagaryrg cttyaaggyc cgmtacccmr nkgtggacta taacctcgtk crrgacctca    1980
agggwgayga mrccrcsgtc agggayrcrc acagcaarcg tgacaccaag tgncagycmc    2040
agrgctcykg aggrgargag aaggggayccs ccgaccmaca ctyaggggggt ggaggaagmw    2100
tcytgamaga aaaaggccrg astyygggyy trytcwactt tcaaargaca ancmangtac    2160
magtcggtgt nygtymtktc ygnagragga aggntgastg ygtyataggm rnytgaggtn    2220
gtaarntggn agcgatgtgg caannttccc atttctcksa aaknnnattc cmmggatata    2280
gcyccgntga atgctkctga gagaggaagg gagaggaaac ccagggactg ytkytcagaa    2340
ccaggttcag gcgaagctgg ttctctcaga gttagcagag gcgccgaca ctgccagcct     2400
aggctttggc tgccgctgga ctgcctgctg gttgttccca ttgcactatg gacagttgct    2460
```

```
ttgaagagta tatatttaaa tggacgagtg acttgattca tatacgaagc acgcactgcc    2520
cacacgtcta tcttggatta ctatgagcca gtctttcctt gaactagaaa cacaactgcc    2580
tttattgtcc tttttgatac tgagatgtgt tttttttttt cctagacggg aaaaagaaaa    2640
cgtgtgttat tttttggga tttgtaaaaa tattttcat gatatctgta aagcttgagt     2700
attttgtgac gttcattttt ttataattta aattttggta aatatgtaca aaggcacttc    2760
gggtctatgt gactatattt ttttgtatat aaatgtattt atggaatatt gtgcaaatgt    2820
tatttgagtt ttttactgtt ttgttaatga agaaattcat tttaaaaata ttttccaaa    2880 ataaatataa tgaactaca                                                 2899

<210> SEQ ID NO 25
<211> LENGTH: 8
<212> TYPE: PRT
<213> ORGANISM: Artificial Sequence
<220> FEATURE:
<223> OTHER INFORMATION: sequence encoded by SEQ ID NO. 93 (degenerated
      oligo)

<400> SEQUENCE: 25

Glu Lys Asp Glu Cys Val Ile Ala
 1               5

<210> SEQ ID NO 26
<211> LENGTH: 1981
<212> TYPE: DNA
<213> ORGANISM: Homo sapiens
<220> FEATURE:
<221> NAME/KEY: misc_feature
<222> LOCATION: 559, 678, 689, 1287, 1492, 1524, 1569, 1621, 1656, 1738,
      1857, 1861, 1876, 1888, 1899, 1917, 1925, 1931, 1935, 1942,
      1943, 1952, 1953, 1954, 1968
<223> OTHER INFORMATION: n = A,T,C or G

<400> SEQUENCE: 26
cattgggtac gggccccct cgaggtcgac ggtatcgata agcttgatat cgaattccgg     60
cttcacctgg ccgggcacct tctctctgat tattgaagct ctccacacag attctcctga    120
tgacctcgca acagaaaacc cagaaagact catcagccgc ctggccaccc agaggcacct    180
gacggtgggc gaggagtggt cccaggacct gcacagcagc ggccgcacgg acctcaagta    240
ctcctaccgc ttcgtgtgtg acgaacacta ctacggagag ggctgctccg ttttctgccg    300
tccccgggac gatgccttcg gccacttcac ctgtggggag cgtggggaga agtgtgcaa    360 ccctggctgg aaagggccct actgcacaga gccgatctgc ctgcctggat gtgatgagca    420
gcatggattt tgtgacaaac caggggaatg caagtgcaga gtgggctggc agggccggta    480
ctgtgacgag tgtatccgct atccaggctg tctccatggc acctgccagc agccctggca    540
gtgcaactgc caggaaggnt gggggggcct tttctgcaac caggacctga actactgcac    600
acaccataag ccctgcaaga atggagccac ctgcaacaaa cacgggccag gggagctac    660 acttggtctt tggccggnct ggggtacana gggtgccacc tgcgaagctt ggggattgga    720
cgagttgttg accccagccc ttggtaagaa cggagggagc ttgacggatc ttcggagaac    780
agctactcct gtacctgccc acccggcttc tacggcaaaa tctgtgaatt gagtgccatg    840
acctgtgcgg acggcccttg ctttaacggg ggtcggtgct cagacagccc cgatggaggg    900
tacagctgcc gctgccccgt gggctactcc ggcttcaact gtgagaagaa aattgactac    960
tgcagctctt caccctgttc taatggtgcc aagtgtgtgg acctcggtga tgcctacctg    1020
tgccgctgcc aggccggctt ctcggggagg cactgtgacg acaacgtgga cgactgcgcc   1080
```

```
tcctccccgt gcgccaacgg gggcacctgc cgggatggcg tgaacgactt ctcctgcacc    1140
tgcccgcctg gctacacggg caggaactgc agtgccccg ccagcaggtg cgagcacgca     1200
ccctgccaca atggggccac ctgccacgag aggggccacc gctatttgtg cgagtgtgcc    1260
cgaagctacg gggtcccaa ctgccanttc ctgctccccg aaactgcccc ccggccccca    1320
cggtggtgga aactccccta aaaaaaccta aagggccgg gggggccca tccccttggt     1380 ggacgtgtgc gccggggtca tccttgtcct catgctgctg ctgggctgtg ccgctgtggt    1440
ggtctgcgtc cggctgaggc tgcagaagca ccggccccca gccgacccct gncgggggga   1500
gacggagacc atgaacaacc tggncaactg ccagcgtgag aaggacatct cagtcagcat   1560
catcggggnc acgcagatca agaacaccaa caagaaggcg gacttccacg gggaccacag   1620
ngccgacaag aatggcttca aggcccgcta cccagnggtg gactataacc tcgtgcagga   1680
cctcaagggt gacgacaccg ccgtcaggga cgcgcacagc aagcgtgaca ccaagtgnca   1740
gccccagggc tcctcagggg aggagaaggg gaccccccgac ccacactcag ggggtggagg   1800
aagcatcttg aaagaaaaag gccggacttc gggcttgttc aactttcaaa agacaancaa   1860
ngtacaagtc ggtgtncgtc atttccgnag gaggaaggnt gactgcgtca taggaanttg   1920
aggtngtaaa ntggnagttg annttggaaa gnnntccccg gattccgntt tcaaagtttt   1980
t                                                                    1981

<210> SEQ ID NO 27
<211> LENGTH: 31
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 27

His Trp Val Arg Ala Pro Leu Glu Val Asp Gly Ile Asp Lys Leu Asp
 1               5                  10                  15

Ile Glu Phe Arg Leu His Leu Ala Gly His Leu Leu Ser Asp Tyr
             20                  25                  30

<210> SEQ ID NO 28
<211> LENGTH: 7
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 28

Ser Ser Pro His Arg Phe Ser
 1               5

<210> SEQ ID NO 29
<211> LENGTH: 45
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 29

Pro Arg Asn Arg Lys Pro Arg Lys Thr His Gln Pro Pro Gly His Pro
 1               5                  10                  15

Glu Ala Pro Asp Gly Gly Arg Gly Val Val Pro Gly Pro Ala Gln Gln
             20                  25                  30
```

Arg Pro His Gly Pro Gln Val Leu Leu Pro Leu Arg Val
        35                  40                  45

<210> SEQ ID NO 30
<211> LENGTH: 49
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 30

Arg Thr Leu Leu Arg Arg Gly Leu Leu Arg Phe Pro Ser Pro Gly Arg
1               5                   10                  15

Cys Leu Arg Pro Leu His Leu Trp Gly Ala Trp Gly Glu Ser Val Gln
            20                  25                  30

Pro Trp Leu Glu Arg Ala Leu Leu His Arg Ala Asp Leu Pro Ala Trp
        35                  40                  45

Met

<210> SEQ ID NO 31
<211> LENGTH: 5
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 31

Ala Ala Trp Ile Leu
1               5

<210> SEQ ID NO 32
<211> LENGTH: 16
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 32

Gln Thr Arg Gly Met Gln Val Gln Ser Gly Leu Ala Gly Pro Val Leu
1               5                   10                  15

<210> SEQ ID NO 33
<211> LENGTH: 40
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 25
<223> OTHER INFORMATION: Xaa = Any Amino Acid

<400> SEQUENCE: 33

Arg Val Tyr Pro Leu Ser Arg Leu Ser Pro Trp His Leu Pro Ala Ala
1               5                   10                  15

Leu Ala Val Gln Leu Pro Gly Arg Xaa Gly Gly Pro Phe Leu Gln Pro
            20                  25                  30

Gly Pro Glu Leu Leu His Thr Pro
        35                  40

<210> SEQ ID NO 34
<211> LENGTH: 45

```
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 27
<223> OTHER INFORMATION: Xaa = Any Amino Acid

<400> SEQUENCE: 34

Ala Leu Gln Glu Trp Ser His Leu Gln Gln Thr Arg Ala Arg Gly Ser
 1               5                  10                  15

Tyr Thr Trp Ser Leu Ala Gly Leu Gly Tyr Xaa Gly Cys His Leu Arg
             20                  25                  30

Ser Leu Gly Ile Gly Arg Val Val Asp Pro Ser Pro Trp
         35                  40                  45

<210> SEQ ID NO 35
<211> LENGTH: 196
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 166, 179
<223> OTHER INFORMATION: Xaa = Any Amino Acid

<400> SEQUENCE: 35

Glu Arg Arg Glu Leu Asp Gly Ser Ser Glu Asn Ser Tyr Ser Cys Thr
 1               5                  10                  15

Cys Pro Pro Gly Phe Tyr Gly Lys Ile Cys Glu Leu Ser Ala Met Thr
             20                  25                  30

Cys Ala Asp Gly Pro Cys Phe Asn Gly Gly Arg Cys Ser Asp Pro Asp
         35                  40                  45

Gly Gly Tyr Ser Cys Arg Cys Pro Val Gly Tyr Ser Gly Phe Asn Cys
     50                  55                  60

Glu Lys Lys Ile Asp Tyr Cys Ser Ser Ser Pro Cys Ser Asn Gly Ala
65                  70                  75                  80

Lys Cys Val Asp Leu Gly Asp Ala Tyr Leu Cys Arg Gly Gln Ala Gly
                 85                  90                  95

Phe Ser Gly Arg His Cys Asp Asp Asn Val Asp Asp Cys Ala Ser Ser
            100                 105                 110

Pro Cys Ala Asn Gly Gly Thr Cys Arg Asp Gly Val Asn Asp Phe Ser
        115                 120                 125

Cys Thr Cys Pro Pro Gly Tyr Thr Gly Arg Asn Cys Ser Ala Pro Ala
    130                 135                 140

Ser Arg Cys Glu His Ala Pro Cys His Asn Gly Ala Thr Cys His Glu
145                 150                 155                 160

Arg Gly His Arg Tyr Xaa Cys Glu Cys Ala Arg Ser Tyr Gly Gly Pro
                165                 170                 175

Asn Cys Xaa Phe Leu Leu Pro Glu Thr Ala Pro Ala Pro Arg Trp
            180                 185                 190

Trp Lys Leu Pro
        195

<210> SEQ ID NO 36
<211> LENGTH: 65
<212> TYPE: PRT
<213> ORGANISM: Artificial Sequence
```

```
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 51
<223> OTHER INFORMATION: Xaa = Any Amino Acid

<400> SEQUENCE: 36

Lys Asn Leu Lys Gly Pro Gly Ala His Pro Leu Gly Gly Arg Val
1               5                   10                  15

Arg Arg Gly His Pro Cys Pro His Ala Ala Ala Gly Leu Cys Arg Cys
                20                  25                  30

Gly Gly Leu Arg Pro Ala Glu Ala Glu Ala Pro Ala Pro Ser Arg
            35                  40                  45

Pro Leu Xaa Gly Gly Asp Gly Asp His Glu Gln Pro Gly Gln Leu Pro
        50                  55                  60

Ala
65

<210> SEQ ID NO 37
<211> LENGTH: 42
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 28, 39
<223> OTHER INFORMATION: Xaa = Any Amino Acid

<400> SEQUENCE: 37

Glu Gly His Leu Ser Gln His His Arg Gly His Ala Asp Gln Glu His
1               5                   10                  15

Gln Gln Glu Gly Gly Leu Pro Arg Gly Pro Gln Xaa Arg Gln Glu Trp
                20                  25                  30

Leu Gln Gly Pro Leu Pro Xaa Gly Gly Leu
            35                  40

<210> SEQ ID NO 38
<211> LENGTH: 7
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 38

Pro Arg Ala Gly Pro Gln Gly
1               5

<210> SEQ ID NO 39
<211> LENGTH: 11
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 39

Arg His Arg Arg Gln Gly Arg Ala Gln Gln Ala
1               5                   10

<210> SEQ ID NO 40
<211> LENGTH: 57
```

```
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 4, 43, 45, 50, 54
<223> OTHER INFORMATION: Xaa = Any Amino Acid

<400> SEQUENCE: 40

His Gln Val Xaa Ala Pro Gly Leu Leu Arg Gly Gly Glu Gly Asp Pro
 1               5                  10                  15

Arg Pro Thr Leu Arg Gly Trp Arg Lys His Leu Glu Arg Lys Arg Pro
            20                  25                  30

Asp Phe Gly Leu Val Gln Leu Ser Lys Asp Xaa Gln Xaa Thr Ser Arg
        35                  40                  45

Cys Xaa Ser Phe Pro Xaa Glu Glu Gly
    50                  55

<210> SEQ ID NO 41
<211> LENGTH: 8
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 5, 8
<223> OTHER INFORMATION: Xaa = Any Amino Acid

<400> SEQUENCE: 41

Leu Arg His Arg Xaa Leu Arg Xaa
 1               5

<210> SEQ ID NO 42
<211> LENGTH: 13
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 1, 4, 5
<223> OTHER INFORMATION: Xaa = Any Amino Acid

<400> SEQUENCE: 42

Xaa Trp Lys Xaa Xaa Pro Gly Phe Arg Phe Gln Ser Phe
 1               5                  10

<210> SEQ ID NO 43
<211> LENGTH: 276
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 226, 230
<223> OTHER INFORMATION: Xaa = Any Amino Acid

<400> SEQUENCE: 43

Ile Gly Tyr Gly Pro Pro Ser Arg Ser Thr Val Ser Ile Ser Leu Ile
 1               5                  10                  15

Ser Asn Ser Gly Phe Thr Trp Pro Gly Thr Phe Ser Leu Ile Ile Glu
            20                  25                  30
```

```
Ala Leu His Thr Asp Ser Pro Asp Leu Ala Thr Glu Asn Pro Glu
        35                  40                  45

Arg Leu Ile Ser Arg Leu Ala Thr Gln Arg His Leu Thr Val Gly Glu
 50                  55                  60

Glu Trp Ser Gln Asp Leu His Ser Ser Gly Arg Thr Asp Leu Lys Tyr
 65                  70                  75                  80

Ser Tyr Arg Phe Val Cys Asp Glu His Tyr Tyr Gly Glu Gly Cys Ser
                 85                  90                  95

Val Phe Cys Arg Pro Arg Asp Asp Ala Phe Gly His Phe Thr Cys Gly
            100                 105                 110

Glu Arg Gly Glu Lys Val Cys Asn Pro Gly Trp Lys Gly Pro Tyr Cys
        115                 120                 125

Thr Glu Pro Ile Cys Leu Pro Gly Cys Asp Glu Gln His Gly Phe Cys
    130                 135                 140

Asp Lys Pro Gly Glu Cys Lys Cys Arg Val Gly Trp Gln Gly Arg Tyr
145                 150                 155                 160

Cys Asp Glu Cys Ile Arg Tyr Pro Gly Cys Leu His Gly Thr Cys Gln
                165                 170                 175

Gln Pro Trp Gln Cys Asn Cys Gln Glu Gly Trp Gly Gly Leu Phe Cys
            180                 185                 190

Asn Gln Asp Leu Asn Tyr Cys Thr His His Lys Pro Cys Lys Asn Gly
        195                 200                 205

Ala Thr Cys Asn Lys His Gly Pro Gly Gly Ala Thr Leu Gly Leu Trp
    210                 215                 220

Pro Xaa Trp Gly Thr Xaa Gly Ala Thr Cys Glu Ala Trp Gly Leu Asp
225                 230                 235                 240

Glu Leu Leu Thr Pro Ala Leu Gly Lys Asn Gly Gly Ser Leu Thr Asp
                245                 250                 255

Leu Arg Arg Thr Ala Thr Pro Val Pro Ala His Pro Ala Ser Thr Ala
            260                 265                 270

Lys Ser Val Asn
        275

<210> SEQ ID NO 44
<211> LENGTH: 93
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 44

Pro Val Arg Thr Ala Leu Ala Leu Thr Gly Val Gly Ala Gln Thr Ala
 1               5                  10                  15

Pro Met Glu Gly Thr Ala Ala Ala Pro Trp Ala Thr Pro Ala Ser
             20                  25                  30

Thr Val Arg Arg Lys Leu Thr Thr Ala Ala Leu His Pro Val Leu Met
            35                  40                  45

Val Pro Ser Val Trp Thr Ser Val Met Pro Thr Cys Ala Ala Ala Arg
     50                  55                  60

Pro Ala Ser Arg Gly Gly Thr Val Thr Thr Trp Thr Thr Ala Pro
 65                  70                  75                  80

Pro Pro Arg Ala Pro Thr Gly Ala Pro Ala Gly Met Ala
                 85                  90

<210> SEQ ID NO 45
```

```
<211> LENGTH: 74
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 55
<223> OTHER INFORMATION: Xaa = Any Amino Acid

<400> SEQUENCE: 45

Thr Thr Ser Pro Ala Pro Ala Arg Leu Ala Thr Arg Ala Gly Thr Ala
1               5                   10                  15

Val Pro Pro Pro Ala Gly Ala Ser Thr His Pro Ala Thr Met Gly Pro
            20                  25                  30

Pro Ala Thr Arg Gly Ala Thr Ala Ile Cys Ala Ser Val Pro Glu Ala
        35                  40                  45

Thr Gly Val Pro Thr Ala Xaa Ser Cys Pro Lys Leu Pro Pro Arg Pro
    50                  55                  60

His Gly Gly Gly Asn Ser Pro Lys Lys Thr
65                  70

<210> SEQ ID NO 46
<211> LENGTH: 187
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 47, 58, 73, 101, 128, 167, 168, 181, 187
<223> OTHER INFORMATION: Xaa = Any Amino Acid

<400> SEQUENCE: 46

Lys Gly Arg Gly Gly Pro Ile Pro Leu Val Asp Val Cys Ala Gly Val
1               5                   10                  15

Ile Leu Val Leu Met Leu Leu Leu Gly Cys Ala Ala Val Val Val Cys
            20                  25                  30

Val Arg Leu Arg Leu Gln Lys His Arg Pro Pro Ala Asp Pro Xaa Arg
        35                  40                  45

Gly Glu Thr Glu Thr Met Asn Asn Leu Xaa Asn Cys Gln Arg Glu Lys
    50                  55                  60

Asp Ile Ser Val Ser Ile Ile Gly Xaa Thr Gln Ile Lys Asn Thr Asn
65                  70                  75                  80

Lys Lys Ala Asp Phe His Gly Asp His Ala Asp Lys Asn Gly Phe Lys
                85                  90                  95

Ala Arg Tyr Pro Xaa Val Asp Tyr Asn Leu Val Gln Asp Leu Lys Gly
            100                 105                 110

Asp Asp Thr Ala Val Arg Asp Ala His Ser Lys Arg Asp Thr Lys Xaa
        115                 120                 125

Gln Pro Gln Gly Ser Ser Gly Glu Glu Gly Thr Pro Asp Pro His Ser
    130                 135                 140

Gly Gly Gly Gly Ser Ile Leu Lys Glu Lys Gly Arg Thr Ser Gly Leu
145                 150                 155                 160

Phe Asn Phe Gln Lys Thr Xaa Xaa Val Gln Val Gly Val Arg His Phe
                165                 170                 175

Arg Arg Arg Lys Xaa Asp Cys Val Ile Gly Xaa
            180                 185
```

```
<210> SEQ ID NO 47
<211> LENGTH: 20
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 2, 4, 5, 7, 8, 11, 16
<223> OTHER INFORMATION: Xaa = Any Amino Acid

<400> SEQUENCE: 47

Gly Xaa Lys Xaa Xaa Val Xaa Xaa Gly Lys Xaa Ser Pro Asp Ser Xaa
 1               5                  10                  15

Phe Lys Val Phe
            20

<210> SEQ ID NO 48
<211> LENGTH: 12
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 48

Leu Gly Thr Gly Pro Pro Arg Gly Arg Arg Tyr Arg
 1               5                  10

<210> SEQ ID NO 49
<211> LENGTH: 13
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 49

Tyr Arg Ile Pro Ala Ser Pro Gly Arg Ala Pro Ser Leu
 1               5                  10

<210> SEQ ID NO 50
<211> LENGTH: 30
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 50

Leu Leu Lys Leu Ser Thr Gln Ile Leu Leu Met Thr Ser Gln Gln Lys
 1               5                  10                  15

Thr Gln Lys Asp Ser Ser Ala Ala Trp Pro Pro Arg Gly Thr
            20                  25                  30

<210> SEQ ID NO 51
<211> LENGTH: 135
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 126
<223> OTHER INFORMATION: Xaa = Any Amino Acid

<400> SEQUENCE: 51
```

```
Arg Trp Ala Arg Ser Gly Pro Arg Thr Cys Thr Ala Ala Ala Arg
  1               5                  10                 15

Thr Ser Ser Thr Pro Thr Ala Ser Cys Val Thr Asn Thr Thr Thr Glu
             20                  25                  30

Arg Ala Ala Pro Phe Ser Ala Val Pro Gly Thr Met Pro Ser Ala Thr
             35                  40                  45

Ser Pro Val Cys Ser Val Gly Arg Lys Cys Ala Thr Leu Ala Gly Lys
 50                  55                  60

Gly Pro Thr Ala Gln Ser Arg Ser Ala Cys Leu Asp Val Met Ser Ser
 65                  70                  75                  80

Met Asp Phe Phe Val Thr Asn Gln Asn Ala Ser Ala Glu Trp Ala Gly
                 85                  90                  95

Arg Ala Gly Thr Val Thr Ser Val Ser Ala Ile Gln Ala Val Ser Met
                100                 105                 110

Ala Pro Ala Ser Ser Pro Gly Ser Ala Thr Ala Arg Lys Xaa Gly Gly
            115                 120                 125

Ala Phe Ser Ala Thr Arg Thr
        130                 135
```

<210> SEQ ID NO 52
<211> LENGTH: 46
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 30, 33
<223> OTHER INFORMATION: Xaa = Any Amino Acid

<400> SEQUENCE: 52

```
Thr Thr Ala His Thr Ile Ser Pro Ala Arg Met Glu Pro Pro Ala Thr
  1               5                  10                 15

Asn Thr Gly Gln Gly Glu Leu His Leu Val Phe Gly Arg Xaa Gly Val
             20                  25                  30

Xaa Arg Val Pro Pro Ala Lys Leu Gly Asp Trp Thr Ser Cys
         35                  40                  45
```

<210> SEQ ID NO 53
<211> LENGTH: 10
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 53

```
Pro Gln Pro Leu Val Arg Thr Glu Gln Glu
  1               5                  10
```

<210> SEQ ID NO 54
<211> LENGTH: 20
<212> TYPE: PRT
<213> ORGANISM: Artificial Sequence
<220> FEATURE:
<223> OTHER INFORMATION: Deduced amino acid sequence using the three
      possible ORF of human Delta contigs

<400> SEQUENCE: 54

```
Arg Ile Phe Gly Glu Gln Leu Leu Leu Tyr Leu Pro Thr Arg Leu Leu
  1               5                  10                 15

Arg Gln Asn Leu
```

<210> SEQ ID NO 55
<211> LENGTH: 12
<212> TYPE: PRT
<213> ORGANISM: Artificial Sequence
<220> FEATURE:
<223> OTHER INFORMATION: Deduced amino acid sequence using the three possible ORF of human Delta contigs

<400> SEQUENCE: 55

Ile Glu Cys His Asp Leu Cys Gly Arg Pro Leu Leu
1               5                   10

<210> SEQ ID NO 56
<211> LENGTH: 25
<212> TYPE: PRT
<213> ORGANISM: Artificial Sequence
<220> FEATURE:
<223> OTHER INFORMATION: Deduced amino acid sequence using the three possible ORF of human Delta contigs

<400> SEQUENCE: 56

Arg Gly Ser Val Leu Arg Gln Pro Arg Trp Arg Val Gln Leu Pro Leu
1               5                   10                  15

Pro Arg Gly Leu Leu Arg Leu Gln Leu
            20                  25

<210> SEQ ID NO 57
<211> LENGTH: 8
<212> TYPE: PRT
<213> ORGANISM: Artificial Sequence
<220> FEATURE:
<223> OTHER INFORMATION: Deduced amino acid sequence using the three possible ORF of human Delta contigs

<400> SEQUENCE: 57

Leu Leu Gln Leu Phe Thr Leu Phe
1               5

<210> SEQ ID NO 58
<211> LENGTH: 8
<212> TYPE: PRT
<213> ORGANISM: Artificial Sequence
<220> FEATURE:
<223> OTHER INFORMATION: Deduced amino acid sequence using the three possible ORF of human Delta contigs

<400> SEQUENCE: 58

Trp Cys Gln Val Cys Gly Pro Arg
1               5

<210> SEQ ID NO 59
<211> LENGTH: 15
<212> TYPE: PRT
<213> ORGANISM: Artificial Sequence
<220> FEATURE:
<223> OTHER INFORMATION: Deduced amino acid sequence using the three possible ORF of human Delta contigs

<400> SEQUENCE: 59

Cys Leu Pro Val Pro Leu Pro Gly Arg Leu Leu Gly Glu Ala Leu
1               5                   10                  15

<210> SEQ ID NO 60
<211> LENGTH: 131
<212> TYPE: PRT
<213> ORGANISM: Artificial Sequence

```
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 76
<223> OTHER INFORMATION: Xaa = Any Amino Acid

<400> SEQUENCE: 60

Arg Gln Arg Gly Arg Leu Arg Leu Pro Val Arg Gln Gly His Leu
1               5                   10                  15

Pro Gly Trp Arg Glu Arg Leu Leu Leu His Leu Pro Ala Trp Leu His
            20                  25                  30

Gly Gln Glu Leu Gln Cys Pro Arg Gln Val Arg Ala Arg Thr Leu
        35                  40                  45

Pro Gln Trp Gly His Leu Pro Arg Glu Gly Pro Leu Phe Val Arg
    50                  55                  60

Val Cys Pro Lys Leu Arg Gly Ser Gln Leu Pro Xaa Pro Ala Pro Arg
65                  70                  75                  80

Asn Cys Pro Pro Gly Pro Thr Val Val Glu Thr Pro Leu Lys Lys Pro
                85                  90                  95

Lys Arg Ala Gly Gly Pro Ser Pro Trp Trp Thr Cys Ala Pro Gly
            100                 105                 110

Ser Ser Leu Ser Ser Cys Cys Cys Trp Ala Val Pro Leu Trp Trp Ser
            115                 120                 125

Ala Ser Gly
        130

<210> SEQ ID NO 61
<211> LENGTH: 18
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 12
<223> OTHER INFORMATION: Xaa = Any Amino Acid

<400> SEQUENCE: 61

Gly Cys Arg Ser Thr Gly Pro Gln Pro Thr Pro Xaa Gly Gly Arg Arg
1               5                   10                  15

Arg Pro

<210> SEQ ID NO 62
<211> LENGTH: 98
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 4, 19, 36, 48, 75
<223> OTHER INFORMATION: Xaa = Any Amino Acid

<400> SEQUENCE: 62

Thr Thr Trp Xaa Thr Ala Ser Val Arg Arg Thr Ser Gln Ser Ala Ser
1               5                   10                  15

Ser Gly Xaa Arg Arg Ser Arg Thr Pro Thr Arg Arg Thr Ser Thr
            20                  25                  30

Gly Thr Thr Xaa Pro Thr Arg Met Ala Ser Arg Pro Ala Thr Gln Xaa
            35                  40                  45
```

```
Trp Thr Ile Thr Ser Cys Arg Thr Ser Arg Val Thr Thr Pro Pro Ser
    50                  55                  60

Gly Thr Arg Thr Ala Ser Val Thr Pro Ser Xaa Ser Pro Arg Ala Pro
65                  70                  75                  80

Gln Gly Arg Arg Arg Cys Pro Pro Thr His Thr Gln Gly Val Glu Glu
                85                  90                  95

Ala Ser

<210> SEQ ID NO 63
<211> LENGTH: 33
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 16, 17, 22, 26, 30
<223> OTHER INFORMATION: Xaa = Any Amino Acid

<400> SEQUENCE: 63

Lys Lys Lys Ala Gly Leu Arg Ala Cys Ser Thr Phe Lys Arg Gln Xaa
1               5                   10                  15

Xaa Tyr Lys Ser Val Xaa Val Ile Ser Xaa Gly Gly Arg Xaa Thr Ala
            20                  25                  30

Ser

<210> SEQ ID NO 64
<211> LENGTH: 22
<212> TYPE: PRT
<213> ORGANISM: Artificial Sequence
<220> FEATURE:
<223> OTHER INFORMATION: Deduced amino acid sequence using the three
      possible ORF of human Delta contigs
<220> FEATURE:
<221> NAME/KEY: VARIANT
<222> LOCATION: 2, 6, 8, 10, 13, 14, 19
<223> OTHER INFORMATION: Xaa = Any Amino Acid

<400> SEQUENCE: 64

Glu Xaa Glu Val Val Xaa Trp Xaa Leu Xaa Leu Glu Xaa Xaa Pro Arg
1               5                   10                  15

Ile Pro Xaa Ser Lys Phe
            20

<210> SEQ ID NO 65
<211> LENGTH: 192
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 65

Gly Phe Thr Trp Pro Gly Thr Phe Ser Leu Ile Ile Glu Ala Leu His
1               5                   10                  15

Thr Asp Ser Pro Asp Asp Leu Ala Thr Glu Asn Pro Glu Arg Leu Ile
            20                  25                  30

Ser Arg Leu Ala Thr Gln Arg His Leu Thr Val Gly Glu Glu Trp Ser
        35                  40                  45

Gln Asp Leu His Ser Ser Gly Arg Thr Asp Leu Lys Tyr Ser Tyr Arg
    50                  55                  60

Phe Val Cys Asp Glu His Tyr Tyr Gly Glu Gly Cys Ser Val Phe Cys
```

```
                65                  70                  75                  80
Arg Pro Arg Asp Asp Ala Phe Gly His Phe Thr Cys Gly Glu Arg Gly
                        85                  90                  95

Glu Lys Val Cys Asn Pro Gly Trp Lys Gly Pro Tyr Cys Thr Glu Pro
                100                 105                 110

Ile Cys Leu Pro Gly Cys Asp Glu Gln His Gly Phe Cys Asp Lys Pro
                115                 120                 125

Gly Glu Cys Lys Cys Arg Val Gly Trp Gln Gly Arg Tyr Cys Asp Glu
            130                 135                 140

Cys Ile Arg Tyr Pro Gly Cys Leu His Gly Thr Cys Gln Gln Pro Trp
145                 150                 155                 160

Gln Cys Asn Cys Gln Glu Gly Trp Gly Gly Leu Phe Cys Asn Gln Asp
                165                 170                 175

Leu Asn Tyr Cys Thr His His Lys Pro Cys Lys Asn Gly Ala Thr Cys
                180                 185                 190
```

<210> SEQ ID NO 66
<211> LENGTH: 6
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 66

```
Thr Asn Thr Gly Gln Gly
1               5
```

<210> SEQ ID NO 67
<211> LENGTH: 9
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 67

```
Lys Asn Gly Gly Ser Leu Thr Asp Leu
1               5
```

<210> SEQ ID NO 68
<211> LENGTH: 157
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 68

```
Glu Asn Ser Tyr Ser Cys Thr Cys Pro Pro Gly Phe Tyr Gly Lys Ile
1               5                   10                  15

Cys Glu Leu Ser Ala Met Thr Cys Ala Asp Gly Pro Cys Phe Asn Gly
                20                  25                  30

Gly Arg Cys Ser Asp Ser Pro Asp Gly Gly Tyr Ser Cys Arg Cys Pro
            35                  40                  45

Val Gly Tyr Ser Gly Phe Asn Cys Glu Lys Lys Ile Asp Tyr Cys Ser
    50                  55                  60

Ser Ser Pro Cys Ser Asn Gly Ala Lys Cys Val Asp Leu Gly Asp Ala
65                  70                  75                  80

Tyr Leu Cys Arg Cys Gln Ala Gly Phe Ser Gly Arg His Cys Asp Asp
                85                  90                  95
```

-continued

```
Asn Val Asp Asp Cys Ala Ser Ser Pro Cys Ala Asn Gly Gly Thr Cys
                100                 105                 110

Arg Asp Gly Val Asn Asp Phe Ser Cys Thr Cys Pro Pro Gly Tyr Thr
            115                 120                 125

Gly Arg Asn Cys Ser Ala Pro Ala Ser Arg Cys Glu His Ala Pro Cys
        130                 135                 140

His Asn Gly Ala Thr Cys His Glu Arg Gly His Arg Tyr
145                 150                 155

<210> SEQ ID NO 69
<211> LENGTH: 12
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 69

Cys Glu Cys Ala Arg Ser Tyr Gly Gly Pro Asn Cys
1               5                   10

<210> SEQ ID NO 70
<211> LENGTH: 5
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 70

Phe Leu Leu Pro Glu
1               5

<210> SEQ ID NO 71
<211> LENGTH: 4
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 71

Pro Pro Gly Pro
1

<210> SEQ ID NO 72
<211> LENGTH: 25
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 72

Leu Leu Leu Gly Cys Ala Ala Val Val Val Cys Val Arg Leu Arg Leu
1               5                   10                  15

Gln Lys His Arg Pro Pro Ala Asp Pro
            20                  25

<210> SEQ ID NO 73
<211> LENGTH: 10
<212> TYPE: PRT
<213> ORGANISM: Artificial Sequence
<220> FEATURE:
<223> OTHER INFORMATION: Composite human delta (H-Delta-1) amino acid
      sequence
```

-continued

```
<400> SEQUENCE: 73

Arg Gly Glu Thr Glu Thr Met Asn Asn Leu
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 74

Asn Cys Gln Arg Glu Lys Asp Ile Ser Val Ser Ile Ile Gly
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 75

Thr Gln Ile Lys Asn Thr Asn Lys Lys Ala Asp Phe His Gly Asp His
1               5                   10                  15

<210> SEQ ID NO 76
<211> LENGTH: 11
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 76

Ala Asp Lys Asn Gly Phe Lys Ala Arg Tyr Pro
1               5                   10

<210> SEQ ID NO 77
<211> LENGTH: 26
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 77

Val Asp Tyr Asn Leu Val Gln Asp Leu Lys Gly Asp Asp Thr Ala Val
1               5                   10                  15
Arg Asp Ala His Ser Lys Arg Asp Thr Lys
                20                  25

<210> SEQ ID NO 78
<211> LENGTH: 13
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 78

Gln Pro Gln Gly Ser Ser Gly Glu Glu Lys Gly Thr Pro
1               5                   10

<210> SEQ ID NO 79
```

```
<211> LENGTH: 4
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 79

Pro Thr Leu Arg
 1

<210> SEQ ID NO 80
<211> LENGTH: 4
<212> TYPE: PRT
<213> ORGANISM: Artificial Sequence
<220> FEATURE:
<223> OTHER INFORMATION: Composite human delta (H-Delta-1) amino acid
      sequence

<400> SEQUENCE: 80

Arg Lys Arg Pro
 1

<210> SEQ ID NO 81
<211> LENGTH: 23
<212> TYPE: DNA
<213> ORGANISM: Artificial Sequence
<220> FEATURE:
<223> OTHER INFORMATION: Degenerated oligo as primer
<220> FEATURE:
<221> NAME/KEY: VARIANT
<222> LOCATION: 6, 12, 18, 21
<223> OTHER INFORMATION: n = I (Inosine)

<400> SEQUENCE: 81
ttcggnttya cntggccngg nac                                             23

<210> SEQ ID NO 82
<211> LENGTH: 20
<212> TYPE: DNA
<213> ORGANISM: Artificial Sequence
<220> FEATURE:
<223> OTHER INFORMATION: Degenerated oligo as primer
<220> FEATURE:
<221> NAME/KEY: VARIANT
<222> LOCATION: 3, 9, 12, 15
<223> OTHER INFORMATION: n = I (Inosine)

<400> SEQUENCE: 82
tcnatgcang tnccnccrtt                                                 20

<210> SEQ ID NO 83
<211> LENGTH: 8
<212> TYPE: PRT
<213> ORGANISM: Drosophila

<400> SEQUENCE: 83

Phe Gly Phe Thr Trp Pro Gly Thr
 1               5

<210> SEQ ID NO 84
<211> LENGTH: 7
<212> TYPE: PRT
<213> ORGANISM: Drosophila

<400> SEQUENCE: 84

Asn Gly Gly Thr Cys Ile Asp
 1               5
```

```
<210> SEQ ID NO 85
<211> LENGTH: 12
<212> TYPE: PRT
<213> ORGANISM: Drosophila

<400> SEQUENCE: 85

Ser Ile Pro Pro Gly Ser Arg Thr Ser Leu Gly Val
  1               5                  10

<210> SEQ ID NO 86
<211> LENGTH: 23
<212> TYPE: DNA
<213> ORGANISM: Artificial Sequence
<220> FEATURE:
<223> OTHER INFORMATION: Primer 1 for PCR
<220> FEATURE:
<221> NAME/KEY: VARIANT
<222> LOCATION: 3, 9, 15, 18, 21
<223> OTHER INFORMATION: n = I (Inosine)

<400> SEQUENCE: 86
ggnttcacnt ggccnggnac ntt                                              23

<210> SEQ ID NO 87
<211> LENGTH: 23
<212> TYPE: DNA
<213> ORGANISM: Artificial Sequence
<220> FEATURE:
<223> OTHER INFORMATION: Primer 2 for PCR
<220> FEATURE:
<221> NAME/KEY: VARIANT
<222> LOCATION: 3, 6, 18
<223> OTHER INFORMATION: n = I (Inosine)

<400> SEQUENCE: 87
gtnccnccrt tyttrcangg rtt                                              23

<210> SEQ ID NO 88
<211> LENGTH: 8
<212> TYPE: PRT
<213> ORGANISM: Artificial Sequence
<220> FEATURE:
<223> OTHER INFORMATION: EGF-like repeats encoded by SEQ ID NO. 87

<400> SEQUENCE: 88

Asn Pro Cys Lys Asn Gly Gly Thr
  1               5

<210> SEQ ID NO 89
<211> LENGTH: 23
<212> TYPE: DNA
<213> ORGANISM: Artificial Sequence
<220> FEATURE:
<223> OTHER INFORMATION: degenerated oligo primer
<220> FEATURE:
<221> NAME/KEY: VARIANT
<222> LOCATION: 3, 15, 18
<223> OTHER INFORMATION: n = I (Inosine)

<400> SEQUENCE: 89
acnatgaaya ayctngcnaa ytg                                              23

<210> SEQ ID NO 90
<211> LENGTH: 8
<212> TYPE: PRT
<213> ORGANISM: Artificial Sequence
<220> FEATURE:
<223> OTHER INFORMATION: amino acid encoded by SEQ ID NO. 89
```

```
<400> SEQUENCE: 90

Thr Met Asn Asn Leu Ala Asn Cys
 1               5

<210> SEQ ID NO 91
<211> LENGTH: 23
<212> TYPE: DNA
<213> ORGANISM: Artificial Sequence
<220> FEATURE:
<223> OTHER INFORMATION: degenerated oligo primer
<220> FEATURE:
<221> NAME/KEY: VARIANT
<222> LOCATION: 6, 9, 21
<223> OTHER INFORMATION: n = I (Inosine)

<400> SEQUENCE: 91
acrtanacng aytgrtaytt ngt                                          23

<210> SEQ ID NO 92
<211> LENGTH: 8
<212> TYPE: PRT
<213> ORGANISM: Artificial Sequence
<220> FEATURE:
<223> OTHER INFORMATION: amino acid sequence encoded by SEQ ID NO. 91

<400> SEQUENCE: 92

Thr Lys Tyr Gln Ser Val Tyr Val
 1               5

<210> SEQ ID NO 93
<211> LENGTH: 23
<212> TYPE: DNA
<213> ORGANISM: Artificial Sequence
<220> FEATURE:
<223> OTHER INFORMATION: degenerated oligo
<220> FEATURE:
<221> NAME/KEY: VARIANT
<222> LOCATION: 6
<223> OTHER INFORMATION: n = I (Inosine)

<400> SEQUENCE: 93
gcdatnacrc aytcrtcytt ytc                                          23

<210> SEQ ID NO 94
<211> LENGTH: 8
<212> TYPE: PRT
<213> ORGANISM: Artificial Sequence
<220> FEATURE:
<223> OTHER INFORMATION: amino acid sequence endoced by SEQ ID NO. 86

<400> SEQUENCE: 94

Gly Phe Thr Trp Pro Gly Thr Phe
 1               5

<210> SEQ ID NO 95
<211> LENGTH: 129
<212> TYPE: PRT
<213> ORGANISM: Gallus gallus
<220> FEATURE:
<223> OTHER INFORMATION: chicken C-Delta-1

<400> SEQUENCE: 95

Thr Met Asn Asn Leu Ala Asn Cys Gln Arg Glu Lys Asp Ile Ser Ile
 1               5                  10                  15

Ser Val Ile Gly Ala Thr Gln Ile Lys Asn Thr Asn Lys Lys Val Asp
             20                  25                  30

Phe His Ser Asp Asn Ser Asp Lys Asn Gly Tyr Lys Val Arg Tyr Pro
```

```
                35                    40                     45
Ser Val Asp Tyr Asn Leu Val His Glu Leu Lys Asn Glu Asp Ser Val
    50                  55                  60

Lys Glu Glu His Gly Lys Cys Glu Ala Lys Cys Glu Thr Tyr Asp Ser
65                  70                  75                  80

Glu Ala Glu Glu Lys Ser Ala Val Gln Leu Lys Ser Ser Asp Thr Ser
                85                  90                  95

Glu Arg Lys Arg Pro Asp Ser Val Tyr Ser Thr Ser Lys Asp Thr Lys
            100                 105                 110

Tyr Gln Ser Val Tyr Val Ile Ser Glu Glu Lys Asp Glu Cys Ile Ile
        115                 120                 125

Ala
```